(12) United States Patent
Nizet et al.

(10) Patent No.: US 11,771,751 B2
(45) Date of Patent: Oct. 3, 2023

(54) **STREPTOCOCCAL GLCNAC-LACKING GLYCOPOLYPEPTIDES, CELL WALL CARBOHYDRATES, *STREPTOCOCCUS* VACCINES, AND METHODS FOR MAKING AND USING THEM**

(71) Applicant: The Regents of the University of California, Oakland, CA (US)

(72) Inventors: Victor Nizet, San Diego, CA (US); Nina van Sorge, Utrecht (NL)

(73) Assignee: The Regents of the University of California, Oakland, CA (US)

( * ) Notice: Subject to any disclaimer, the term of this patent is extended or adjusted under 35 U.S.C. 154(b) by 11 days.

(21) Appl. No.: 17/002,337

(22) Filed: Aug. 25, 2020

(65) Prior Publication Data

US 2021/0170012 A1 Jun. 10, 2021

Related U.S. Application Data

(60) Continuation of application No. 15/265,800, filed on Sep. 14, 2016, now Pat. No. 10,780,155, which is a division of application No. 14/237,120, filed as application No. PCT/US2012/049604 on Aug. 3, 2012, now abandoned.

(60) Provisional application No. 61/515,287, filed on Aug. 4, 2011.

(51) Int. Cl.
| | |
|---|---|
| *A61K 47/64* | (2017.01) |
| *A61K 39/09* | (2006.01) |
| *C07K 14/315* | (2006.01) |
| *C07K 16/12* | (2006.01) |
| *C07K 16/44* | (2006.01) |
| *C08B 37/00* | (2006.01) |
| *G01N 33/53* | (2006.01) |
| *G01N 33/569* | (2006.01) |
| *C12N 1/20* | (2006.01) |
| *C12N 1/36* | (2006.01) |
| *A61K 39/00* | (2006.01) |

(52) U.S. Cl.
CPC .......... *A61K 39/092* (2013.01); *A61K 47/646* (2017.08); *C07K 14/315* (2013.01); *C07K 16/1275* (2013.01); *C07K 16/44* (2013.01); *C08B 37/0006* (2013.01); *C12N 1/20* (2013.01); *C12N 1/36* (2013.01); *G01N 33/5308* (2013.01); *G01N 33/56944* (2013.01); *A61K 2039/522* (2013.01)

(58) Field of Classification Search
None
See application file for complete search history.

(56) References Cited

U.S. PATENT DOCUMENTS

| | | | |
|---|---|---|---|
| 5,866,134 A * | 2/1999 | Fine | A61K 39/39 424/234.1 |
| 5,866,135 A | 2/1999 | Blake et al. | |
| 6,248,329 B1 * | 6/2001 | Chandrashekar | C07K 14/4354 424/191.1 |
| 10,780,155 B2 * | 9/2020 | Nizet | G01N 33/5308 |
| 2001/0014332 A1 | 8/2001 | Minetti et al. | |
| 2007/0207454 A1 | 9/2007 | Fischetti et al. | |

FOREIGN PATENT DOCUMENTS

WO 96-08569 A2 3/1996

OTHER PUBLICATIONS

Jones et al, Vaccine 36:3756-63, 2018.*
Rivera-Hernandez et al mBio, 7(3):e618-16, pp. 1-9, May/Jun. 2016.*
The Dictionary of Immunology, Herbert et al eds, Academic Press, 1995.*
Feng et al (Infection and Immunity, 64(1):363-365, 1996).*
Ayoub, Elia M. et al., "Temperature-Dependent Variation in the Synthesis of Group-Specific Carbohydrate By Streptococcal Variant Strains," The Journal of Experimental Medicine, 138:1973, pp. 117-129.
Bahartou, Simin, International Preliminary Report on Patentability, PCT/US2012/049604, The International Bureau of WIPO, dated Feb. 13, 2014.
Coligan, John E. et al., "Immunochemical and Chemical Studies on Streptococcal Group-Specific Carbohydrates," Journal of Immunology, 1975, 114, pp. 1654-1658.
Kabanova, Anna et al., "Evaluation of a group A *Strepococcus* synthetic oligosaccharide as vaccine candidate", Vaccine, 2011, (epub. Sep. 24, 2010), vol. 29, pp. 104-114.
Lee, Jae Yeong, Search Report and Written Opinion, PCT/US2012/049604, Korean Intellectual Property Office, dated Feb. 28, 2013.
McCarty, Maclyn et al., "Variation in the Group-Specific Carbohydrate of Group a Streptococci," Jems, vol. 102, No. 1, Jul. 1, 1955, pp. 11-28.
McCarty, Maclyn, "Variation in the Group-Specific Carbohydrate of Group A Streptococci," The Journal of Experimenta Medicine, Published Nov. 1, 1956, pp. 629-643.
McNeil, Shelly A. et al., "Safety and Immunogenicity of 26-Valent Group A *Streptococcus* Vaccine in Healthy Adult Volunteers," Clinical Infectious Diseases, Oct. 2005, vol. 41, pp. 1114-1122.

(Continued)

*Primary Examiner* — S. Devi
(74) *Attorney, Agent, or Firm* — Gavrilovich, Dodd & Lindsey LLP

(57) ABSTRACT

In alternative embodiments, the invention provides vaccines, pharmaceutical compounds and formulations for diagnosing, preventing, treating or ameliorating Group A *Streptococcus* (GAS), Group C *Streptococcus* (GCS), or Group A *Streptococcus* (GGS), infections, or other pathogenic *Streptococcus* infections. In alternative embodiments, the invention provides compositions such as diagnostic tests, assays, immunoassays and test strips, and methods, for detecting or diagnosing the presence of a Streptococcal infection, e.g., Group A *Streptococcus* (GAS), Group C *Streptococcus* (GCS), or Group A *Streptococcus* (GGS), infections, or other pathogenic *Streptococcus* infections.

18 Claims, 66 Drawing Sheets

(56) References Cited

OTHER PUBLICATIONS

Osterland, Kirk et al., "Characteristics of Streptococcal Group-Specific Antibody Isolated From Hyperimmune Rabbits," The Journal of Experimental Medicine, 1996, 123(4), pp. 599-614.

Salvadori, L.G et al., "Group A *Streptococcus*-Liposome ELISA Antibody Titers to Group A Polysaccharide and Opsonophagocytic Capabilities of the Antibodies," The Journal of Infectious Diseases, 1995, 171, pp. 593-600.

Shikhman, Alexander R. et al., "A subset of mouse monoclonal antibodies cross-reactive with cytoskeletal proteins and group A Streptococcal M proteins recognizes N-acetyl-beta-d-glucosamine", The Journal of Immunology, 1993, vol. 151, No. 7, pp. 3902-3913.

* cited by examiner

Streptococcus pyogenes (GAS)

- *S. pyogenes* (GAS): Gram-positive β-hemolytic cocci

- GAS is a significant cause of mortality and morbidity
  — common localized infections: strep throat, impetigo, cellulitis

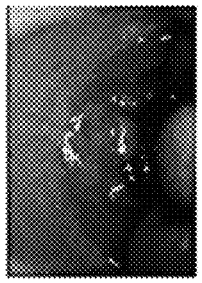

— Severe GAS infection:
  - Invasive disease: bacteremia, necrotizing fasciitis, toxic shock syndrome
  - Acute rheumatic fever, rheumatic heart disease, post-streptococcal glomerulonephritis

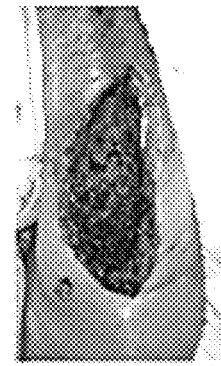

FIG. 3

GAS carbohydrate antigen

- Group A carbohydrate is a polymer of rhamnose and N-acetylglucosamine (GlcNAc)

$$\text{-α-L-Rhap-(1→2)-α-L-Rhap-(1→3)-α-L-Rhap-(1→2)-α-L-Rhap-(1→3)-}$$
$$\qquad\qquad\uparrow 3 \qquad\qquad\qquad\qquad\uparrow 3$$
$$\qquad\text{β-D-GlcpNAc} \qquad\qquad\text{β-D-GlcpNAc}$$

- Group A polysaccharide is located on both the outer and inner surfaces of isolated cell walls (similar to GBS and GCS)

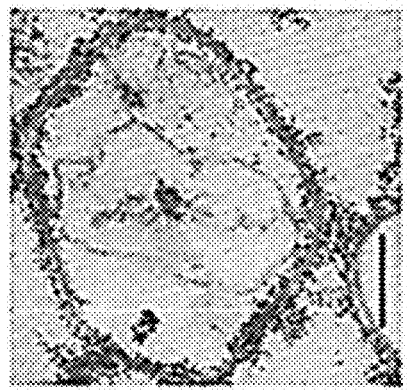

FIG. 5A
GBC localization on whole bacteria

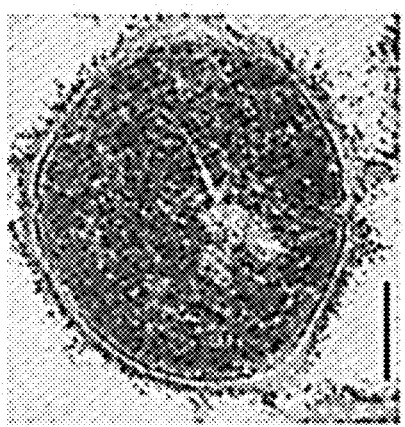

FIG. 5B
GBC localization on GBS cell walls

GAS carbohydrate: natural variant

- A-variant GAS
  - 1945, AT Wilson: mouse passage of GAS can result in loss of Group A carbohydrate (infrequent event)
  - 1956, M McCarty: A-variant carbohydrate contains less/no GlcNAc
  - 1973, J Swanson: No differences noted in morphological characteristics noted of Group A-variant streptococcal cell walls by EM
  - No such variants have ever been isolated from humans: requirement for side chain?

Staining of intact GAS with ferritin-conj Group A antibodies

GAS

*FIG. 6A*

GAS variant

Spy0610 allelic exchange mutant

- Mutant confirmed by PCR analysis and restriction digest

- Latex bead test

ΔGacI characterization (1)

- Growth characteristics

- Lectin stain:sWGA stain
  — sWGA recognizes GlcNAc
  — Mutant shows reduced sWGA stain
    → indicates lack of GlcNAc
    ⇒ only partial complementation by plasmid complementation

ΔGacI characterization (2)

* Surface charge (cytochrome C assay):
    — Cyt. C is positively charged
    — Mutant binds less Cyt. C
    → Mutant is less negatively charged

* Hydrophobicity (stat. phase)
    — Mutant is more hydrophobic

FIG. 14A-B

GlcNac side chain affects C3b deposition in absence of specific IgG

- C3b complement deposition (Suzan Rooijakkers)
  - C3b deposition is only affected in the absence of specific IgG

↓ differential activation of lectin pathway?

Classical complement pathway

Lectin pathway

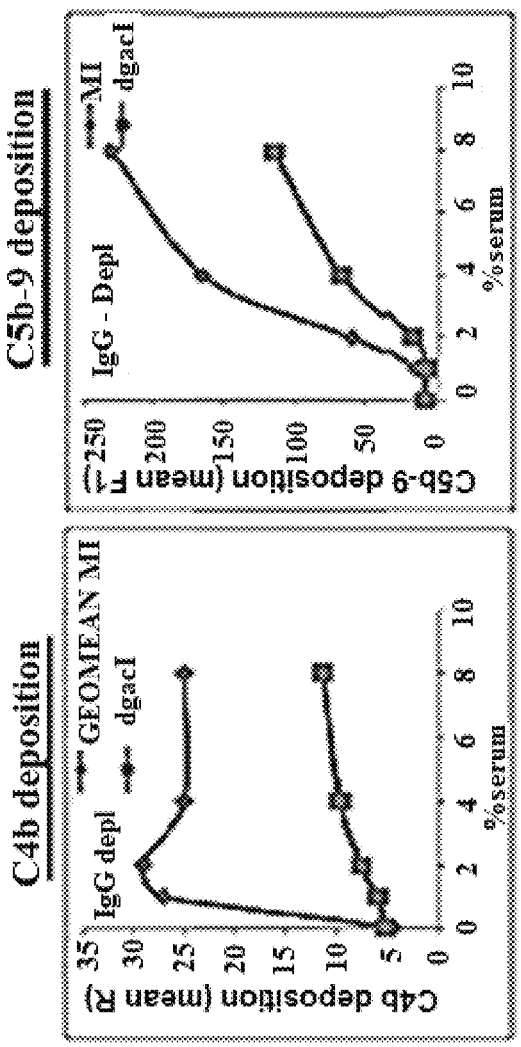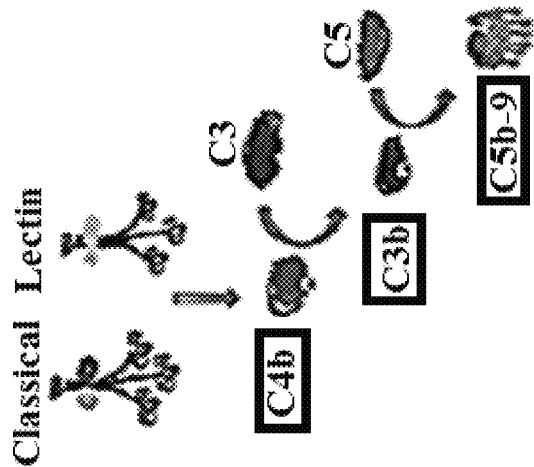
FIG. 23A, FIG. 23B, FIG. 23C

Summary GAC knockout

- Effects of knocking off the Group A carbohydrate GlcNAc side chain:

Affects
- Surface charge (less -)
- Hydrophobicity (increased)
- Chain length (increased)?
- Whole blood survival ↓
- Serum survival ↓
- LL37 susceptibility
- Antibiotic susceptibility
- Complement deposition in absence of IgG ↓
- Systemic virulence in mice +/-

**

Group C streptococcus (GCS)

- GCS :Gram-positive β-hemolytic cocci, multiple species within this group
  - *Streptococcus equi* subsp. *zooepidemicus*: 67% of proteins similar to proteins in GAS (*hasABC* operon, SLS, *spyCEP* etc) Beres et al. PLoS One. 2008

- Opportunistic pathogen in non-human animal species (mastitis)

- Also the cause of human infection through zoonotic transmission and unpasteurized milk/milk products
  - meningitis and bacteremia, and poststreptococcal glomerulonephritis

- Group C carbohydrate structure

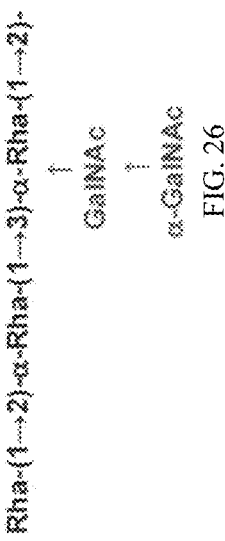

FIG. 26

Heterologous expression of *gccL-N* in GAS (1)

- Analysis of carbohydrate switching with *gccL-N*:
  1. Latex bead test: +/-

GCS WT | GAS WT | WT +pDC_*gccL-N*

FIG. 36A-B

Bioinformatics: Discovery of Operon Encoding the Group A Carbohydrate Antigen

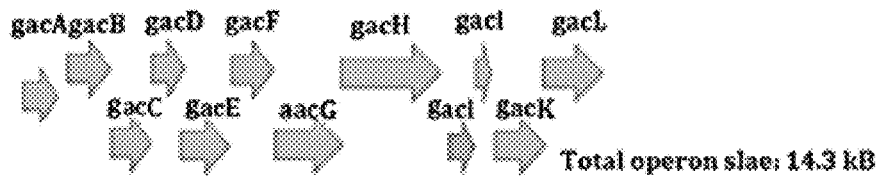

gacA: dTDP-4-dehydrorhamnose reductase: M5005_Spy_0602, 855 bp
gacB: alpha-1,2-L-rhamnosyltransferase: M5005_Spy_0603, 1155 bp
gacC: alpha-L-Rha alpha-1,3-L-rhamnosyltransferase: M5005_Spy_0604, 933 bp
gacD: Polysaccharide export ABC transporter permease protein: M5005_Spy_0605, 804 bp
gacE: Polysaccharide export ATP-binding protien: M5005_Spy_0606, 1206 bp
gacF: Glycosyltransferase: M5005_Spy_0607, 1008 bp
gacG: alpha-L-Rha alpha-1,2-L-rhamnosyltranserase/alpha-L-Rha, alpha-1,3-L-rhamnosyltransferase: M5005_Spy_0608, 1746 bp
gacH: Phosphoglycerol transferase: M5005_Spy_0609, 2475 bp
gacI: Glycosyltransferase, M5005_Spy_0610, 696 bp
gacJ: Hypothetical protein, M5005_Spy_0611, 342 bp
gacK: Polysaccharide biosynthesis protein: M5005_Spy_0612, 1287 bp
gacL: hypothetical membrane spanning protein: M5005_Spy_0613, 1497 bp

*FIG. 38*

The gacI Gene Encodes Addition of GlcNac Side Chain - Latex Test Negative Mutant

* Mutant confirmed by PCR analysis and restriction digest

Internal primers

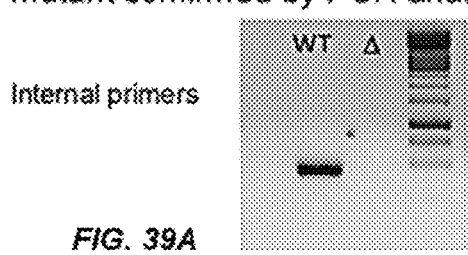

*FIG. 39A*

* Latex bead test

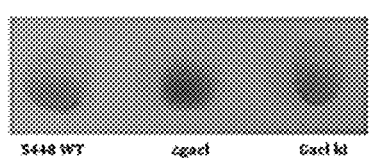

*FIG. 39B*

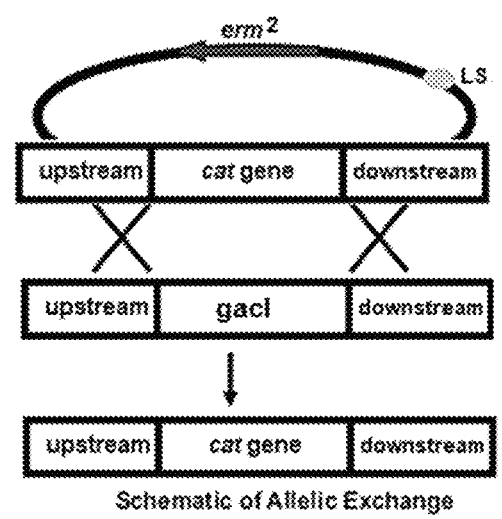

Schematic of Allelic Exchange
*FIG. 39C*

GAC Side Chain Mutant Characterization
sWGA lectin probe (binds to terminal GlcNAc sugar)

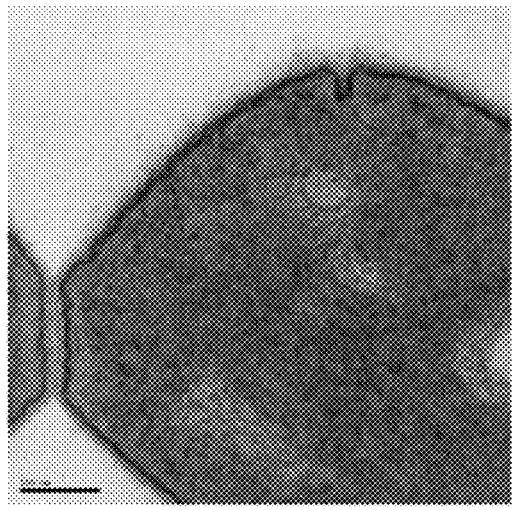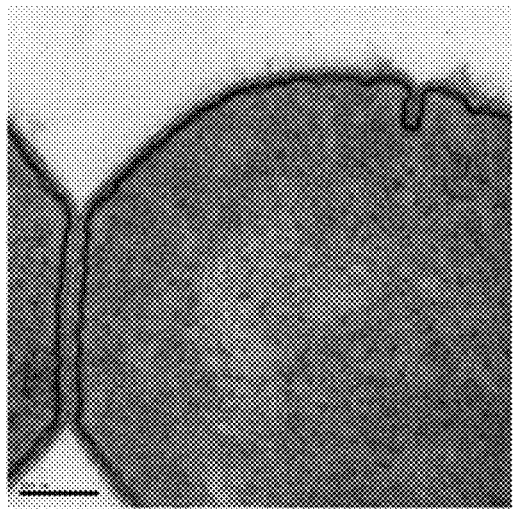
FIG. 44

GAC Side Chain Mutant: No Change in Capsule and Expression of Other Key GAS Virulence Factors

Hyaluronic acid ELISA shows no change in capsule expression. This finding also confirmed by hyaluronic acid binding protein assay (using flow cytometry)

Also confirmed UNCHANGED: M protein expression, beta-hemolysis, Factor H binding, streptokinase activity, surface plasmin acquisition, cysteine protease (SpeB) activity, fibrinogen binding

FIG. 45

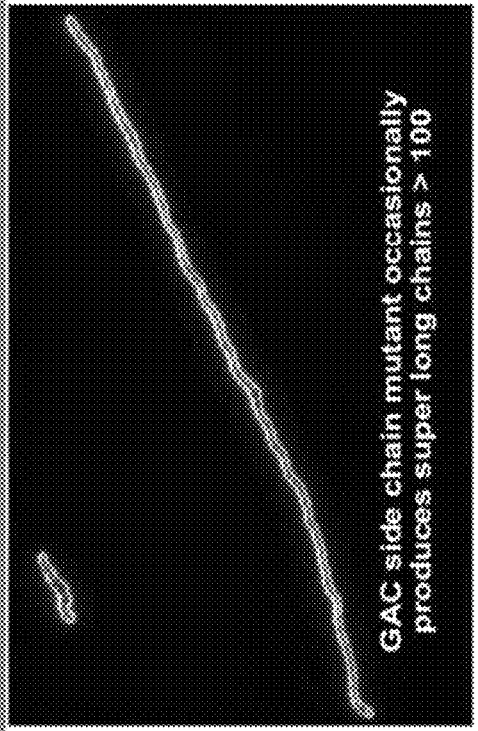
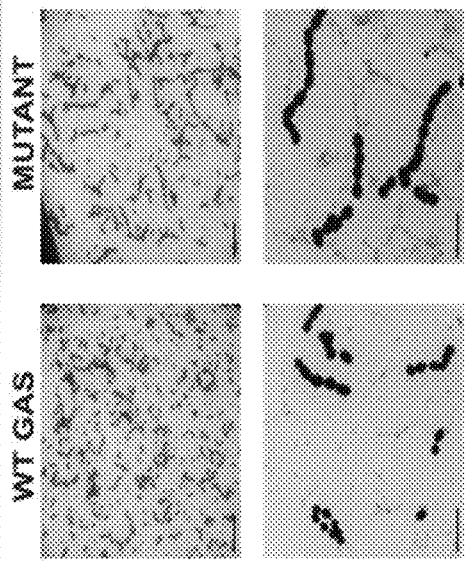
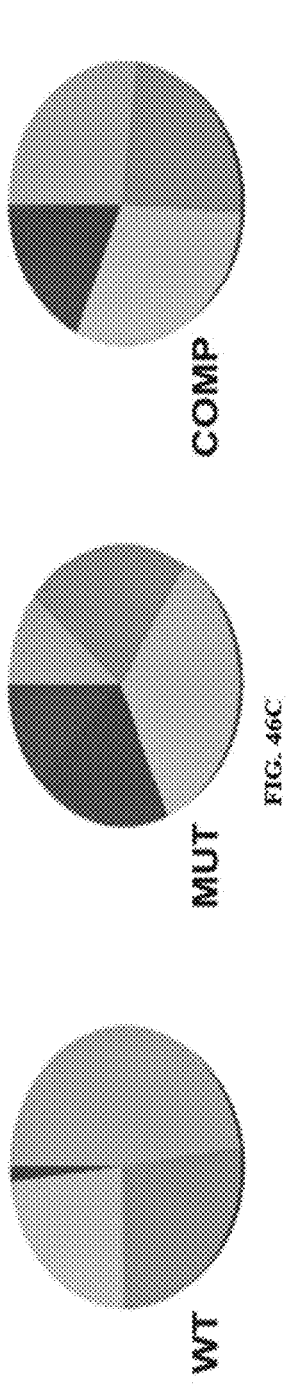
FIG. 46A
FIG. 46B
FIG. 46C

GAC Side Chain Mutant: Changes in Overall Surface Charge and Hydrophobicity

- Surface charge (cytochrome C assay):
  - Cytochrome C is positively charged
  - Mutant binds less Cytochrome C
    → Mutant is less negatively charged

- Hydrophobicity (stationary phase)
  - GAC side chain mutant is more hydrophobic

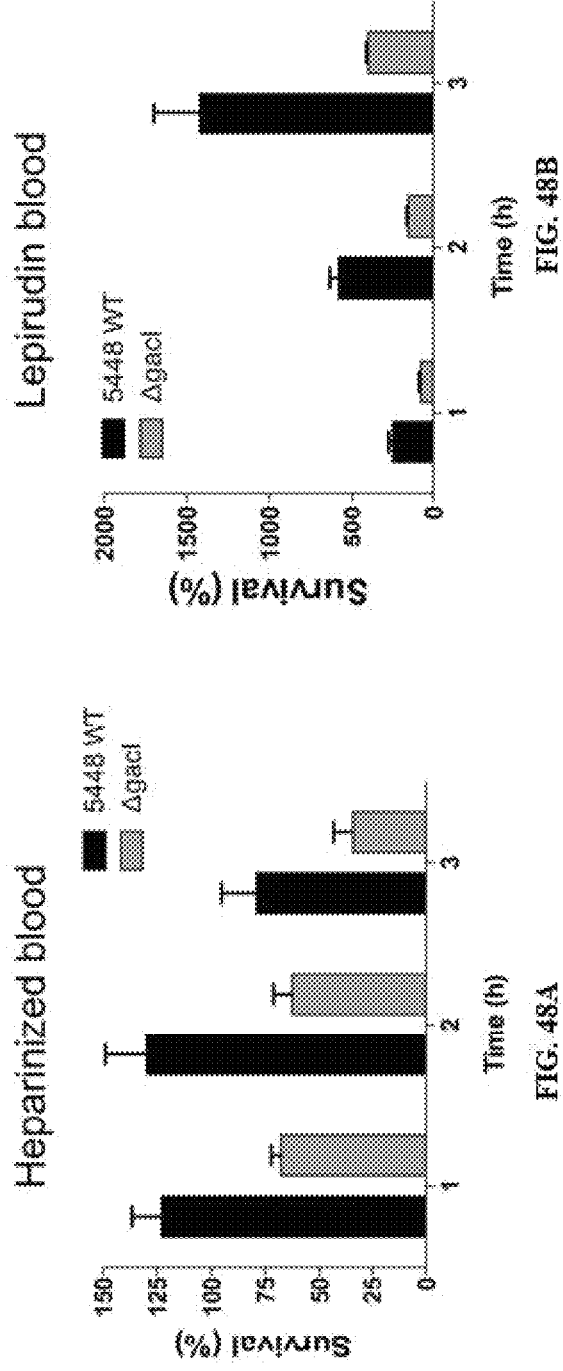

GAC SIDE CHAIN MUTANT ATTENUATED IN RABBIT NECROTIZING PNEUMONIA MODEL

- Bacteria were grown and passed on 5% rabbit blood agar plates
- Rabbits were infected intrabronchially with ~4 x $10^9$ CFU/0.2 ml injection volume
- 3 experiments with a total of 9 rabbits per group

Summary GAC Side Chain Knockout

* Effects of knocking off the Group A carbohydrate GlcNAc side chain:

| Affected | Not affected |
|---|---|
| Surface charge (less negative) | Viability and Growth |
| Hydrophobicity ↑ | H2O2 and Lysosyme susceptibilities |
| Chain length ↑ | Capsule formation |
| Whole blood survival ↓ | Streptokinase & plasmin acquisition |
| Neutrophil & NET resistance ↓ | Switching to AP genotype |
| LL37 susceptibility ↑ | M protein and SpeB expression |
| Vancomicin susceptibility ↓ | Fibrinogen binding |
| Activated platelet susceptibility ↑ | Hemolysis |
| Virulence in rabbits (markedly reduced) | Cell wall morphology by E.M. |
| Virulence in mice (significantly reduced) | |
| Binding to Mab from RF Patient ↓ | |

FIG. 57

Polyclonal Antisera From Rabbit Immunized with a Protein Conjugate of the GAC Mutant Antigen Detect WT GAC and WT GAS Bacteria

| Sample | Specific sera | Sera | Antibody titer | |
|---|---|---|---|---|
| Purified carbohydrate | Mutant purified GACI | Pre-immune | | 1 : 100 |
| | Mutant purified GACI | ΔGACI immunized | Plate #1 | 1 : 12,800 |
| | | | Plate #2 | 1 : 12,800 |
| | WT purified GAC I | Pre-immune | | 1 : 50 |
| | WT purified GAC I | ΔGACI immunized | Plate #1 | 1 : 3,200 |
| | | | Plate #2 | 1 : 3,200 |
| Whole bacteria (heat-killed) | M1 | Pre-immune | | 1 : 3,200 |
| | M1 | ΔGACI immunized | Plate #1 | 1 : 102,400 |
| | | | Plate #2 | 1 : 102,400 |
| | M49 | Pre-immune | | 1 : 400 |
| | M49 | ΔGACI immunized | Plate #1 | 1 : 51,200 |
| | | | Plate #2 | 1 : 51,200 |

FIG. 58

Serum from Rabbits Immunized with Mutant GAC Conjugate Promotes Opsonophagocytosis of WT GAS by Human Neutrophils

Group C Streptococcus (GCS)

- GCS : Gram-positive β-hemolytic cocci, multiple species within this group
  - *Streptococcus equi* subsp. *zooepidemicus*: 67% of proteins similar to proteins in GAS (*hasABC* operon, SLS, *spyCEP* etc) Beres et al. PLoS One, 2008
- Cause of highly contagious upper respiratory tract
- in horses known as strangles.

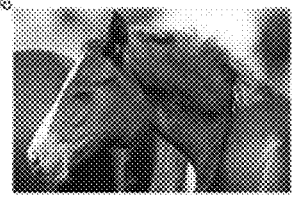

- Also the cause of human infection through zoonotic transmission and unpasteurized milk/milk products
  - meningitis and bacteremia, pharyngitis &poststreptococcal glomerulonephritis

- Group C carbohydrate structure
  Identical backbone to GAS
  Different side chain Rha-(1→2)-α-Rha-(1→3)-α-Rha-(1→2)-
                    ↑
                  GalNAc
                    ↑
                  α-GalNAc

FIG. 62

HETEROLOGOUS EXPRESSION OF SOME GCS ANTIGEN IN GAS M1 BACTERIA

Latex test for GCS carbohydrate

GCS    GAS    GAS +
              3 GCS genes

*FIG. 63A*

GAS

GAS +
3 GCS genes

Fuc    Rha GalNH2 GlcNH2

*FIG. 63B*

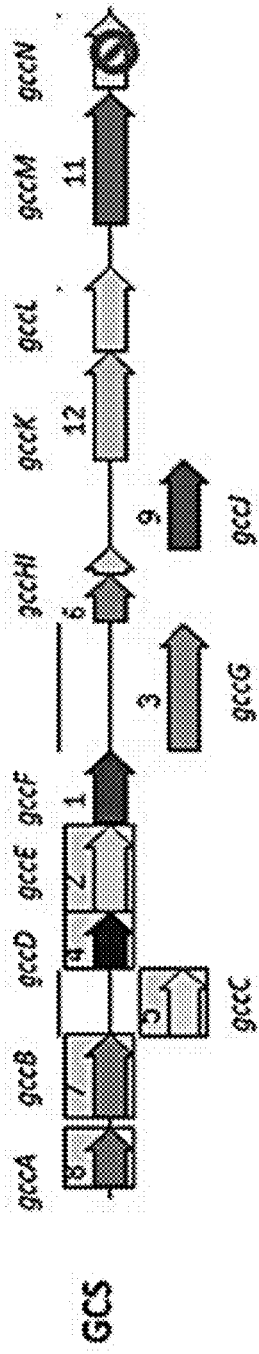
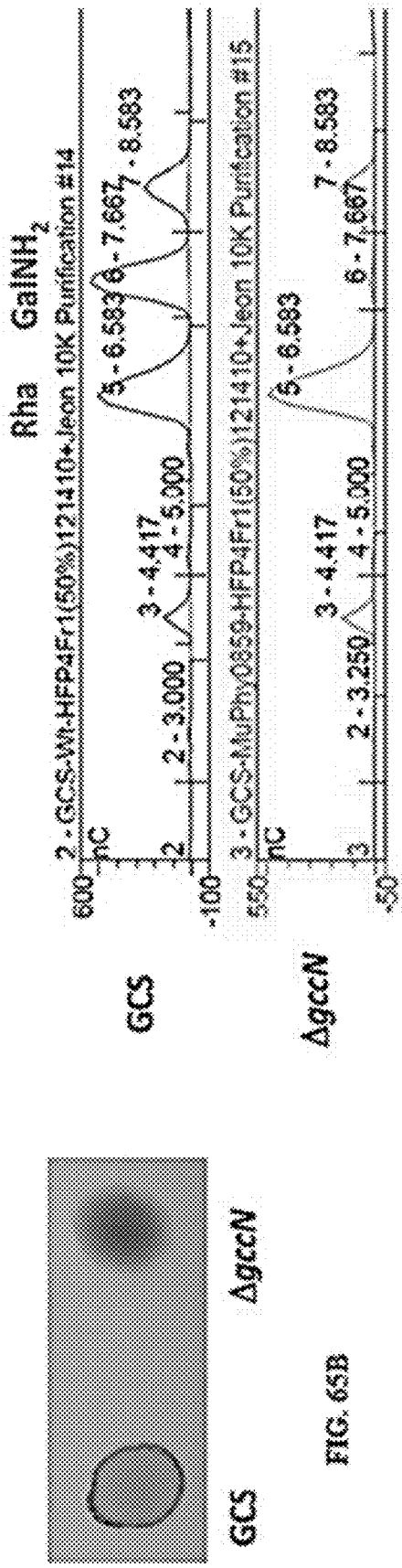
FIG. 65A
- GalE epimerases can convert Glc → Gal and/or GlcNAc → GalNAc
- No GalE epimerase (gccN) is present in GAS 
FIG. 65B
FIG. 65C

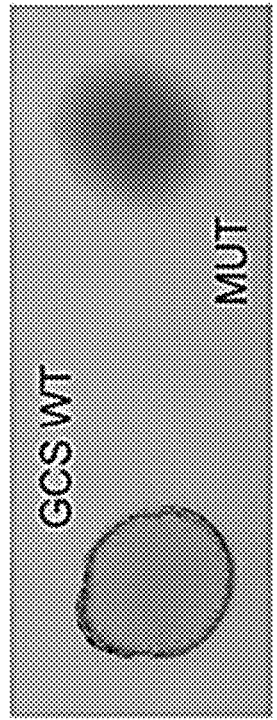
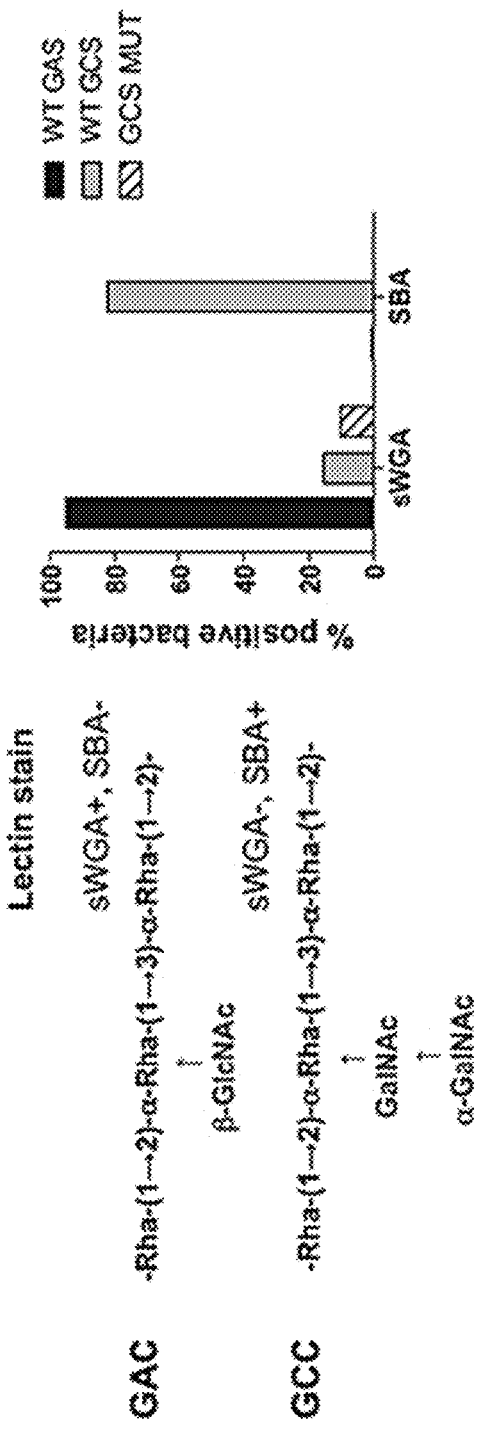
FIG. 66A
FIG. 66B
FIG. 66C

STREPTOCOCCAL GLCNAC-LACKING GLYCOPOLYPEPTIDES, CELL WALL CARBOHYDRATES, *STREPTOCOCCUS* VACCINES, AND METHODS FOR MAKING AND USING THEM

RELATED APPLICATIONS

This application is a continuation of U.S. patent application Ser. No. 15/265,800, filed Sep. 14, 2016, which is a divisional of U.S. patent application Ser. No. 14/237,120, filed Jun. 9, 2014, which application was a national phase application claiming benefit of priority under 35 U.S.C. § 371 to Patent Convention Treaty International Application Serial No: PCT/US2012/049604, filed Aug. 3, 2012, which claims benefit of priority to U.S. Provisional patent Application Ser. No. 61/515,287, filed Aug. 4, 2011. The aforementioned applications are expressly incorporated herein by reference in their entirety and for all purposes.

GOVERNMENT RIGHTS

This invention was made with government support under grants A1077780 and AI060536, awarded by the National Institutes of Health (NIH). The government has certain rights in the invention.

TECHNICAL FIELD

This invention generally relates to medicine, vaccines and microbiology. In particular, in alternative embodiments, the invention provides vaccines, pharmaceutical compounds and formulations for diagnosing, preventing, treating or ameliorating Group A *Streptococcus* (GAS), Group C *Streptococcus* (GCS), or related pathogenic streptococcal, infections. In alternative embodiments, the invention provides compositions such as diagnostic tests, assays, immunoassays and test strips, and methods, for detecting or diagnosing the presence of a Streptococcal infection, e.g., Group A *Streptococcus* (GAS), Group C *Streptococcus* (GCS), or Group A *Streptococcus* (GGS), infections, or other pathogenic *Streptococcus* infections.

BACKGROUND

Group A *Streptococcus* (GAS), also known as *S. pyogenes*, is a preeminent human pathogen ranking among the top 10 infection-related causes of mortality worldwide. GAS causes a wide spectrum of disease, ranging from pharyngitis ("strep throat"), to severe invasive infections including necrotizing fasciitis and toxic shock syndrome, to the autoimmune disorder acute rheumatic fever (ARF). No effective GAS vaccine has been developed, a goal made more challenging by the greater than 150 different serotypes produced by the immunovariable surface M protein.

Group C *Streptococcus* (GCS), although less extensively studied that GAS, can produce human infections quite similar to those caused by GAS, although these are more often opportunistic infections or nosocomial infections. For example, GCS can cause epidemic pharyngitis and cellulitis clinically indistinguishable from GAS disease, and can cause septicemia, endocarditis, septic arthritis and necrotizing infections in patients with predisposing conditions such as diabetes, cancer or advanced aged. GCS is also the cause of the highly contagious and serious upper respiratory tract infection of horses and other equines known as strangles, which is enzootic in a worldwide distribution.

GAS is classically defined by expression of a unique carbohydrate structure called the group A carbohydrate (GAC). Comprising approximately 50% of the dry weight of the bacterial cell wall, GAC consists of a rhamnose backbone and an immunodominant N-acetylglucosamine (GlcNAc) side chain. GAC is the basis for all contemporary rapid diagnostic testing for GAS pharyngitis. GAC has shown potential as a universal GAS vaccine in animal studies, but serious safety concerns were raised since the antibodies against the GlcNAc side chain have been implicated in the immunopathogenesis of rheumatic fever (RF), a poststreptococcal inflammatory disorder of global health importance. In particular, evidence of anti-GlcNAc antibodies have been associated with two cardinal manifestations of RF: rheumatic carditis and Sydenham's chorea.

Group A *Streptococcus* (GAS) mutants with variant group A carbohydrate (GAC), so-called A-variants, have been observed to originate upon serial passage in mice, however the molecular basis for this spontaneous variation has never been documented. In addition, such variants have never been isolated from humans, possibly indicating the GlcNAc side chain is plays an essential role in human colonization, infection or transmission. Human serum contains antibodies against GAC that are predominantly directed against the GlcNAc side chain and promote phagocytosis of GAS. However, anti-GlcNAc antibodies have also been observed to crossreact with human cardiac myosin and lysoganglioside on neuronal cells, associating them to rheumatic carditis and Sydenham chorea, respectively. Anti-GAC antibodies that recognize the rhamnose backbone have also been described to be present in human serum, however, their protective effect against streptococcal infection is currently unknown. Importantly, the identical GAC rhamnose backbone is shared by the group carbohydrate antigens of other medically important pathogens including GCS. GCS are distinguished immunologically from GAS by the expression of a distinct sugar side chain, i.e. two GalNAc residues in GCS vs. the single GlcNAc residue in GAS.

There is currently no universal vaccine available for GAS nor GCS. Historically, experimental GAS vaccines have focused on using the major immunologic epitope, the surface-anchored M protein. This approach is hampered by the existence of more than 150 serotypes based on hypervariability of the M protein N-terminal domain, with evidence that individual M protein vaccines offer only serotype specific protection. In addition, M protein can elicit cross reactive antibodies against myosin and tropomyosin that are believed to be central in the pathogenesis of RF, again raising an important safety issue regarding use of M protein or M protein sequences in vaccine formulations.

SUMMARY

In alternative embodiments, the invention provides isolated, synthetic or recombinant Group A *Streptococcus* (GAS) carbohydrate, glycoprotein or glycoconjugate compositions or variants and/or mutants: partially lacking, substantially lacking, or completely lacking an immunodominant GlcNac side chain; or, partially lacking, substantially lacking, or completely lacking an autoreactive GlcNAc component; or, having a polyrhamnose backbone rather than an immunodominant GlcNac side chain, or a group A carbohydrate (GAC) antigen.

In alternative embodiments, the invention provides isolated, synthetic or recombinant Group C *Streptococcus* (GCS) carbohydrate, glycoprotein or glycoconjugate compositions or variants and/or mutants: partially lacking, substantially lacking, or completely lacking an immunodominant GalNAc-GalNAc side chain; or, partially lacking, substantially lacking, or completely lacking an autoreactive GalNAc-GalNAc component; or, having a polyrhamnose backbone rather than an immunodominant GalNAc-GalNAc side chain, or a group C carbohydrate (GCC) antigen.

In alternative embodiments, the invention provides isolated, synthetic or recombinant Group G *Streptococcus* (GGS) carbohydrate, glycoprotein or glycoconjugate compositions or variants and/or mutants: partially lacking, substantially lacking, or completely lacking an immunodominant glycan side chain; or, partially lacking, substantially lacking, or completely lacking an autoreactive glycan component; or, having a polyrhamnose backbone rather than an immunodominant glycan side chain, or a group G carbohydrate (GGC) antigen.

In alternative embodiments, the invention provides vaccines, formulations, compositions or pharmaceutical compositions, comprising a carbohydrate, glycoconjugate or glycopeptide selected from the group consisting of:

(a) an isolated, synthetic or recombinant Group A *Streptococcus* (GAS) carbohydrate variant/mutant: partially or completely lacking an immunodominant GlcNac side chain; or, partially or completely lacking an autoreactive GlcNAc component; or having a polyrhamnose backbone rather than an immunodominant GlcNac side chain, or a group A carbohydrate (GAC) antigen;

(b) an isolated, synthetic or recombinant Group C *Streptococcus* (GCS) polypeptide or glycopeptide variant/mutant: partially or completely lacking an immunodominant GalNac-GalNac side chain; or, partially or completely lacking a potentially autoreactive GalNac-GalNac component; or having a polyrhamnose backbone rather than an immunodominant GalNac-GalNac side chain, or a group C carbohydrate (GCC) antigen;

(c) an isolated, synthetic or recombinant carbohydrate variant/mutant: partially or completely lacking an immunodominant glycan side chain; or, partially or completely lacking an autoreactive glycan component; or having a polyrhamnose backbone rather than an immunodominant glycan side chain, or an isolated, synthetic or recombinant Group G *Streptococcus* (GGS) carbohydrate variant/mutant: partially or completely lacking an immunodominant glycan side chain; or, partially or completely lacking an autoreactive glycan component; or having a polyrhamnose backbone rather than an immunodominant glycan side chain, or a group G carbohydrate (GGC) antigen, wherein optionally the carbohydrate, glycoconjugate or glycopeptide comprises, or is the same as or is derived from: a pathogenic streptococci of a group B *Streptococcus* (GBS), for example, a *Streptococcus agalactiae*, or a group G *Streptococcus* (GGS) carbohydrate (GCC) antigen (both of which are known to have polyrhamnose backbones similar to that of GAS/GCS, but with more complex antennary structures);

(d) the isolated, synthetic or recombinant carbohydrate variant/mutant of (a) and (b);

(e) the isolated, synthetic or recombinant carbohydrate variant/mutant of (a) and (c);

(f) the isolated, synthetic or recombinant carbohydrate variant/mutant of (b) and (c); and (g) the isolated, synthetic or recombinant carbohydrate variant/mutant of (a), (b) and (c).

In alternative embodiments, the vaccine, formulation, composition or pharmaceutical composition, comprises: a polyrhamnose backbone, or a plurality of polyrhamnose backbones derived from a GAS; GCS; a GBS; a GGS; a GAS and a GCS; a GAS and a GBS; a GAS and a GGS; a GCS and a GBS; a GCS and a GGS; a GBS and a GGS; or a GAS, a GCS, a GBS and a GGS.

In alternative embodiments, the vaccine, formulation, composition or pharmaceutical composition, comprises: an isolated, synthetic or recombinant carbohydrate variant/mutant derived from a GAS; GCS; a GBS; a GGS; a GAS and a GCS; a GAS and a GBS; a GAS and a GGS; a GCS and a GBS; a GCS and a GGS; a GBS and a GGS; or a GAS, a GCS, a GBS and a GGS, wherein the carbohydrate variant/mutant partially or completely lacks an autoreactive glycan component.

In alternative embodiments, the vaccine, formulation, composition or pharmaceutical composition, comprises: an isolated, synthetic or recombinant carbohydrate variant/mutant: partially or completely lacking an immunodominant glycan side chain from: a GAS; GCS; a GBS; a GGS; a GAS and a GCS; a GAS and a GBS; a GAS and a GGS; a GCS and a GBS; a GCS and a GGS; a GBS and a GGS; or a GAS, a GCS, a GBS and a GGS.

In alternative embodiments the vaccines, formulations, compositions or pharmaceutical compositions further comprise one or more (different or additional) GAS, a GCC and/or a GGC protein antigen, or further comprise an adjuvant and/or a pharmaceutically acceptable excipient.

In alternative embodiments the vaccines, formulations, compositions or pharmaceutical compositions of the invention can be manufactured or formulated as a liquid, a powder, a liposome, an aerosol, a nanoparticle or a lyophilized, freeze-dried or cryodessicated preparation, or can be manufactured or formulated as an emulsion, a lyophilized powder, a spray, a cream, a lotion, a controlled release formulation, a tablet, a pill, a gel, a patch, in an implant or in a spray, or is formulated as an aqueous or a non-aqueous isotonic sterile injection solution, or an aqueous or a non-aqueous sterile suspension.

In alternative embodiments the vaccines, formulations, compositions or pharmaceutical compositions of the invention are:

formulated as a liquid, a powder, a liposome, an aerosol, a nanoparticle or a lyophilized, freeze-dried or cryodessicated preparation, formulated as an emulsion, a lyophilized powder, a spray, a cream, a lotion, a controlled release formulation, a tablet, a pill, a gel, a patch, in an implant or in a spray, or is formulated as an aqueous or a non-aqueous isotonic sterile injection solution, or an aqueous or a non-aqueous sterile suspension; or formulated as a vaccine or a pharmaceutical for the prevention, amelioration or treatment of strep throat, impetigo, cellulitis, necrotizing fasciitis, toxic shock syndrome, or post-streptococcal glomerulonephritis.

In alternative embodiments the invention provides isolated, modified or recombinant Group A *Streptococcus* (GAS) engineered or modified:

(a) to lack one or more functional genes necessary to synthesize and/or assemble one or more, or all of its immunodominant GlcNac side chains, or group A carbohydrate (GAC) antigens;

((b) to lack a functional gacI (Spy0610) gene or gene product, or lack any functional copy of the gacI (Spy0610) gene or gene product, wherein optionally the GAS is an allelic replacement knockout of gacI (Spy0610);

(c) such that it cannot assemble a GlcNac side chain; or (d) as in any or all of (a), (b) or (c) and also engineered or modified to lack a functional M protein gene or gene product.

The M protein, along with the immunodominant GlcNac side chain, has been implicated in the immunopathogenesis of rheumatic fever; thus, in one embodiment, the invention provides a double mutant lacking both GlcNac and M protein; this embodiment provides an added safety advantage in manufacture.

In alternative embodiments the invention provides isolated, modified or recombinant Group C *Streptococcus* (GCS) engineered or modified:

(a) to lack one or more functional genes necessary to synthesize and/or assemble one or more, or all of its immunodominant GalNAc-GalNAc side chains, or group G carbohydrate (GCC) antigens;

(b) to lack a functional gene or gene product providing the homologous function to GAS gacI, or lack any functional copy of the this gene or gene product, wherein optionally the GCS is an allelic replacement knockout of the gene encoding the homologous function to GAS gacI;

(c) such that it cannot assemble a GalNAc-GalNAc side chain; or (d) as in any or all of (a), (b) or (c) and also engineered or modified to lack a functional M protein gene or gene product.

In alternative embodiments the invention provides isolated, modified or recombinant Group C *Streptococcus* (GCS) engineered or modified:

(a) to lack one or more functional genes necessary (e.g. gccN) to synthesize and/or assemble one or more, or all of its immunodominant glycan side chains, or group C carbohydrate (GGC) antigens;

(b) to lack a functional gene or gene product, or lack any functional copy of the gene or gene product providing the homologous function to GAS gacI, wherein optionally the GCS mutant is an allelic replacement knockout of this gene; or (c) such that it cannot assemble its glycan side chain on the GCC; or (d) as in any or all of (a), (b) or (c) and also engineered or modified to lack a functional M protein gene or gene product.

In alternative embodiments the invention provides isolated, modified or recombinant Group G *Streptococcus* (GGS) engineered or modified:

(a) to lack one or more functional genes necessary to synthesize and/or assemble one or more, or all of its immunodominant glycan side chains, or group C carbohydrate (GGC) antigens;

(b) to lack a functional gene or gene product, or lack any functional copy of the gene or gene product providing the homologous function to GAS sagI, wherein optionally the GGS mutant is an allelic replacement knockout of this gene; or (c) such that it cannot assemble its glycan side chain on the GGC; or (d) as in any or all of (a), (b) or (c) and also engineered or modified to lack a functional M protein gene or gene product.

In alternative embodiments the invention provides attenuated live bacteria comprising: an isolated, modified or recombinant Group A *Streptococcus* (GAS) of the invention; an isolated, modified or recombinant Group C *Streptococcus* (GCS) of the invention; or, an isolated, modified or recombinant Group G *Streptococcus* (GGS) of the invention.

In alternative embodiments the invention provides vaccines, formulations, compositions or pharmaceutical compositions comprising an attenuated live bacteria of the invention.

In alternative embodiments the invention provides vaccines, formulations, compositions or pharmaceutical compositions comprising: an isolated, modified or recombinant Group A *Streptococcus* (GAS) of the invention; an isolated, modified or recombinant Group G *Streptococcus* (GGS) of the invention; or, an isolated, modified or recombinant Group C *Streptococcus* (GCS) of the invention.

In alternative embodiments the invention provides methods for screening for a composition that can render a Group A *Streptococcus* (GAS) susceptible to innate immune clearance or pharmacological antibiotics comprising:

(a) identifying a composition or a small molecule inhibitor of a gacI (Spy0610) gene expression, or a gacI (Spy0610) gene product function; or (b) identifying a composition or a small molecule inhibitor of any gene or gene product in any of the carbohydrate gene clusters or operons.

In alternative embodiments the invention provides kits comprising: an antibody of the invention; a vaccine, a formulation, a composition or a pharmaceutical composition of the invention; an isolated, synthetic or recombinant Group A *Streptococcus* (GAS) carbohydrate, glycoprotein or glycoconjugate variant/mutant of the invention; an isolated, synthetic or recombinant Group C *Streptococcus* (GCS) carbohydrate, glycoprotein or glycoconjugate variant/mutant of the invention; and/or, an isolated, synthetic or recombinant Group G *Streptococcus* (GGS) carbohydrate, glycoprotein or glycoconjugate variant/mutant of the invention.

In alternative embodiments the invention provides isolated or recombinant antibodies, polyclonal or a monoclonal antibodies, or a serum (e.g., a hyperimmune serum or hyperimmune sera), wherein the antibody or serum or sera specifically react(s) against, or specifically binds to, or is specifically derived against:

(a) a mutant GAS, GGS or GCS carbohydrate antigen, engineered to partially lack, substantially lack or completely lack an immuno-crossreactive carbohydrate side chain, (b) a mutant GAS carbohydrate antigen engineered to partially lack, substantially lack or completely lack an immuno-crossreactive GlcNac side chain; or (c) a mutant GCS carbohydrate antigen engineered to partially lack, substantially lack or completely lack an immunodominant GalNac-GalNac side chain.

In alternative embodiments, the antibody or serum is formulated for active or passive immunotherapy in a mammal, optionally formulated for treating, ameliorating or for preventing a GAS, GGS or GCS infection in a mammal, a human or a horse, wherein optionally the immunotherapy is for the prevention, amelioration or treatment of strep throat, impetigo, cellulitis, necrotizing fascitis, toxic shock syndrome, or post-streptococcal glomerulonephritis.

In alternative embodiments the invention provides vaccines or formulations comprising one or more isolated or recombinant antibodies, a polyclonal or a monoclonal antibodies, or a sera (e.g., a hyperimmune sera) of the invention, wherein the antibodies or sera specifically react against, or specifically bind to, or are specifically derived against one, two or all of:

(a) a mutant GAS, GGS or GCS carbohydrate antigen, engineered to partially lack, substantially lack or completely lack an immuno-crossreactive carbohydrate side chain, (b) a mutant GAS carbohydrate antigen engineered to partially lack, substantially lack or completely lack an immuno-crossreactive GlcNac side chain; and/or (c) a mutant GCS carbohydrate antigen engineered to partially lack, substantially lack or completely lack an immunodominant GalNac-GalNac side chain.

In alternative embodiments the invention provides methods for active or passive immunotherapy in a mammal for preventing a GAS, a GGS or a GCS infection in a mammal, a human or a horse, comprising:

(a) providing the isolated or recombinant antibody, polyclonal or a monoclonal antibody, or a serum or a hyperimmune serum of the invention, or a vaccine or formulation of the invention; and (b) administering a therapeutically or prophylactically effective dose or dosages of the isolated or recombinant antibody, polyclonal or a monoclonal antibody, or a serum or a hyperimmune serum, or vaccine or formulation, to the mammal, a human or a horse, wherein optionally the immunotherapy is for the prevention, amelioration or treatment of strep throat, impetigo, cellulitis, necrotizing fascititis, toxic shock syndrome, or post-streptococcal glomerulonephritis.

In alternative embodiments the invention provides diagnostic tests, assays, immunoassays or test strips, or arrays, microarrays, biochips, diagnostic chips or chips, for detecting or diagnosing the presence of a Streptococcal infection, comprising the isolated or recombinant antibody, polyclonal or a monoclonal antibody, or a serum or a hyperimmune serum of the invention, or a vaccine or formulation of the invention, wherein optionally the diagnostic test, assay, immunoassay or test strip detects the presence of or diagnoses a Streptococcal pharyngitis ("strep throat") in a human, wherein optionally the diagnostic test, assay, immunoassay or test strip, or array, microarray, biochip, diagnostic chip or chip, detects the presence of or diagnoses a strep throat, impetigo, cellulitis, necrotizing fascititis, toxic shock syndrome, or post-streptococcal glomerulonephritis, wherein optionally the diagnostic test, assay, immunoassay or test strip detects the presence of or diagnoses a Streptococcal infection, wherein optionally the Streptococcal infection is a GAS, a GGS or a GCS infection in a mammal.

In alternative embodiments, the diagnostic test, assay, immunoassay or test strip comprises a latex agglutination, enzyme immunoassay or an optical immunoassay.

In alternative embodiments the invention provides methods for detecting the presence of or diagnosing a Streptococcal infection, or a Streptococcal pharyngitis ("strep throat") in a human, comprising use of a diagnostic test, assay, immunoassay or test strip, latex agglutination assay, enzyme immunoassay or optical immunoassay of the invention, wherein optionally the infection is or involves a strep throat, impetigo, cellulitis, necrotizing fascititis, toxic shock syndrome, or post-streptococcal glomerulonephritis.

Thus, in alternative embodiments, the invention provides a diagnostic test, assay or test strip (e.g., latex agglutination, enzyme immunoassay, or optical immunoassay) for detecting the presence of or diagnosing a Streptococcal infection, or a streptococcal pharyngitis ("strep throat") in a mammal, e.g., a human. In alternative embodiments, the diagnostic test, assay or test strip is rapid and/or has improved sensitivity and/or specificity to as compared to current technologies since it targets a bacterial specific motif (polyrhamnose) rather than a common sugar motif (e.g., a GlcNac or a GlcNac) present on mammalian (e.g., human) cells and mucosal secretions. Since an identical polyrhamnose backbone is shared by GAS and GCS, in alternative embodiments these rapid diagnostic tests and assays have the advantage of identifying both species lacking in current rapid diagnostic methodologies.

In alternative embodiments the invention provides diagnostic tests, assays, immunoassays, test strips, beads or latex beads, arrays, microarrays, biochips, diagnostic chips or chips, or gels or hydrogels, or magnetic particles, for detecting or diagnosing the presence of a Streptococcal infection, comprising (or having affixed or attached thereon) the isolated or recombinant antibody, polyclonal or a monoclonal antibody, or serum or hyperimmune serum of the invention, or a vaccine or formulation of the invention, wherein optionally the diagnostic tests, assays, immunoassays, test strips, beads or latex beads, arrays, microarrays, biochips, diagnostic chips or chips, or gels or hydrogels, or magnetic particles, detect the presence of or diagnoses a Streptococcal pharyngitis ("strep throat"), impetigo, cellulitis, necrotizing fascititis, toxic shock syndrome, or post-streptococcal glomerulonephritis, in a human, wherein optionally the diagnostic tests, assays, immunoassays, test strips, beads or latex beads, arrays, microarrays, biochips, diagnostic chips or chips, or gels or hydrogels, or magnetic particles, detect the presence of or diagnoses a Streptococcal infection, wherein optionally the Streptococcal infection is a GAS, a GGS or a GCS infection in a mammal.

In alternative embodiments the invention provides hydrogels, particles or magnetic particles for detecting or diagnosing the presence of a Streptococcal infection, comprising (or having affixed or attached thereon) the isolated or recombinant antibody, polyclonal or a monoclonal antibody, or serum or hyperimmune serum of the invention, or a vaccine or formulation of the invention, wherein optionally the hydrogel, particle or magnetic particle detects the presence of or diagnoses a Streptococcal pharyngitis ("strep throat"), impetigo, cellulitis, necrotizing fascititis, toxic shock syndrome, or post-streptococcal glomerulonephritis, in a human, wherein optionally the hydrogel, particle or magnetic particle detects the presence of or diagnoses a Streptococcal infection, wherein optionally the Streptococcal infection is a GAS, a GGS or a GCS infection in a mammal.

In alternative embodiments the invention provides arrays, microarrays, biochips, diagnostic chips or chips, for detecting or diagnosing the presence of a Streptococcal infection, comprising (or having affixed or attached thereon) the isolated or recombinant antibody, polyclonal or a monoclonal antibody, or serum or hyperimmune serum of the invention, or a vaccine or formulation of the invention, wherein optionally the biochip, diagnostic chip or chip detects the presence of or diagnoses a Streptococcal pharyngitis ("strep throat"), impetigo, cellulitis, necrotizing fascititis, toxic shock syndrome, or post-streptococcal glomerulonephritis, in a human, wherein optionally the diagnostic test, assay, immunoassay or test strip detects the presence of or diagnoses a Streptococcal infection, wherein optionally the Streptococcal infection is a GAS, a GGS or a GCS infection in a mammal.

In alternative embodiments the invention provides uses of: an isolated, synthetic or recombinant Group A *Streptococcus* (GAS) carbohydrate, glycoprotein or glycoconjugate variant/mutant, an isolated, synthetic or recombinant Group C *Streptococcus* (GCS) carbohydrate, glycoprotein or glycoconjugate variant/mutant, or an isolated, synthetic or recombinant Group G *Streptococcus* (GGS) carbohydrate, glycoprotein or glycoconjugate variant/mutant, or an isolated or a recombinant antibody, polyclonal or a monoclonal antibody, or a serum or a hyperimmune serum, or a vaccine or formulation, for the manufacture of a pharmaceutical or a medicament, wherein optionally the isolated, synthetic or recombinant GAS, GCS and/or GGS is used for the manufacture of a pharmaceutical or a medicament to treat, prevent or ameliorate a Streptococcal infection, a Streptococcal pharyngitis ("strep throat"), impetigo, cellulitis, necrotizing fascititis, toxic shock syndrome, or post-streptococcal glomerulonephritis.

In alternative embodiments the invention provides an isolated, synthetic or recombinant Group A *Streptococcus* (GAS) carbohydrate, glycoprotein or glycoconjugate variant/mutant of the invention, an isolated, synthetic or recombinant Group C *Streptococcus* (GCS) carbohydrate, glycoprotein or glycoconjugate variant/mutant of the invention, or an isolated, synthetic or recombinant Group G *Streptococcus* (GGS) carbohydrate, glycoprotein or glycoconjugate variant/mutant of the invention, or an isolated or a recombinant antibody, polyclonal or a monoclonal antibody, or a serum or a hyperimmune serum of the invention, or a vaccine or formulation of the invention, for use in a method of treating a Streptococcal infection, a Streptococcal pharyngitis ("strep throat"), impetigo, cellulitis, necrotizing fascititis, toxic shock syndrome, or post-streptococcal glomerulonephritis.

The details of one or more embodiments of the invention are set forth in the accompanying drawings and the description below. Other features, objects, and advantages of the invention will be apparent from the description and drawings, and from the claims.

All publications, patents, patent applications cited herein are hereby expressly incorporated by reference for all purposes.

BRIEF DESCRIPTION OF THE DRAWINGS

The drawings set forth herein are illustrative of embodiments of the invention and are not meant to limit the scope of the invention as encompassed by the claims.

FIG. 3 illustrates information regarding types of mucosal and invasive infections associated with the leading human pathogen GAS, or Group A *Streptococcus*, including strep throat, impetigo, cellulitis, necrotizing fascititis, toxic shock syndrome, post-streptococcal glomerulonephritis, that can be treated, ameliorated or prevented using compositions of the invention, e.g., vaccine and antibodies or the invention; or that can be diagnosed using compositions, e.g., devices of the invention such as test strips or immunoassays, of the invention.

FIG. 5A schematically illustrates the chemical structure of group A streptococcal cell wall carbohydrate antigen (GAC), and FIG. 5B illustrates an electron microscopic appearance or image of the group A streptococcal cell wall carbohydrate antigen (GAC), with its polyrhamnose backbone and GlcNAc side chain.

FIG. 6A-B illustrates an electron microscopic appearance or image of GAS (FIG. 6A) and variant GAS (FIG. 6B) strains that lose immune reactivity to the GlcNAc side chain (stained with ferritin conjugated Group A antibodies)—so called "A variant strains", isolated from mice on serial passage.

FIG. 7 graphically illustrates data from a latex agglutination test on the natural antibody response to the group A carbohydrate and use of the WT GlcNAc-containing carbohydrate as a vaccine antigen.

FIG. 8 schematically illustrates the twelve-gene locus encoding the biosynthetic machinery for the group A streptococcal (GAS) cell wall carbohydrate antigen, as discussed in Example 1, below.

FIG. 9A illustrates a gel of a restriction digest of a PCR amplification of the mutant GAC GlcNAc-deficient knockout mutant, the PCR analysis shows absence of the gacI gene in the knockout mutant;

FIG. 9B illustrates an image of a latex agglutination for group A carbohydrate (GlcNac side chain) showing it is no longer reactive in the GAS ΔgacI mutant;

FIG. 9C schematically illustrates or diagrams an exemplary method for generation of GAC GlcNAc-deficient knockout mutant through allelic replacement of the gacI gene.

FIG. 10A graphically illustrates data showing that the wild type (WT) parent M1 GAS strain and the isogenic ΔgacI mutant show similar growth kinetics in bacteriologic growth media (Todd-Hewitt Broth);

FIG. 10B graphically illustrates data showing an analysis of the wild-type GAS strain demonstrating binding of the sWGA lectin probe, specific for terminal GlcNac sugars to the bacterial surface; this binding is lost in the ΔgacI mutant, and the results confirms loss of the GlcNac side chain in the mutant.

FIG. 11A-B graphically illustrates data from a cytochrome C binding assay indicating that the ΔgacI mutant expresses less negative surface charge than the WT parent M1 GAS strain in both stationary and exponential growth phases. (B) graphically illustrates data from a N-hexadecane partition analysis indicating that the ΔgacI mutant is more hydrophobic than the WT parent M1 GAS strain.

FIG. 12 graphically illustrates SpeB activity in supernatant demonstrating that levels of cysteine protease (SpeB) activity are similar in the WT GAS M1T1 parent strain and the isogenic ΔgacI mutant.

FIG. 13 graphically illustrates data of a hyaluronic acid ELISA, showing that the WT parent M1 GAS strain and the isogenic ΔgacI mutant express similar levels of hyaluronic acid capsule; animal passage increases hyaluronic acid expression in M1 GAS (by selection of covS mutants); a similar increase is seen in both the WT parent strain and the isogenic ΔgacI mutant.

FIG. 23A schematically illustrates the classical complement pathway and the lectin pathway; and FIGS. 23B and 23C graphically illustrate that data from a serum survival assay showing that C4b (upstream) complement deposition (FIG. 23B) and C5B-9 complement deposition (FIG. 23C) is reduced in the ΔgacI mutant (reduced in the absence of GAC side chain) compared to the WT parent GAS strain.

FIG. 25 is a summary of some phenotypic characteristics and virulence properties that are changed or unaffected when comparing the WT GAS M1T1 strain to the isogenic ΔgacI mutant lacking the GlcNAc side chain on its cell wall carbohydrate antigen.

FIG. 26 schematically illustrates the structure of the Group C streptococcal cell wall carbohydrate (GCC), and a description of its association with human and equine infectious diseases, as discussed in Example 1.

FIG. 34 illustrates the results of a latex bead test showing that heterologous expression of the gccL-N genes from GCS into GAS causes incorporation of GlcNAc-GlcNAc side chain, as shown by latex agglutination test.

FIG. 38 schematically illustrates the twelve-gene locus encoding the biosynthetic machinery for the group A streptococcal (GAS) cell wall carbohydrate antigen, as discussed in Example 1.

FIG. 39A-C illustrates targeted knockout of the gacI gene in M1 GAS strain 5448 by allelic exchange mutagenesis; FIG. 39A illustrates a PCR analysis showing the absence of the gacI gene in the knockout mutant; FIG. 39B illustrates a latex agglutination for group A carbohydrate (GlcNac side chain) is no longer reactive in the GAS ΔgacI mutant; and FIG. 39C schematically illustrates how if a copy of the gacI gene is knocked back into the mutant, the reactivity for the GlcNac is restored.

FIG. 44 illustrates a transmission electron microscopy image showing that the WT parent M1 GAS strain and the isogenic ΔgacI mutant show ultrastructural appearance under transmission electron microscopy.

FIG. 45 graphically illustrates that the WT parent M1 GAS strain and the isogenic ΔgacI mutant express similar levels of hyaluronic acid capsule, as discussed in Example 1.

FIGS. 46A and 46B illustrate images showing that the ΔgacI mutant tends to express longer chain length than the WT parent M1 GAS strain; and FIG. 46C graphically illustrates these results.

FIGS. 48A and 48B graphically illustrate that the ΔgacI mutant survives less well than the WT parent M1 GAS strain in freshly isolated human whole blood, whether heparin (FIG. 48A) or lepirudin (FIG. 48B) is used for anticoagulation; the results indicate the GlcNAc side chain contributes to whole blood survival.

FIG. 57 is a summary of phenotypic characteristics and virulence properties that are changed or unaffected when comparing the WT GAS M1T1 strain to the isogenic ΔgacI mutant lacking the GlcNAc side chain on its cell wall carbohydrate antigen.

FIG. 58 summarizes data showing that polyclonal antisera from rabbit immunized with a protein conjugate of the GAC mutant antigen detect WT GAC and WT GAS bacteria, as discussed in Example 1.

FIG. 62 schematically illustrates the structure of the Group C streptococcal cell wall carbohydrate (GCC) and provides a description of its association with human and equine infectious diseases, as discussed in Example 1.

FIG. 63A illustrates a slide showing that if genes from the group C streptococcal operon encoding its group carbohydrate are cloned into group A *Streptococcus*, evidence of some GalNAc side chain incorporation into the GAS antigen can be demonstrated;

FIG. 63B illustrates GalNAc side chain incorporation into the GAS antigen, as discussed in Example 1.

FIG. 65A schematically illustrates how GCS epimerase gccN is required for GCC side chain formation, where GalE epimerases can convert Glc to Gal, and/or GlcNAc to GalNAc, and that no GalE epimerase gccN is present in GAS; and FIG. 65B and FIG. 65C illustrate data showing that GCS epimerase gccN is required for GCC side chain formation, as discussed in Example 1.

FIGS. 66A, 66B and 66C schematically illustrate that knockout of the GCS gccN gene yields a ΔgccN mutant lacking the GalNAc-GalNAc side chain, as confirmed by loss of binding to SBA, a lectin recognizing GalNAc; where FIG. 66A illustrates a latex bead test showing loss of binding by a ΔgccN mutant lacking the GalNAc-GalNAc side chain, and FIG. 66C graphically illustrates loss of binding to SBA by a ΔgccN mutant lacking the GalNAc-GalNAc side chain.

Like reference symbols in the various drawings indicate like elements.

Figure 1A:
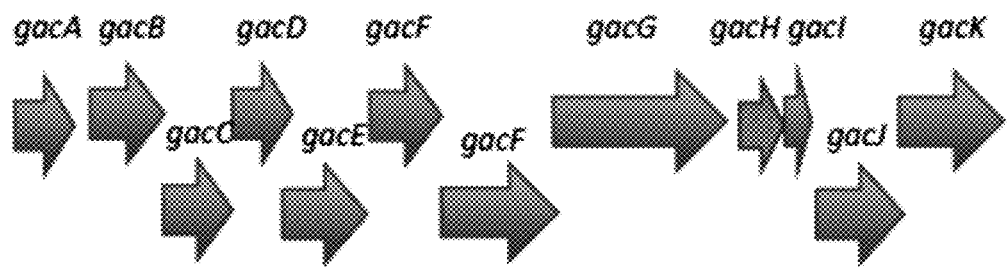
FIG. 1A schematically illustrates the genetic operon for assembling the GAC in GAS through bioinformatics analysis, and shows the twelve-gene locus encoding the biosynthetic machinery for the group A streptococcal (GAS) cell wall carbohydrate antigen.

Reference will now be made in detail to various exemplary embodiments of the invention, examples of which are illustrated in the accompanying drawings. The following detailed description is provided to give the reader a better understanding of certain details of aspects and embodiments of the invention, and should not be interpreted as a limitation on the scope of the invention.

DETAILED DESCRIPTION

In alternative embodiments, the invention provides a Group A *Streptococcus* (GAS) cell wall carbohydrate (GAC) variant lacking all of its immunodominant GlcNac side chains. In alternative embodiments, the invention provides a Group A *Streptococcus* (GAS) genetically modified such that it cannot express one or more, or all (e.g., cannot express any) of its immunodominant GlcNac side chains on its cell wall group A carbohydrate (GAC) antigens.

Genetic information described herein and the unique mutants we have generated in this invention can serve as a tool to purify a mutant GAC lacking the GlcNAc side that could be used as a universal vaccine antigen against all GAS/GCS/GGS strains and at the same time be devoid of the risk for autoimmune complications.

In alternative embodiments these modified GAS bacteria of the invention lack one or more genes necessary to synthesize and/or assemble one or more, or all of its immunodominant group A GlcNac side chains, or group A carbohydrate (GAC) antigens.

The 12 genes that we have discovered constitute the GAC biosynthesis gene cluster are hereafter designated gacA-gacI, corresponding to Spy0602 to Spy0613 in the published M5005 GAS genome. The 9th gene of this operon, gacI (Spy0610), encodes the enzymatic function required for addition of the GlcNac side chain to the polyrhamnose backbone of the GAC. Thus in one embodiment, modified bacteria lack the gacI gene or lack a functional gacI gene or gene product, and therefore express a mutant GAC lacking the GlcNac side chain, also known as an "A-variant GAC". Thus, in one embodiment, modified bacteria of the invention lack the gacI (or Spy0610) gene or lack a functional gacI (or Spy0610 gene).

In alternative embodiments, the invention provides Group A *Streptococcus* (GAS) polypeptide or glycopeptide variants that have a polyrhamnose backbone (an "A-variant GAC") rather than an immunodominant GlcNac side chain, or a group A carbohydrate (GAC) antigen. In alternative embodiments, the invention provides a Group A *Streptococcus* (GAS) genetically modified such that it expresses a Group A *Streptococcus* (GAS) carbohydrate variant that has a polyrhamnose backbone (an "A-variant GAC") rather than an immunodominant GlcNac side chain, or a group A carbohydrate (GAC) antigen.

We have generated an allelic replacement knockout of gacI (Spy0610) in GAS parent strain 5448, representative of the globally disseminated, highly virulent M1T1 GAS clone that has emerged as the leading cause of both pharyngitis and severe invasive disease for the last 20 to 30 years. These genetically modified bacteria of this invention comprise an engineered mutation in the GAC lacking specifically the Glc-Nac side chain; and this bacteria of the invention can be used to purify (can be used as a source of) high-molecular weight, intact polyrhamnose backbone (A-variant GAC) for use as a safe vaccine antigen, e.g., formulated as a protein conjugate.

Provided herein is definitive proof of principle of the utility of the modified antigens of the invention as a vaccine. Polyclonal antisera raised in a rabbit to the mutant GAC (isolated from the isogenic ΔgacI mutant) shows a high titer against both the mutant GAC and the wild-type GAC (i.e. the antibodies are able to recognize the underlying backbone even in the presence of the native side chain). Moreover, the immune sera recognize equally wild-type group A *Streptococcus* from the M1 serotype and M49 serotype, showing cross-protection that implies the potential for universal reactivity against all GAS and GCS. Finally, the immune sera are able to substantially promote opsono-phagocytic killing of both M1 and M49 GAS by human neutrophils and in human whole blood, confirming the utility of the vaccine compositions of the invention and this vaccine strategy in prevention of invasive GAS infection.

Thus, in alternative embodiments the invention provides bacterial carbohydrates that will allow mammals, including humans, to make antibodies that provide protection against all strains of GAS, GCS and GGS without generation of antibodies to side chain carbohydrates which may cross react with host tissues. The Glc-Nac side chain epitope, which carbohydrates and conjugate vaccines of the invention lack, is implicated in the immunopathogenesis of rheumatic carditis/Sydenham's chorea—a potential prohibitive safety concern for a vaccine. Our research confirms the validity of this concern, as we found that a monoclonal antibody derived from the blood of a patient with rheumatic carditis, previously shown to cross-react with both human cardiac tissue and GAS, binds to our wild-type parent GAS strain but not to the isogenic gacI mutant lacking GlcNac.

Using bioinformatic and molecular genetics approaches, we have discovered the genetic locus responsible for assembling the group A carbohydrate (or GAC) antigen. Using bioinformatic and molecular genetic approaches, we have discovered the 12-gene locus (which we have named gacA-gacL) responsible for assembling GAC antigen and the corresponding homologous operons in GCS and GGS. By knocking out a specific gene Spy0610, we generated the first-ever viable Group A *Streptococcus* (GAS) mutant that expresses a GAC completely devoid of the immunodominant GlcNac side chain, as confirmed by detailed glycoanalysis. Thus, in alternative embodiments, the invention provides a Group A *Streptococcus* (GAS), variant/mutant carbohydrate that lacks an immunodominant GlcNac side chain, i.e., that lacks the autoreactive GlcNAc component; and *Streptococcus* GGS and/or GCS variant/mutant carbohydrates that lack (GalNAc)$_2$ or a combination of GalNAc/GlcNAc, respectively (side chains on the GCC and GGC are not GlcNAc but (GalNAc)$_2$ or probably a combination of GalNAc/GlcNAc, respectively). In one embodiment, the invention provides *Streptococcus* (GAS) variants/mutants that lack a functional gacI (Spy0610 gene), or cannot express the Spy0610 gene product. In one embodiment, the invention provides *Streptococcus* (GAS) variants/mutants that expresses a Group A *Streptococcus* (GAS) variant/mutant that lacks an immunodominant GlcNac side chain, i.e., that lacks the autoreactive GlcNAc component.

Interestingly, the GAC rhamnose backbone is shared by the group carbohydrate antigens of other medically important pathogens including groups C and G *Streptococcus* (GCS, GGS), each of which expresses a different unique sugar side chain. Therefore, the genetic mutant of this invention can serve as a unique tool to purify a mutant GAC lacking the GlcNAc side that could be used as a universal GAS/GCS/GGS vaccine antigen devoid of risk for autoimmune complications.

In one embodiment, the invention provides compositions (e.g., vaccines) and methods for immunizing with an A-variant carbohydrate purified from the gacI (Spy0610) mutant GAS strain of the invention to induce anti-GAC antibodies that are protective against all serotypes of GAS but lack the that autoreactive GlcNAc component. In alternative embodiments, this vaccine of the invention protects against GCS infection, which has an identical underlying polyrhamnose backbone, also protects against other streptococcal species such as GBS and GGS, which have similar underlying rhamnose backbone in their group carbohydrate structures.

In one embodiment, an A-variant carbohydrate of the invention is used in combination vaccines with other GAS protein antigens, or standard techniques could be used to knock out the M protein in an exemplary mutant of this invention, creating a potential whole cell or live attenuated vaccine strain lacking both antigens (GAC and M protein) implicated in rheumatic fever pathogenesis.

Finally, the enzyme encoded by gacI (Spy0610) is responsible for the addition of the GlcNac side chain to the GAC, and we have shown the GAC is a virulence factor of the pathogen. Compared to the wild-type parent strain, the GAS ΔgacI knockout mutant lacking the GAC side chain is markedly attenuated in both mouse and rabbit models of invasive GAS infection. Compared to the wild-type parent strain, the GAS ΔgacI knockout mutant is much more sensitive to killing by human whole blood, human serum, and baby rabbit serum. Compared to the wild-type parent strain, the GAS ΔgacI knockout mutant is much more sensitive to killing by the human cathelicidin antimicrobial peptide LL-37 and antimicrobial peptides derived from activated human platelets, a critical element of host innate immunity produced on epithelial cell surfaces and by circulating and tissue-based immune cells including neutrophils, macrophages and mast cells. Thus the GAS ΔgacI mutant is more susceptible to immune clearance in a wide array of in vitro, tissue culture and in vivo model systems. A screen to identify small molecule inhibitors of gacI (Spy0610) could identify novel therapeutics for treatment of serious GAS infections, by rendering the pathogen susceptible host innate immune clearance.

Because the GAC compromises 50% of the bacterial cell wall and because our experimental data suggests that targeting many of the other genes in the operon is lethal to the pathogen, we conclude that the GAC polyrhamnose backbone itself is essential for viability of GAS. Thus this invention concludes that screening for small molecule inhibitors for enzymes each of the other candidate enzymes and transport proteinsin the GAC operon (gacA, gacB, gacC, gacD, gacE, gacF, gacG, gacH, gacJ, gacK) or corresponding genes in the GCC operon would identify novel antibiotic agents with bactericidal (lethal) activity against GAS and GCS for direct development as antibiotic agents.

We have discovered the genetic operon for assembling the GAC in GAS through bioinformatics analysis. We have generated a viable allelic exchange GAS mutant, called ΔgacI, expresses a mutated GAC. Purification of this mutant GAC carbohydrate has been performed and glycoanalysis has unambiguously demonstrated the absence of GlcNAc side chain.

Products of Manufacture, Kits

The invention also provides products of manufacture (e.g., cells, carbohydrates, glycoconjugates), kits and pharmaceuticals (a pharmaceutical composition or a formulation or a vaccine) for practicing the methods of this invention. In alternative embodiments, the invention provides products of manufacture, kits and/or pharmaceuticals comprising all the components needed to practice a method of the invention. In alternative embodiments, the products of manufacture, kits and/or pharmaceuticals further comprises instructions for practicing the methods of the invention.

Vaccines, Formulations and Pharmaceutical Compositions

In alternative embodiments, the invention provides vaccines, pharmaceutical formulations and compositions to treat, prevent or ameliorate Group A *Streptococcus* (GAS), Group C *Streptococcus* (GCS) and/or Group G *Streptococcus* (GGS) infections, and other pathogenic streptococci bearing similar polyrhamnose backbones in their cell wall carbohydrate. These include the genetically engineered polyrhamnose backbone GAC lacking the GlcNac side chain, for use as a vaccine antigen alone, conjugated to a protein carrier, or as a component of a multiple antigen subunit vaccine. In alternative embodiments, the invention provides GAS strains with engineered deletion of gacI, or GCS mutants with an engineered deletion of gccN, alone or in combination with other virulence factor mutations, that can serve as a whole cell or live-attenuated vaccine strain(s) for protection against GAS, GCS and GGS infection.

In alternative embodiments, the vaccines, solutions, formulations or pharmaceutical compositions of the invention can be administered parenterally, topically, intranasally, intramuscularly, subcutaneously, intradermally, orally or by local administration, such as by aerosol or transdermally. The pharmaceutical compositions can be formulated in any way and can be administered in a variety of unit dosage forms depending upon the condition or disease and the degree of illness, the general medical condition of each patient, the resulting preferred method of administration and the like. Details on techniques for formulation and administration are well described in the scientific and patent literature, see, e.g., the latest edition of *Remington's Pharmaceutical Sciences*, Maack Publishing Co., Easton Pa. ("Remington's"). For example, in alternative embodiments, these compositions of the invention are formulated in a buffer, in a saline solution, in a powder, an emulsion, in a vesicle, in a liposome, in a nanoparticle, in a nanolipoparticle and the like. In alternative embodiments, the compositions can be formulated in any way and can be applied in a variety of concentrations and forms depending on the desired in vivo, in vitro or ex vivo conditions, a desired in vivo, in vitro or ex vivo method of administration and the like. Details on techniques for in vivo, in vitro or ex vivo formulations and administrations are well described in the scientific and patent literature. Formulations and/or carriers used to practice this invention can be in forms such as tablets, pills, powders, capsules, liquids, gels, syrups, slurries, suspensions, etc., suitable for in vivo, in vitro or ex vivo applications.

In practicing this invention, the compounds (e.g., vaccines, solutions, formulations or pharmaceutical compositions) of the invention can comprise a solution of compositions (which include GAS, GGS or GCS carbohydrates or glycopeptides of the invention) disposed in or dissolved in a pharmaceutically acceptable carrier, e.g., acceptable vehicles and solvents that can be employed include water and Ringer's solution, an isotonic sodium chloride. In addition, sterile fixed oils can be employed as a solvent or suspending medium. For this purpose any fixed oil can be employed including synthetic mono- or diglycerides, or fatty acids such as oleic acid. In one embodiment, solutions and formulations used to practice the invention are sterile and can be manufactured to be generally free of undesirable matter. In one embodiment, these solutions and formulations are sterilized by conventional, well-known sterilization techniques.

The vaccines, solutions, formulations or pharmaceutical compositions used to practice the invention can comprise auxiliary substances as required to approximate physiological conditions such as pH adjusting and buffering agents, toxicity adjusting agents, e.g., sodium acetate, sodium chloride, potassium chloride, calcium chloride, sodium lactate and the like. The concentration of active agent in these formulations can vary widely, and can be selected primarily based on fluid volumes, viscosities and the like, in accordance with the particular mode of in vivo, in vitro or ex vivo administration selected and the desired results.

The vaccines, solutions, formulations or pharmaceutical compositions of the invention can be delivered by the use of liposomes. By using liposomes, particularly where the liposome surface carries ligands specific for target cells (e.g., immune cells for stimulating a humoral response), or are otherwise preferentially directed to a specific tissue or organ type, one can focus the delivery of the active agent into a target cells in an in vivo, in vitro or ex vivo application.

In alternative aspects, a vaccine of the invention can be administered with an adjuvant, e.g., the adjuvant can comprise or consist of incomplete Freund's adjuvant (IFA) or MONTANIDE ISA 51e; alum; aluminum phosphate; aluminum hydroxide; squalene; complete Freund's adjuvant (CFA), or levamisole; QS-21™, or STIMULON® (Antigenics, Lexington, Mass.); or muramyl dipeptide (MDP) or derivatives thereof; monophosphoryl lipid (MPL) or derivatives thereof; or monophosphoryl lipid A (MPLA) or derivatives thereof; or MF59™ or FLUAD® (Novartis, Basel, Switzerland); or as described in U.S. Pat. No. 7,182,962; or a glycosylceramide as described e.g. in U.S. Pat. No. 7,488,491; triacyl lipid A or derivatives thereof or OM-174™ (OM Pharma, Geneva, Switzerland); or SB-AS2™, or an oil in water emulsion comprising monophosphoryl lipid A (MPLA) and QS-21™; or SYNTEX™ adjuvant formulation (SAF) (Laboratorios Syntex SA, Mexico City Mexico), or an adjuvant comprising a muramyl dipeptide derivative (threonyl-MDP) in an oil-in-water (o/w) emulsion vehicle; or pluronic L121 or poloxamer 401; or a mucosal adjuvant comprising a detoxified mutant A subunit of a cholera toxin (CT) or an E. coli heat labile toxin (LT1 or LT2) as described in U.S. Pat. No. 7,485,304 (Novartis Vaccines and Diagnostics SRL); or an adjuvant as described in U.S. Pat. No. 7,357,936 (SmithKline Beecham Biologicals, SA); or any combination thereof.

In alternative aspects, a vaccine of the invention is administered with a non-specific immuno-stimulator, e.g., the non-specific immuno-stimulator can comprise or consist of a granulocyte-macrophage colony-stimulating factor polypeptide; or sargramostim, or LEUKINE™ (Bayer, Leverkusen, Germany).

Methods of delivering the vaccine are also well known in the art. For example, in alternative embodiments vaccines of the invention are formulated and delivered via a parenteral route comprising or consisting of a subcutaneous, an intravenous (IV), an intradermal, an intramuscular, an intraperitoneal, an intranasal, a transdermal or a buccal route.

In alternative embodiments vaccines of the invention are delivered intradermally or intra-epidermally using any needle-like structures or device, e.g., as described in U.S. Patent App. Pub. No. 20090012494, describing use of microneedle devices, e.g., with rows of hollow microneedles. In alternative embodiments vaccines of the invention are delivered using micro-cannula, e.g., as described in U.S. Pat. No. 7,473,247. When using this or another device or needle to practice this invention, vaccine formulations can be directly targeted into an intradermal space; or can be delivered into an intradermal space as a bolus or by infusion. In alternative embodiments, "intradermal" is administration of a vaccine formulation of this invention into the dermis in such a manner that the glycopeptide of the invention therein readily reaches the richly vascularized papillary dermis where it can be rapidly systemically absorbed, or the vaccine can be taken up directly by cells (e.g., dendritic cells) in the skin. In alternative embodiments, "intradermal" includes every layer of the skin, including stratum corneum, epidermis and dermis.

In one embodiment, a drug-delivery patch is used to deliver a vaccine formulation of this invention, e.g., as described in U.S. Patent App. Pub. No. 20090010998. In one embodiment, the invention provides a drug-delivery patch having at least one dissolvable layer comprising a carbohydrate or protein-conjugated carbohydrate of the invention and an adhesive backing or cover. In one embodiment, an individual is transdermally vaccinated by ablating an area of the stratum corneum of the individual and applying the patch to that area.

In one embodiment, a carbohydrate or protein-conjugated carbohydrate of the invention is delivered via dendritic cell administration, e.g., as described in U.S. Patent App. Pub. No. 20090010948. In one embodiment, a carbohydrate or protein-conjugated carbohydrate of the invention is formulated as a dendritic cell (DC)-based tumor vaccine; this modality is a well-known therapeutic approach for generating immune responses and for cancer treatment; see e.g., Schuler (2003) Curr. Opin. Immunol. 15(2):138-47; Dallal (2000) Curr. Opin. Immunol. 12(5):583-8; Steinman (2001) Int J. Cancer. 94(4):459-73. In practicing this embodiment, DCs can deliver not only the tumor antigen contained within a carbohydrate or protein-conjugated carbohydrate of this invention, but the DC also can be a natural adjuvant to boost the vaccine's efficiency. DCs also can provide critical molecules, cytokines or co-stimulatory signals to the T cells they interact with during activation.

Methods for determining the efficacy of a vaccine formulation of this invention, or a particular administration of a vaccine formulation of this invention, are well known in the art. For example, cell-based or humoral responses can be assessed (measured) using in vitro based assays and/or in vivo based assays, including animal based assays. Assays for measuring cell-based or humoral immune response are well known in the art, e.g., see, Coligan et al., (eds.), 1997, Current Protocols in Immunology, John Wiley and Sons, Inc. Cell-based or humoral immune responses may be detected and/or quantitated using standard methods known in the art including, e.g., an ELISA assay, chromium release assays and the like. The humoral immune response may be measured by detecting and/or quantitating the relative amount of an antibody which specifically recognizes an antigenic or immunogenic agent in the sera of a subject who has been treated with a vaccine formulation of this invention relative to the amount of the antibody in an untreated subject. ELISA assays can be used to determine total antibody titers in a sample obtained from a subject treated with an agent of the invention.

Whole Cell Attenuated Vaccines

In alternative embodiments, the invention provides whole cell or live attenuated vaccines comprising a bacterial cell of the invention, e.g., an isolated, modified or recombinant Group A Streptococcus (GAS), Group C Streptococcus (GCS) or Group G Streptococcus (GGS), e.g., a bacterial cell expressing a modified GAC, GCC and or GGC carbohydrate of the invention.

In one aspect, the invention provides immunogenic preparations comprising cells with reduced infectivity, e.g., as prepared as described in U.S. Pat. Nos. 7,560,113; 7,919, 096, for example, by contacting whole microorganisms with a fluid comprising carbon dioxide at or near its supercritical pressure and temperature conditions such that the infectivity and/or pathogenicity of the whole microorganisms are reduced. Chemical additives can also be used, e.g., adding hydrogen peroxide, acetic acid, peracetic acid, trifluoroacetic acid or mixtures thereof.

Polypeptides and Glycopeptides

In alternative embodiments, the invention provides carbohydrate or protein-conjugated carbohydrate (glycoconjugates), e.g., formulated as vaccines, for generating an immune response, e.g., a humoral immune response, in a mammal to a Group A Streptococcus (GAS), a Group C Streptococcus (GCS), or a Group G Streptococcus (GGS). In alternative embodiments, a vaccine, formulation, composition or pharmaceutical composition of the invention, comprises: a glycoconjugate comprising a polyrhamnose backbone, or a plurality of glycoconjugates comprising polyrhamnose backbones derived from a GAS; GCS; a GBS; a GGS; a GAS and a GCS; a GAS and a GBS; a GAS and a GGS; a GCS and a GBS; a GCS and a GGS; a GBS and a GGS; or a GAS, a GCS, a GBS and a GGS. In one embodiment, the protein component of the glycoconjugate is endogenous (e.g., a GAS polyrhamnose backbone attached or conjugated to a GAS peptide or protein component), or in alternative embodiment the protein component of the glycoconjugate is exogenous (the origin of the carbohydrate and the protein component do not match). In one embodiment, the protein component of the glycoconjugate is entirely synthetic or has no sequence similarity to a peptide from the same organism as the carbohydrate.

In alternative embodiments, molecules used to practice the invention (e.g., a carbohydrate or protein-conjugated carbohydrate of the invention) comprise a recombinant protein, a synthetic protein, a peptidomimetic, a non-natural peptide, or a combination thereof. Peptides and proteins used to practice the invention can be recombinantly expressed in vitro or in vivo. The peptides and polypeptides of the invention can be made and isolated using any method known in the art as well as using the methods described herein. Polypeptide and peptides used to practice the invention can also be synthesized, whole or in part, using chemical methods well known in the art. See e.g., Caruthers (1980) Nucleic Acids Res. Symp. Ser. 215-223; Horn (1980) Nucleic Acids Res. Symp. Ser. 225-232; Banga, A. K., Therapeutic Peptides and Proteins, Formulation, Processing and Delivery Systems (1995) Technomic Publishing Co., Lancaster, Pa. For example, peptide synthesis can be performed using various solid-phase techniques (see e.g., Roberge (1995) Science 269:202; Merrifield (1997) Methods Enzymol. 289:3-13) including any automated polypeptide synthesis process known in the art.

In alternative embodiments, carbohydrate or protein-conjugated carbohydrate of the invention can comprise any "mimetic" and/or "peptidomimetic" form. In alternative embodiments, glycopeptides and glyco-polypeptides of the invention comprise synthetic chemical compounds that have substantially the same structural and/or functional characteristics of a natural polypeptide. A mimetic used to practice the invention can be either entirely composed of synthetic, non-natural analogues of amino acids, or, is a chimeric molecule of partly natural peptide amino acids and partly non-natural analogs of amino acids. A mimetic used to practice the invention can also incorporate any amount of natural or non-natural amino acid conservative substitutions as long as such substitutions also do not substantially alter the mimetic's structure and/or activity.

Nanoparticles, Nanolipoparticles and Liposomes

The invention also provides nanoparticles, nanolipoparticles, vesicles and liposomal membranes comprising compounds used to practice the compositions and methods of this invention, e.g., use of vaccines, pharmaceutical formulations and compositions to treat, prevent or ameliorate Group A Streptococcus (GAS), Group C Streptococcus (GCS) and/or Group G Streptococcus (GGS) infections. In alternative embodiments, these compositions are designed to target specific molecules, including biologic molecules, such as polypeptides, including cell surface polypeptides, e.g., for targeting a desired cell type, e.g., a dendritic cell and the like for stimulating an immune response.

The invention provides multilayered liposomes comprising compounds used to practice this invention, e.g., as described in Park, et al., U.S. Pat. Pub. No. 20070082042. The multilayered liposomes can be prepared using a mixture of oil-phase components comprising squalane, sterols, ceramides, neutral lipids or oils, fatty acids and lecithins, to about 200 to 5000 nm in particle size, to entrap a composition used to practice this invention.

Liposomes can be made using any method, e.g., as described in Park, et al., U.S. Pat. Pub. No. 20070042031, including method of producing a liposome by encapsulating an active agent, the method comprising providing an aqueous solution in a first reservoir; providing an organic lipid solution in a second reservoir, and then mixing the aqueous solution with the organic lipid solution in a first mixing region to produce a liposome solution, where the organic lipid solution mixes with the aqueous solution to substantially instantaneously produce a liposome encapsulating the active agent; and immediately then mixing the liposome solution with a buffer solution to produce a diluted liposome solution.

In one embodiment, liposome compositions used to practice this invention comprise a substituted ammonium and/or polyanions, e.g., for targeted delivery of a compound of the invention, as described e.g., in U.S. Pat. Pub. No. 20070110798.

The invention also provides nanoparticles comprising compounds used to practice this invention in the form of active agent-containing nanoparticles (e.g., a secondary nanoparticle), as described, e.g., in U.S. Pat. Pub. No. 20070077286. In one embodiment, the invention provides nanoparticles comprising a fat-soluble active agent of this invention or a fat-solubilized water-soluble active agent to act with a bivalent or trivalent metal salt.

In one embodiment, solid lipid suspensions can be used to formulate and to deliver compositions used to practice this invention to mammalian cells in vivo, in vitro or ex vivo, as described, e.g., in U.S. Pat. Pub. No. 20050136121.

Delivery Vehicles

In alternative embodiments, any delivery vehicle can be used to practice the methods or used to practice this invention, e.g., to deliver compositions of the invention (which include GAS, GGS or GCS carbohydrate or protein-conjugated carbohydrate of the invention) to mammalian cells in vivo, in vitro or ex vivo. For example, delivery vehicles comprising polycations, cationic polymers and/or cationic peptides, such as polyethyleneimine derivatives, can be used e.g. as described, e.g., in U.S. Pat. Pub. No. 20060083737.

In one embodiment, a dried polypeptide-surfactant complex is used to formulate a composition used to practice this invention, e.g. as described, e.g., in U.S. Pat. Pub. No. 20040151766.

In one embodiment, a composition used to practice this invention can be applied to cells using vehicles with cell membrane-permeant peptide conjugates, e.g., as described in U.S. Pat. Nos. 7,306,783; 6,589,503. In one aspect, the composition to be delivered is conjugated to a cell membrane-permeant peptide. In one embodiment, the composition to be delivered and/or the delivery vehicle are conjugated to a transport-mediating peptide, e.g., as described in U.S. Pat. No. 5,846,743, describing transport-mediating peptides that are highly basic and bind to poly-phosphoinositides.

In one embodiment, electro-permeabilization is used as a primary or adjunctive means to deliver the composition to a cell, e.g., using any electroporation system as described e.g. in U.S. Pat. Nos. 7,109,034; 6,261,815; 5,874,268.

Dosaging

The vaccines, formulations, pharmaceutical compositions and formulations of the invention can be administered for prophylactic and/or therapeutic treatments. In therapeutic applications, compositions are administered to a subject already suffering from a disease, condition, infection or defect in an amount sufficient to cure, alleviate or partially arrest the clinical manifestations of the disease, condition, infection or disease and its complications (a "therapeutically effective amount"). For example, in alternative embodiments, pharmaceutical compositions and formulations of the invention are administered to an individual in need thereof in an amount sufficient to treat, prevent, reverse and/or ameliorate an infection, e.g., a GAS, GGS or GCS infection.

The amount of pharmaceutical composition adequate to accomplish this is defined as a "therapeutically effective dose." The dosage schedule and amounts effective for this use, i.e., the "dosing regimen," will depend upon a variety of factors, including the stage of the disease or condition, the severity of the disease or condition, the general state of the patient's health, the patient's physical status, age and the like. In calculating the dosage regimen for a patient, the mode of administration also is taken into consideration.

In alternative embodiments of the methods, a vaccine of the invention is administered parentally or orally, or systemically or topically. The vaccine can be administered via a parenteral route or via a route comprising or consisting of a subcutaneous, an intramuscular, an intravenous (IV), an intradermal, an intramuscular, an intraperitoneal, an intranasal, an intradermal, a transdermal or a buccal route. The vaccine can be administered parenterally by bolus injection or by gradual perfusion over time, or the vaccine can be administered by an oral or a topical route.

In alternative embodiments, a vaccine of the invention is administered using a vaccination regime comprising at least one second (booster) administration, or the vaccine is administered at intervals of 1 week, 2 weeks, 4 weeks (or one month), 6 weeks, 8 weeks (or two months) or one year.

In alternative embodiments, a vaccine of the invention is administered at a daily dose of carbohydrate or protein-conjugated carbohydrate in a range of about 10 nanograms to 10 milligrams, or about 1 microgram to 10 milligrams.

In alternative embodiments, the invention provides methods for generating a carbohydrate antigen-specific cytotoxic lymphocyte (CTL) response, and/or a CD8+ T cell response, comprising contacting naïve CTL cells or CD8+ T cells with an effective amount of one or more (at least one) carbohydrate or protein-conjugated carbohydrate of the invention; the pharmaceutical or formulation of the invention; the liposome of the invention; or the nanoparticle of the invention. In alternative embodiments, the invention provides methods for generating an antigen-specific helper T cell response, and/or a CD4+ T cell response, comprising contacting naïve helper T cells or CD4+ T cells with an effective amount of one or more (at least one) glycopeptides (glycoconjugates) of the invention; the pharmaceutical or formulation of the invention; the liposome of the invention; or the nanoparticle of the invention. In alternative embodiments, the contacting is in vitro or in vivo. In alternative embodiments, the contacting is in vivo to (in) a mammal or a human.

The dosage regimen also takes into consideration pharmacokinetics parameters well known in the art, i.e., the active agents' rate of absorption, bioavailability, metabolism, clearance, and the like (see, e.g., Hidalgo-Aragones (1996) J. Steroid Biochem. Mol. Biol. 58:611-617; Groning (1996) Pharmazie 51:337-341; Fotherby (1996) Contraception 54:59-69; Johnson (1995) J. Pharm. Sci. 84:1144-1146; Rohatagi (1995) Pharmazie 50:610-613; Brophy (1983) Eur. J. Clin. Pharmacol. 24:103-108; the latest Remington's, supra). The state of the art allows the clinician to determine the dosage regimen for each individual patient, active agent and disease or condition treated. Guidelines provided for similar compositions used as pharmaceuticals can be used as guidance to determine the dosage regiment, i.e., dose schedule and dosage levels, administered practicing the methods of the invention are correct and appropriate.

Single or multiple administrations of formulations can be given depending on the dosage and frequency as required and tolerated by the patient. The formulations should provide a sufficient quantity of active agent to effectively treat, prevent or ameliorate a conditions, diseases or symptoms as described herein. Dosages can be used in topical or oral administration or administering by powders, spray or inhalation. Actual methods for preparing parenterally or non-parenterally administrable formulations will be known or apparent to those skilled in the art and are described in more detail in such publications as Remington's, supra.

The methods of the invention can further comprise co-administration with other drugs or pharmaceuticals, e.g., compositions for treating any infection, including a GAS, GGS or GCS infection, and the like. For example, the methods and/or compositions and formulations of the invention can be co-formulated with and/or co-administered with, fluids, antibiotics, cytokines, immunoregulatory agents, anti-inflammatory agents, pain alleviating compounds, complement activating agents, such as peptides or proteins comprising collagen-like domains or fibrinogen-like domains (e.g., a ficolin), carbohydrate-binding domains, and the like and combinations thereof.

Diagnostic Compositions and Methods

The invention provides compositions and methods for diagnosing a Streptococcal infection, or a streptococcal pharyngitis ("strep throat") in a mammal. In alternative embodiments, the invention provides diagnostic tests, assays or test strips, and the like (e.g., latex agglutination assays, enzyme immunoassays, enzyme-linked immunosorbent assays (ELISAs), optical, liquid or solid phase immunoassays and the like) for detecting the presence of or diagnosing a Streptococcal infection, or a streptococcal pharyngitis ("strep throat") in a mammal, e.g., a human. In alternative embodiments, the diagnostic tests, assays, test strips and the like of the invention can be rapid and/or have improved sensitivity and/or specificity to as compared to current technologies as they target a bacterial specific motif (polyrhamnose) rather than a common sugar motif (e.g., a GlcNac or a GlcNac) present on mammalian (e.g., human) cells and mucosal secretions. Since an identical polyrhamnose backbone is shared by GAS and GCS, in alternative embodiments these rapid diagnostic tests and assays have the advantage of identifying both species lacking in current rapid diagnostic methodologies.

In alternative embodiments, the diagnostic tests, assays, test strips and the like of the invention comprise use of one or more isolated or recombinant antibodies, polyclonal or monoclonal antibodies, or sera (e.g., hyperimmune sera) of the invention. In alternative embodiments, the antibodies or sera can specifically react against, or specifically bind to, or are specifically derived against one, two or all of: (a) a mutant GAS, GGS or GCS carbohydrate antigen, engineered to partially lack, substantially lack or completely lack an immuno-crossreactive carbohydrate side chain, (b) a mutant GAS carbohydrate antigen engineered to partially lack, substantially lack or completely lack an immuno-crossreactive GlcNac side chain; and/or (c) a mutant GCS carbohydrate antigen engineered to partially lack, substantially lack or completely lack an immunodominant GalNac-GalNac side chain.

Any form or variation of diagnostic tests, assays, immunoassays or test strips and the like utilizing antibodies (including antigen-binding antibody fragments) or sera can be used to practice this invention. For example, a composition or a method of the invention can comprise or comprise use of a sampling device and/or a test strip, or methods, as described in e.g.: U.S. Pat. No. 8,231,549, e.g., where an on-site analyzer such as an optical analyzer and/or an electrochemical analyzer can be mounted in the device for analyzing a body fluid. For example, a composition or a method of the invention can comprise or comprise use of an assay device or test strip or a method as described in e.g.: U.S. Pat. No. 8,206,661; or an assay device allowing for the testing for multiple analytes in a liquid sample, as described in U.S. Pat. No. 8,202,487; or an analyte monitor having a sensor, a sensor control unit, and a display unit as described in U.S. Pat. No. 8,177,716; or an electrochemical test strip as described in U.S. Pat. No. 8,172,995; or an evanescent light fluoroimmunoassay, or waveguide immunosensor, as described in U.S. Pat. No. 5,512,492; or a chromatographic specific binding assay strip device for e.g., immuno gold lateral flow assays as described in U.S. Pat. No. 8,153,444; or an immunological latex turbidimetry method as described in U.S. Pat. No. 7,759,074 or 7,560,238; or an assay device as described in U.S. Pat. App. No. 20120193228; or an analyte testing device having a casing and a test strip positioner as described in U.S. Pat. App. No. 20120183442; or, a system as described in U.S. Pat. App. No. 20120181190, for correcting the measurement of an analyte in a sample, the system comprising a test strip and a meter programed to calculate and obtain a corrected analyte concentration; or a lateral flow assay test strip as described in U.S. Pat. App. No. 20120164028; or an immunochromatographic assay as described in U.S. Pat. App. No. 20120135420; or an electronic diagnostic device for detecting the presence of an analyte in a fluid sample assay as described in U.S. Pat. App. No. 20120083044; or a magnetic immunochromatographic test strip as described in U.S. Pat. App. No. 20110117672; or an apparatus for the rapid determination of analyte in a liquid sample using immunoassays incorporating magnetic capture of beads as described in U.S. Pat. App. No. 20120034624 or 20120031773; or devices and methods for detecting analytes using chemiluminescent compounds as described in U.S. Pat. App. No. 20110318747; or apparatus and methods for assaying analytes using photoelectrochemical molecules as labels as described in U.S. Pat. App. No. 20060148102. In alternative embodiments, a variation of the Becton-Dickinson LINK 2 STREP A RAPID TEST™, a rapid antigen detection test (RADT) for diagnosing streptococcal pharyngitis, using compositions and methods of the invention can be used.

Compositions of the invention, e.g., carbohydrate antigens, glycoconjugates, antibodies and the like, and antibody-antibody binding detection for the diagnostic methods of the invention, can be detected and/or quantified by any method known in the art, including, e.g., nuclear magnetic resonance (NMR), spectrophotometry, radiography (protein radiolabeling), electrophoresis, capillary electrophoresis, high performance liquid chromatography (HPLC), thin layer chromatography (TLC), hyperdiffusion chromatography, various immunological methods, e.g. immunoprecipitation, immunodiffusion, immuno-electrophoresis, radioimmunoassays (RIAs), enzyme-linked immunosorbent assays (ELISAs), immuno-fluorescent assays, gel electrophoresis (e.g., SDS-PAGE), staining with antibodies, fluorescent activated cell sorter (FACS), pyrolysis mass spectrometry, Fourier-Transform Infrared Spectrometry, Raman spectrometry, GC-MS, and LC-Electrospray and cap-LC-tandem-electrospray mass spectrometries, and the like.

Magnetic Molecules or Particles

The invention provides magnetic molecules or particles for diagnosing a Streptococcal infection, or a streptococcal pharyngitis ("strep throat") in a mammal. In alternative embodiments, the invention provides diagnostic tests using magnetic molecules or particles for detecting the presence of or diagnosing a Streptococcal infection, or a streptococcal pharyngitis ("strep throat") in a mammal, e.g., a human.

In alternative embodiments, compositions of the invention (including vaccines and antibodies of the invention) comprise a plurality of magnetic molecules or particles. Any magnetic molecule or particle can be used. For example, in alternative embodiments, magnetic molecules or particles used to practice the invention comprise: dextran iron oxide nanoparticles; magnetically-responsive microparticles or nanoparticles as described, e.g., in U.S. Pat. No. 7,989,065, or magnetic microspheres, nanospheres, microbeads or nanobeads, as described, e.g., in U.S. Pat. No. 7,994,592; a superparamagnetic bead or polystyrene beads, as described, e.g., in U.S. Pat. No. 7,989,614, e.g., DYNABEADS™

Dynal AS (Oslo, Norway); or, superparamagnetic fine particles, as described, e.g., in U.S. Pat. Nos. 7,981,512; 7,713,627, or 7,399,523, describing spinel ferrimagnetic particles. In one embodiment, superparamagnetic particles comprising iron oxide having e.g., between about 0.1 to 10% by weight iron oxide based on the weight of the magnetic particles are used, e.g., as described in U.S. Pat. No. 5,368,933. Any device that can separate a magnetic particle or molecule from a sample can be used, e.g., as a magnetic separator as described in U.S. Pat. Nos. 7,985,340; 6,143,577; or 5,770,461.

Hydrogels or Gels

The invention provides gels or hydrogels for diagnosing a Streptococcal infection, or a streptococcal pharyngitis ("strep throat") in a mammal. In alternative embodiments, the invention provides diagnostic tests using gels or hydrogels for detecting the presence of or diagnosing a Streptococcal infection, or a streptococcal pharyngitis ("strep throat") in a mammal, e.g., a human.

Any gel or hydrogel can be used; for example, in alternative embodiments, compositions of the invention comprise a hydrogel, which can be any macromolecular networks that contains a large fraction of solvent within their structure and do not dissolve, or, a colloidal gel in which water is the dispersion medium of the colloid having a mixture with properties between those of a solution and fine suspension (a colloid gel is a colloid in a more solid form than a sol). In alternative embodiments, compositions of the invention comprise a "non-responsive" hydrogel, e.g., a simple polymeric network that dramatically swells upon exposure to water, and/or a "responsive" hydrogel, e.g., a gel having added functionality and display changes in solvation in response to certain stimuli such as temperature. Any non-toxic hydrogel can be used.

For example, in alternative embodiments, compositions of the invention comprise a hydrogel comprising: an acacia, alginic acid, sodium carboxymethylcellulose, microcrystalline cellulose, dextrin, ethylcellulose, gelatin, liquid glucose, polyvinyl pyrrolidone, carboxyvinyl polymer, methylcellulose, hydroxymethyl cellulose, low molecular weight polyethylene oxide polymers, hydroxyethyl cellulose, hydroxypropyl cellulose, hydroxypropyl methylcellulose (HPMC), gums, acrylate polymers, methacrylate polymers and/or maltodextrin and/or mixtures thereof.

Arrays, or "BioChips"

Polypeptides of the invention, including antibodies and serum, e.g., vaccine serum, and/or carbohydrates of the invention, can be immobilized to, affixed to, or applied to, an array, microarray, chip, diagnostic chip, biochip and the like to, e.g., identify the presence of, or to diagnose, a Streptococcal infection, e.g., Group A *Streptococcus* (GAS), Group C *Streptococcus* (GCS), or Group A *Streptococcus* (GGS), infections, or other pathogenic *Streptococcus* infections.

Any form or variation of a carbohydrate or a polypeptide array, microarray, chip, diagnostic chip, biochip and the like can be used to practice this invention, e.g., as described in U.S. Pat. Nos. 7,622,273; 7,303,924; 7,223,592; 6,506,558; and/or 6,919,211.

The invention will be further described with reference to the examples described herein; however, it is to be understood that the invention is not limited to such examples.

EXAMPLES

Example 1: Carbohydrate or Protein-Conjugated Carbohydrates of the Invention as Vaccines and Formulations This example describes exemplary methods for making and using compounds of the invention.

Figure 1B:
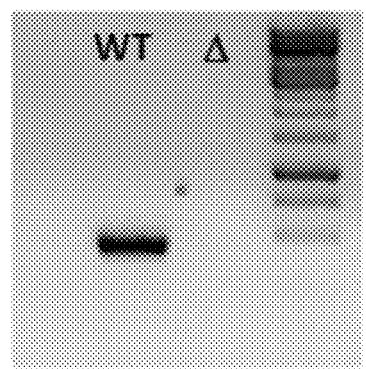
FIG. 1B illustrates a PCR analysis shows absence of the gacI gene (incorrectly labeled gacH) in the knockout mutant.
Figure 1C:
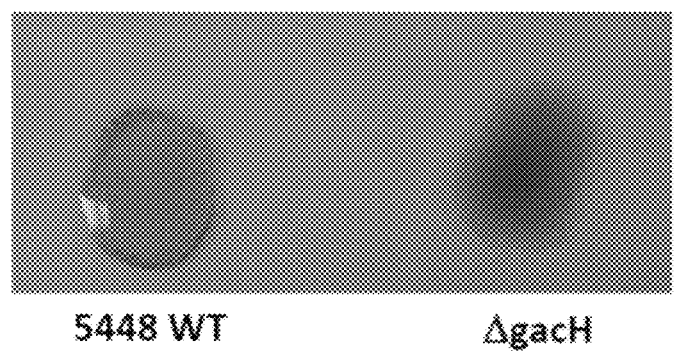
FIG. 1C illustrates a latex agglutination for group A carbohydrate (GlcNac side chain) is no longer reactive in the GAS ΔgacI (incorrectly labeled ΔgacI) mutant.
Figure 1D:
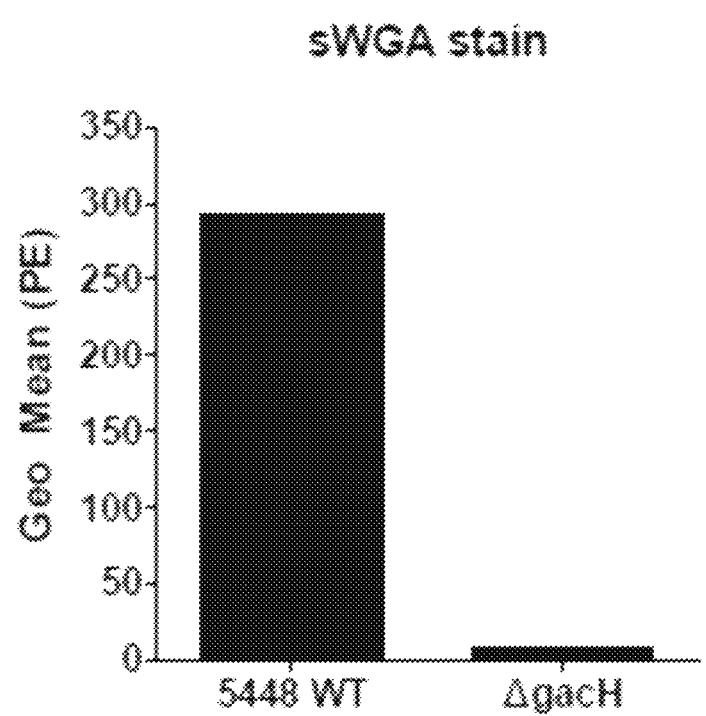
FIG. 1D graphically summarizes this data.

We have discovered the genetic operon for assembling the GAC in GAS through bioinformatics analysis, as schematically illustrated in FIG. 1A. We have generated a viable allelic exchange GAS mutant, called DgacH, which expresses a mutated GAC, as illustrated in FIGS. 1B, 1C and 1D.

FIG. 1A schematically illustrates the genetic operon for assembling the GAC in GAS through bioinformatics analysis, and shows the twelve-gene locus encoding the biosynthetic machinery for the group A streptococcal (GAS) cell wall carbohydrate antigen. Included are proposed gene designations based on homology, designation within the sequenced GAS M1 5005 genome sequence, and length of the gene. Ultimately, we have designated the genes within the locus as gacA-gacL. Highlighted is gene, then incorrectly called gacH (correctly designated gacI in upcoming figures) because of the role we demonstrate that it plays in adding the GlcNac side chain to the polyrhamnose backbone of the antigen. FIG. 1B illustrates a PCR analysis shows absence of the gacI gene (incorrectly labeled gacH) in the knockout mutant. FIG. 1C illustrates latex agglutination for group A carbohydrate (GlcNac side chain) is no longer reactive in the GAS ΔgacI (incorrectly labeled ΔgacI) mutant, and illustrates binding of the sWGA lectin probe, specific for terminal GlcNac sugars, to the bacterial surface. This binding is lost in the ΔgacI mutant (incorrectly labeled ΔgacH). The results confirm loss of the GlcNac side chain in the mutant. FIG. 1D graphically summarizes this data.

Purification of this mutant GAC carbohydrate has been performed and glycoanalysis has unambiguously demonstrates the absence of GlcNAc side chain, as graphically illustrated in FIG. 2. The invention provides carbohydrate or protein-conjugated carbohydrate of this purified mutant GAC as a vaccine against GAS, GCS, GBS and/or GGS, as well as for other pathogenic streptococci bearing a polyrhamnose motifs in their cell wall carbohydrate.

Figure 2A:
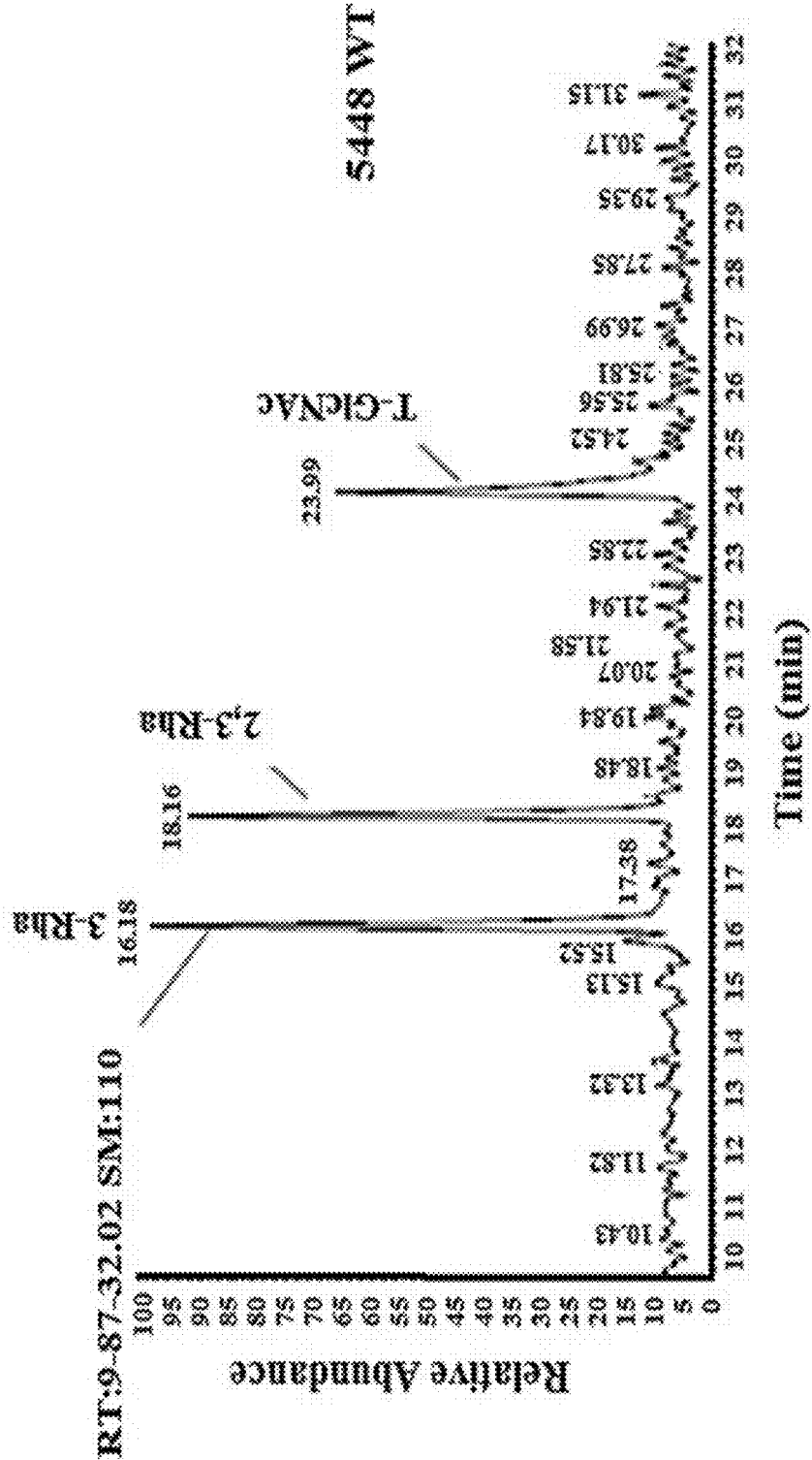
FIG. 2A-B graphically illustrates a glycoanalysis subsequent to purification of this mutant GAC carbohydrate, the data unambiguously demonstrating the absence of GlcNAc side chain.
Figure 2B:
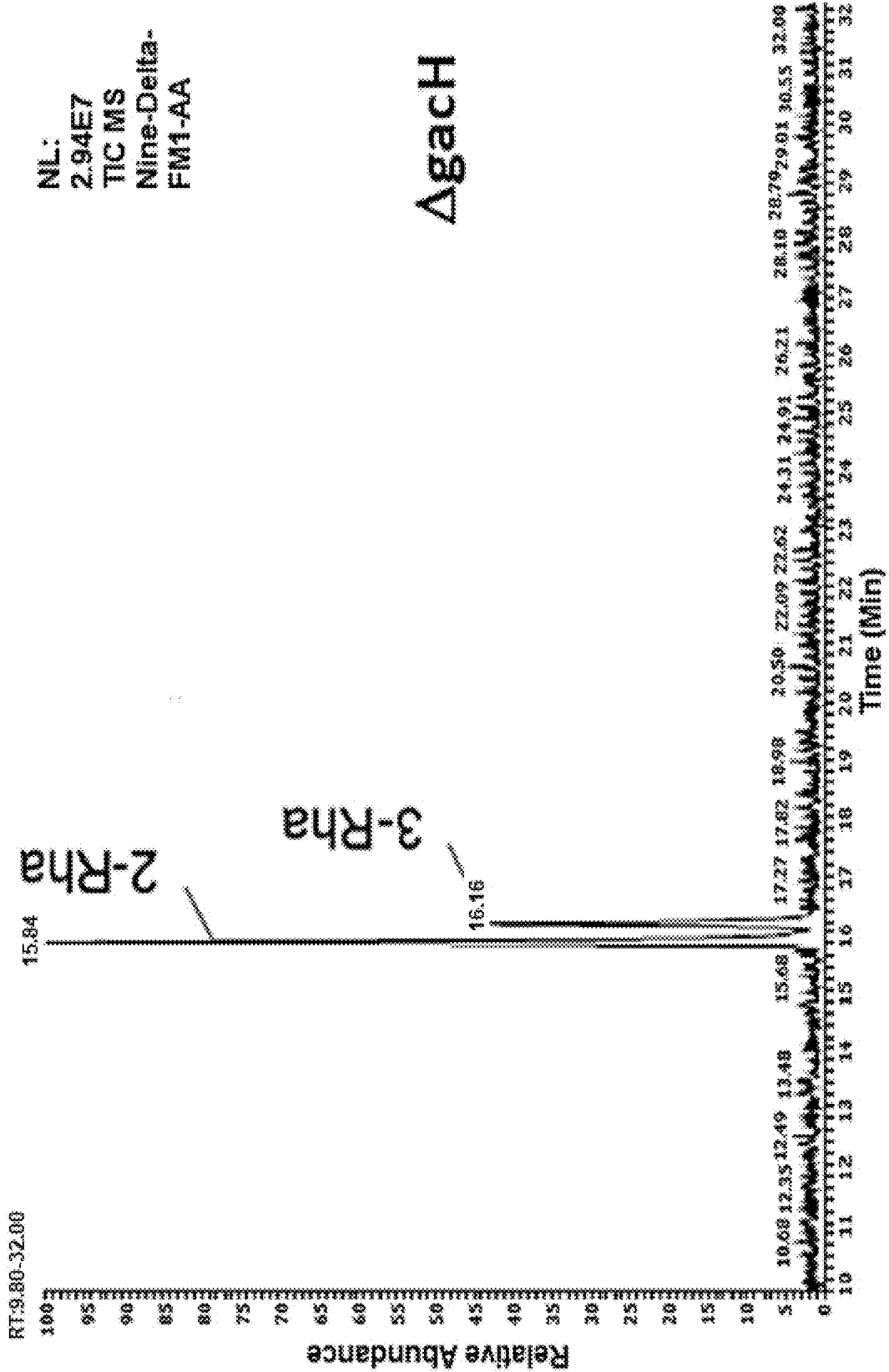
Figure 4:
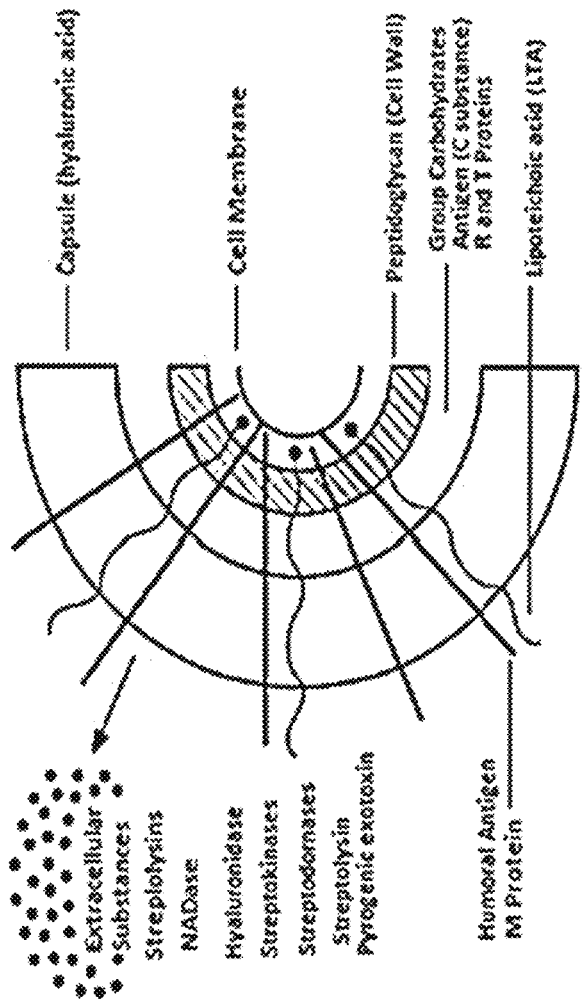
FIG. 4 schematically illustrates a representation of the cell wall and surface structures of the leading human pathogen: group A *Streptococcus*.
Figure 7:
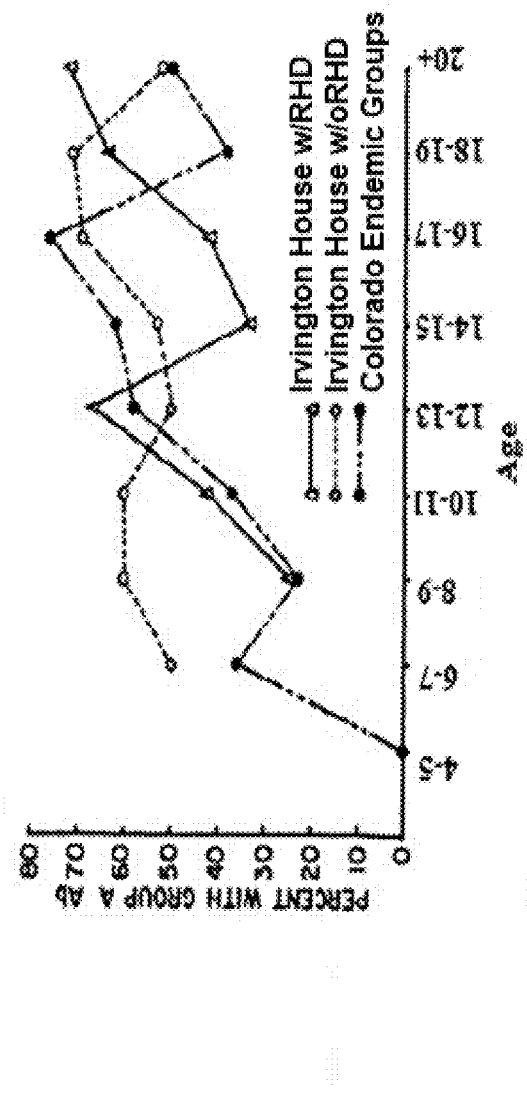

FIG. 2A illustrates a formal glycoanalysis of linkages in the WT M1 GAS carbohydrate shows rhamnose sugars and the β-1-3-linked GlcNac side chain; FIG. 2B illustrates a formal glycoanalysis of linkages in the M1 GAS ΔgacI mutant cell wall carbohydrate (incorrectly labeled ΔgacH) shows unambiguously the loss of the β-1-3-linked GlcNac side chain.

Figure 8:
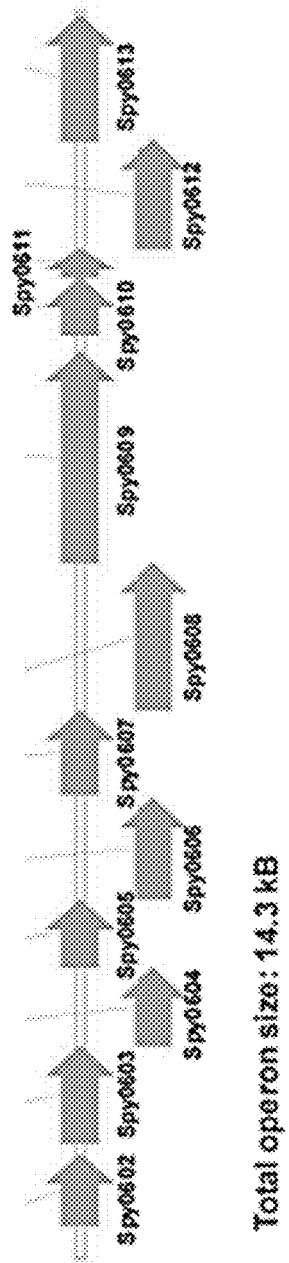
Figure 9A:
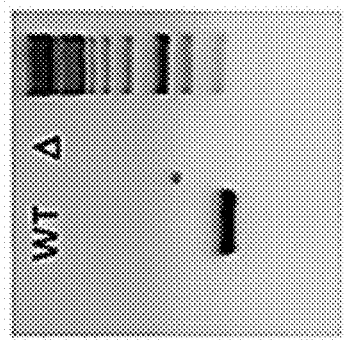
Figure 9B:
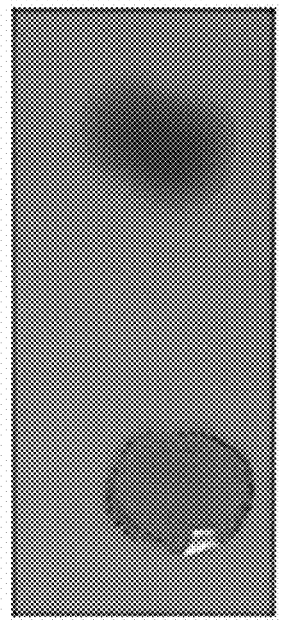
Figure 9C:
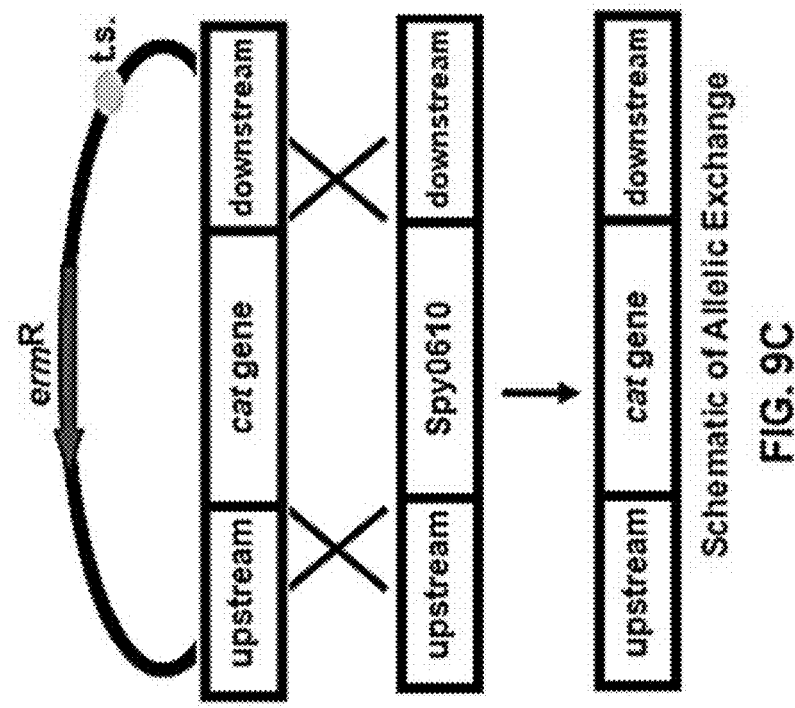
Figure 10A:
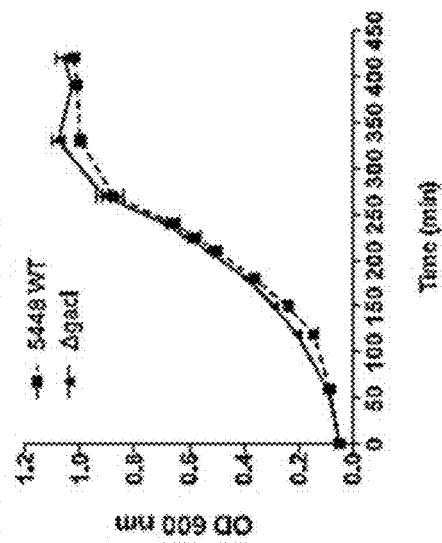
Figure 10B:
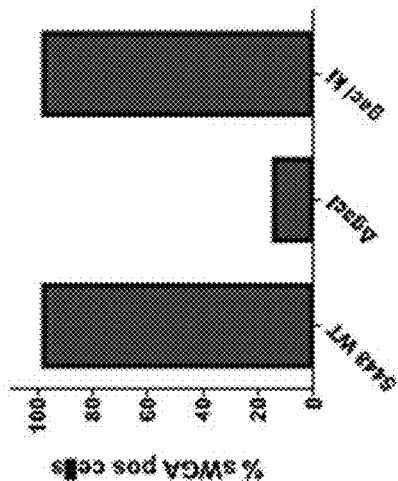
Figure 11A:
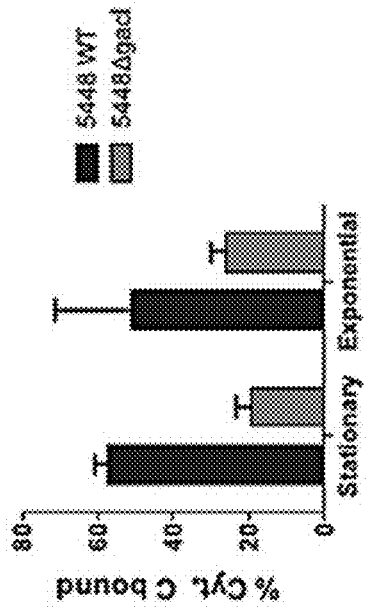
Figure 11B:
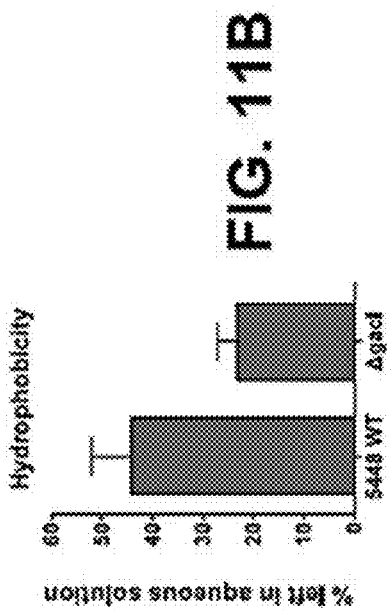
Figure 12:
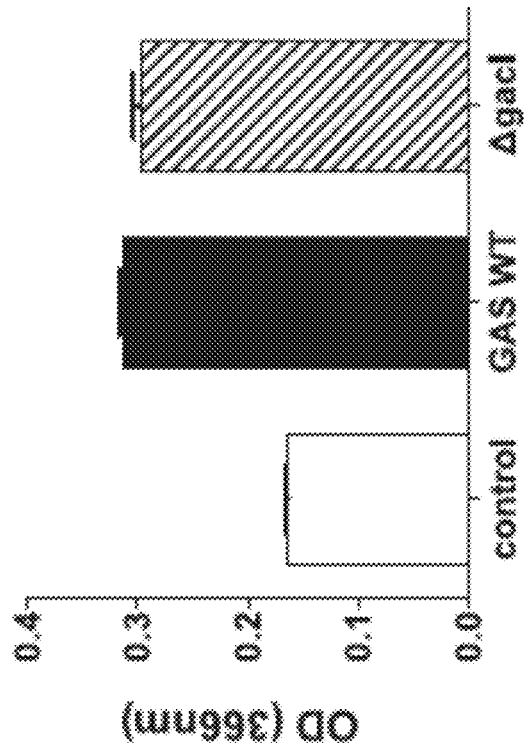
Figure 13:
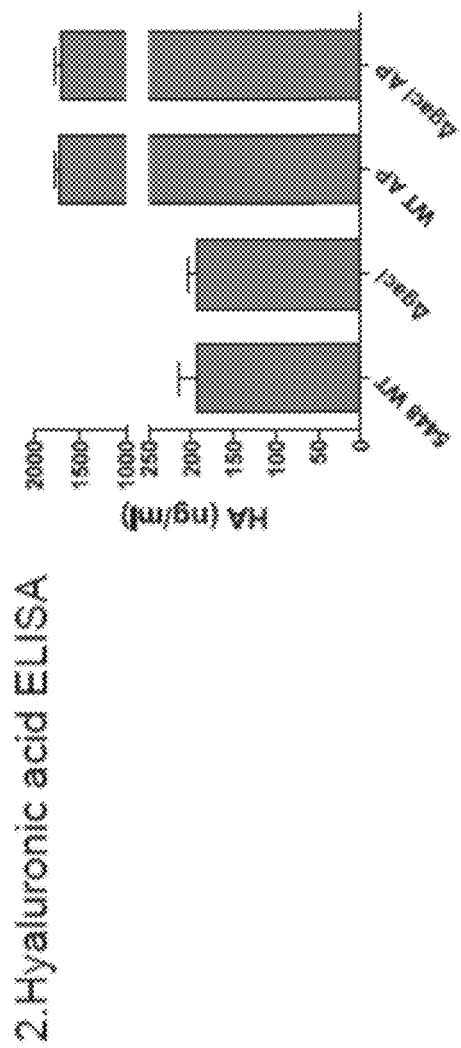
Figure 14:
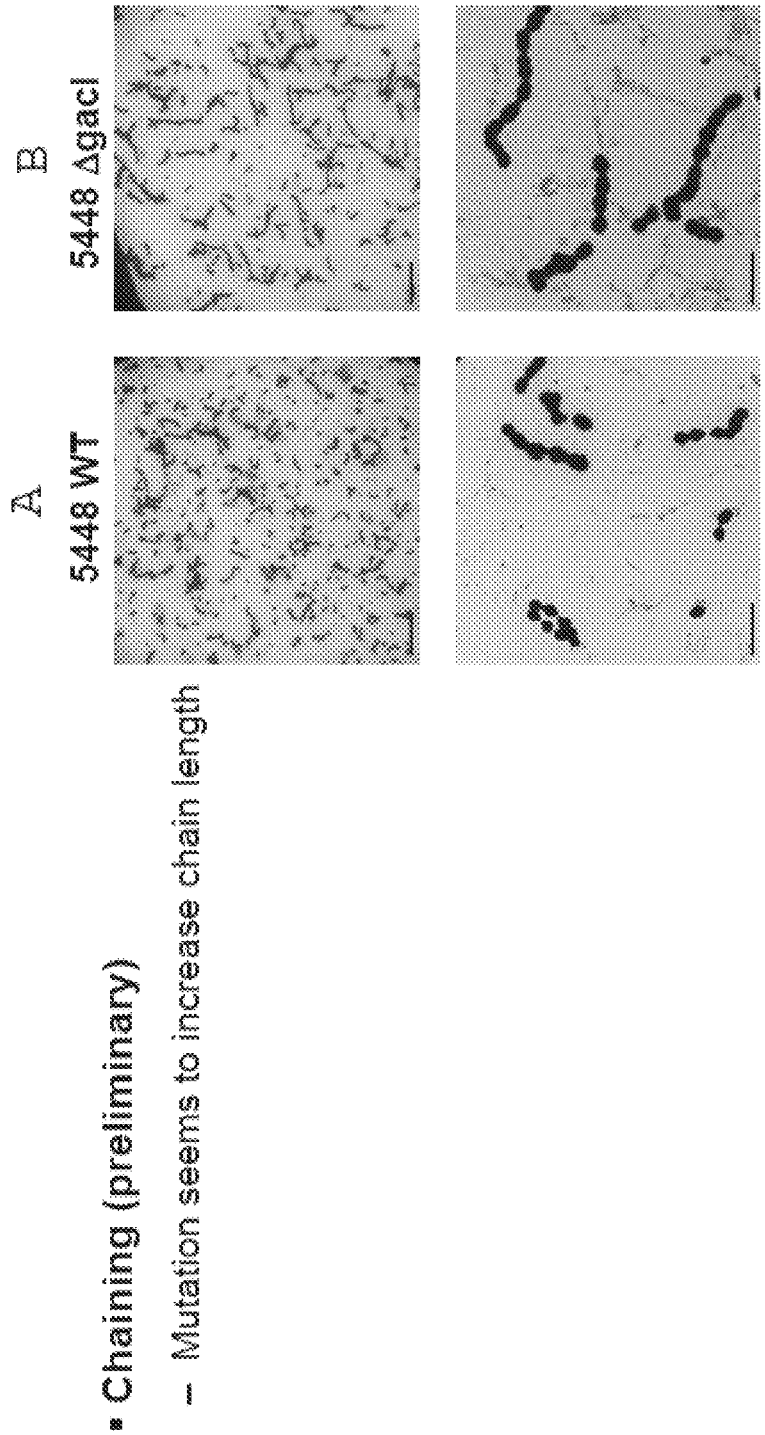
FIG. 14A-B illustrates a microscopic appearance comparing WT (FIG. 14A) and ΔgacI mutant (FIG. 14B) chain length, where the ΔgacI mutant (FIG. 14B) showing a gross morphology of cell walls is similar, but there is a tendency in the mutation to longer chain length, when compared to the WT parent GAS M1T1 strain (FIG. 14A).
Figure 15:
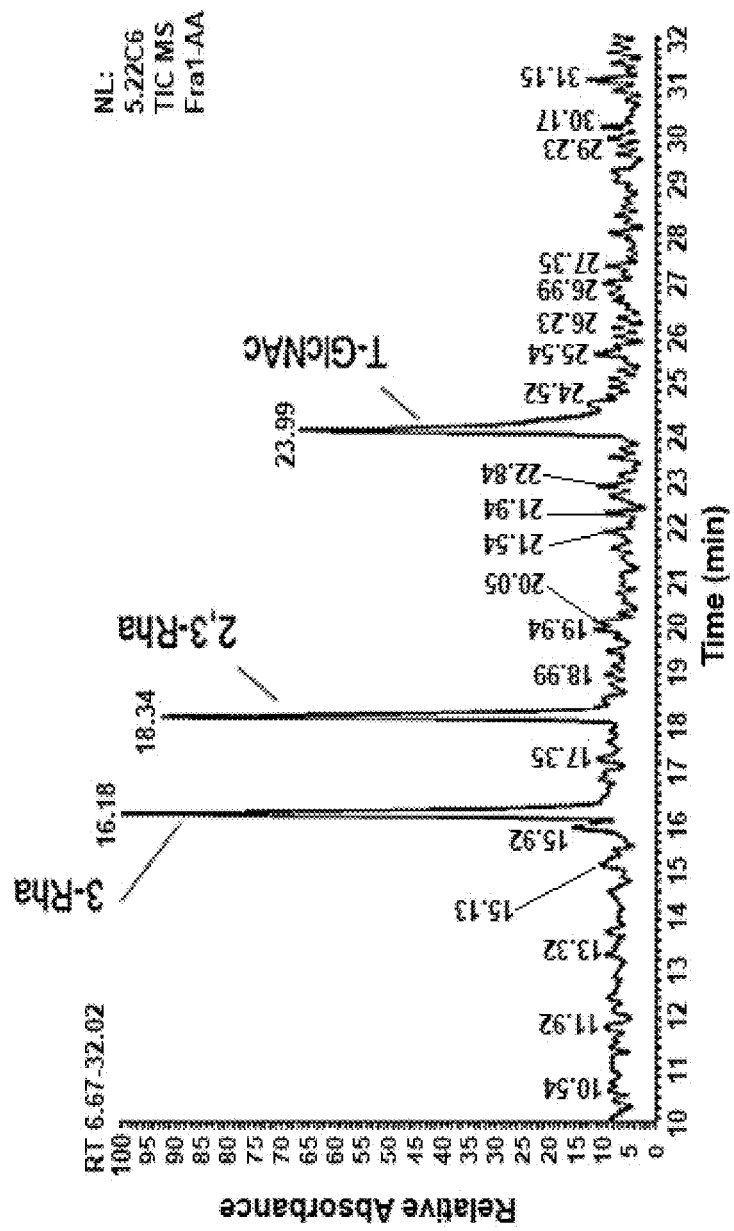
FIG. 15 illustrates a formal glycoanalysis of linkages in the WT M1 GAS carbohydrate showing rhamnose sugars and the β-1-3-linked GlcNac side chain.
Figure 16:
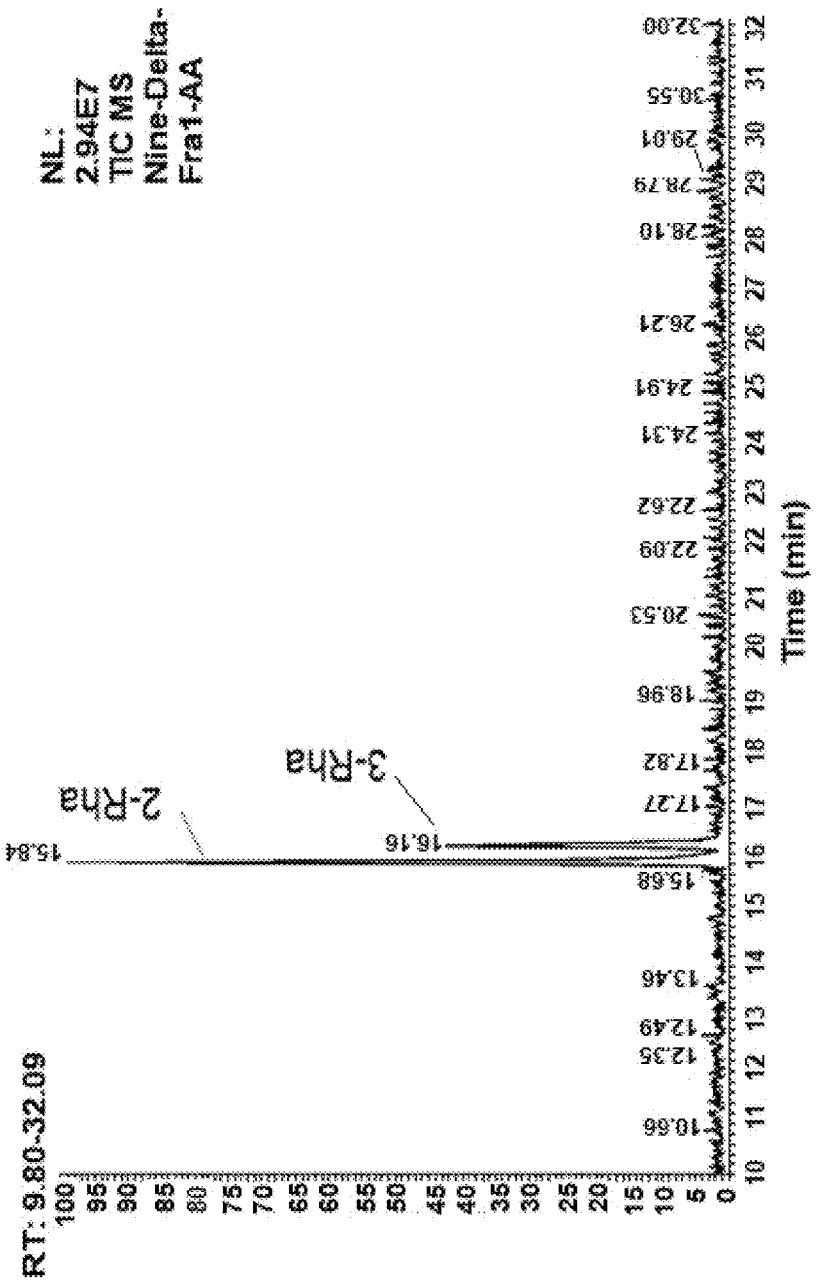
FIG. 16 illustrates a formal glycoanalysis of linkages in the M1 GAS ΔgacI mutant cell wall carbohydrate showing unambiguously the loss of the β-1-3-linked GlcNac side chain.
Figure 17:
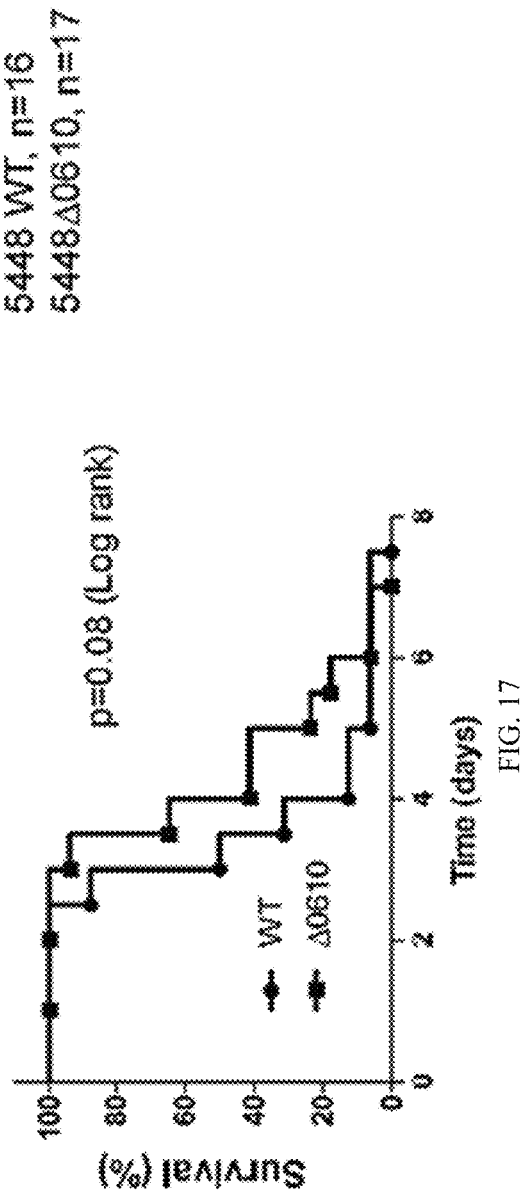
FIG. 17 graphically illustrates data from a mouse infection experiment (ΔgacI mutant compared to the WT parent) showing a trend towards attenuation of virulence of ΔgacI mutant compared to the WT parent strain in a mouse model of systemic infection.
Figures 18A, 18B:
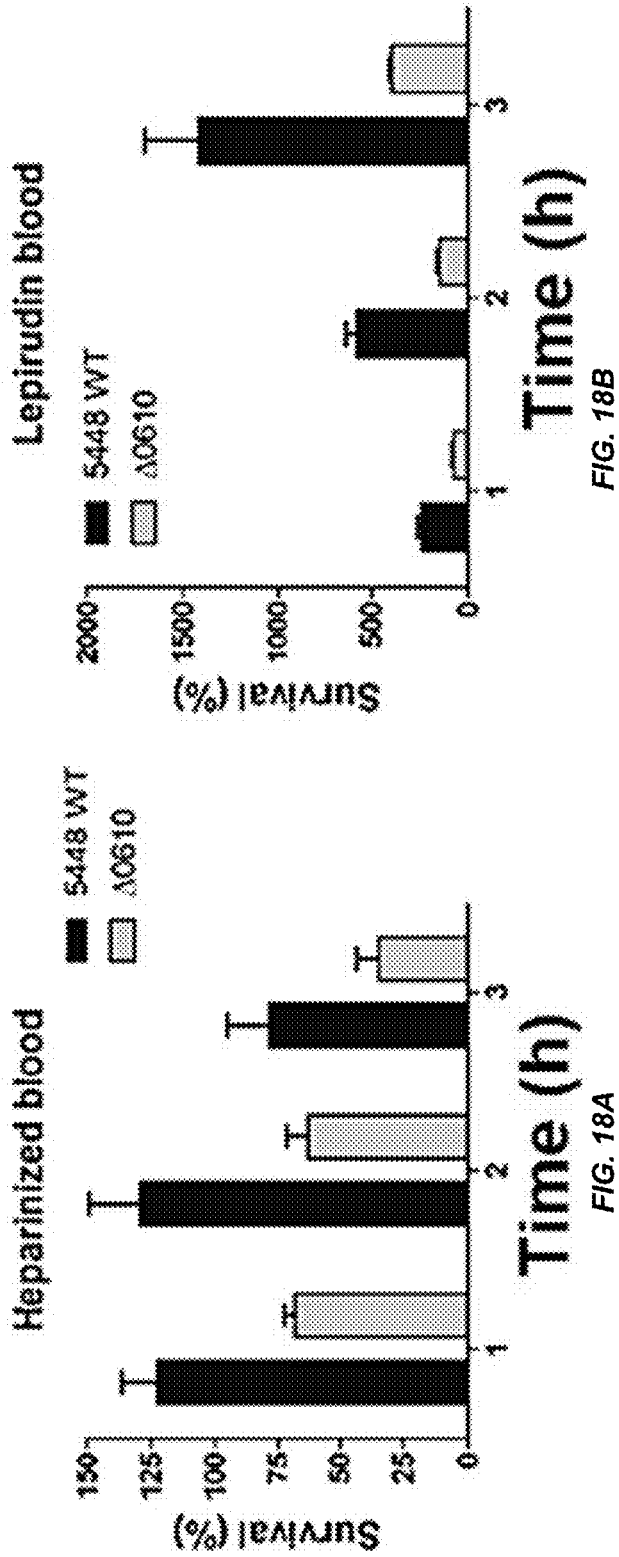
FIG. 18A-B graphically illustrates data from a whole blood survival test demonstrating that the ΔgacI mutant survives less well than the WT parent M1 GAS strain in freshly isolated human whole blood whether heparin (FIG. 18A) or lepirudin (FIG. 18B) is used for anticoagulation; the results indicate the GlcNAc side chain contributes to whole blood survival.
Figure 19:
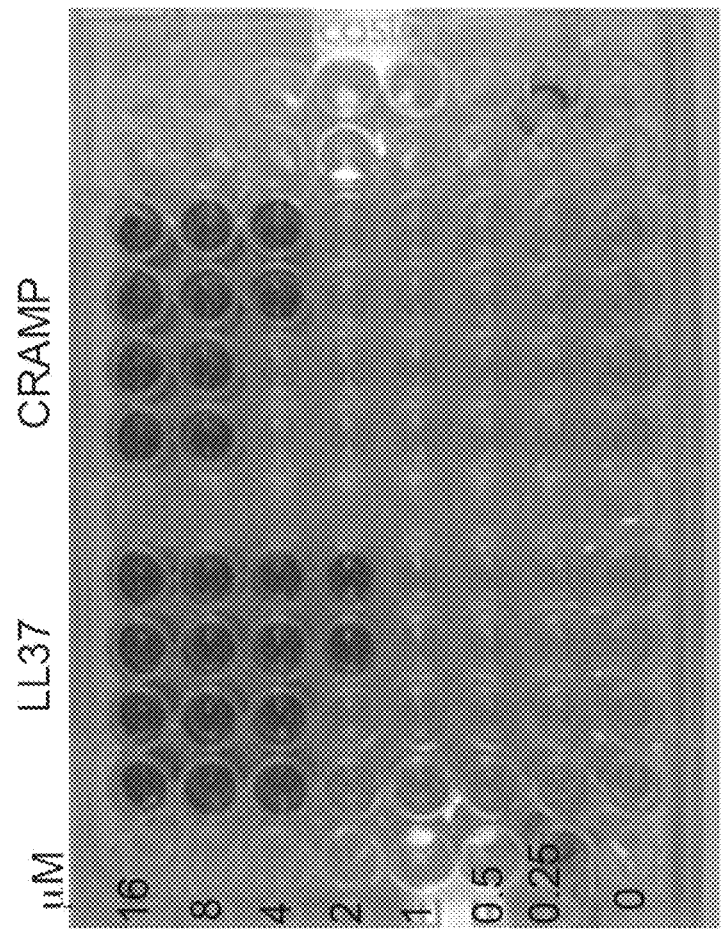
FIG. 19 illustrates data from a cell killing/cell survival assay showing that the ΔgacI mutant is more sensitive to killing by the human cathelicidin antimicrobial peptide LL-37 and the murine cathelicidin mCRAMP, which are produced abundantly by neutrophils and epithelial cells and known to be an important effector of bacterial killing; thus, the GlcNac side chain contributes to cathelicidin resistance.
Figure 20:
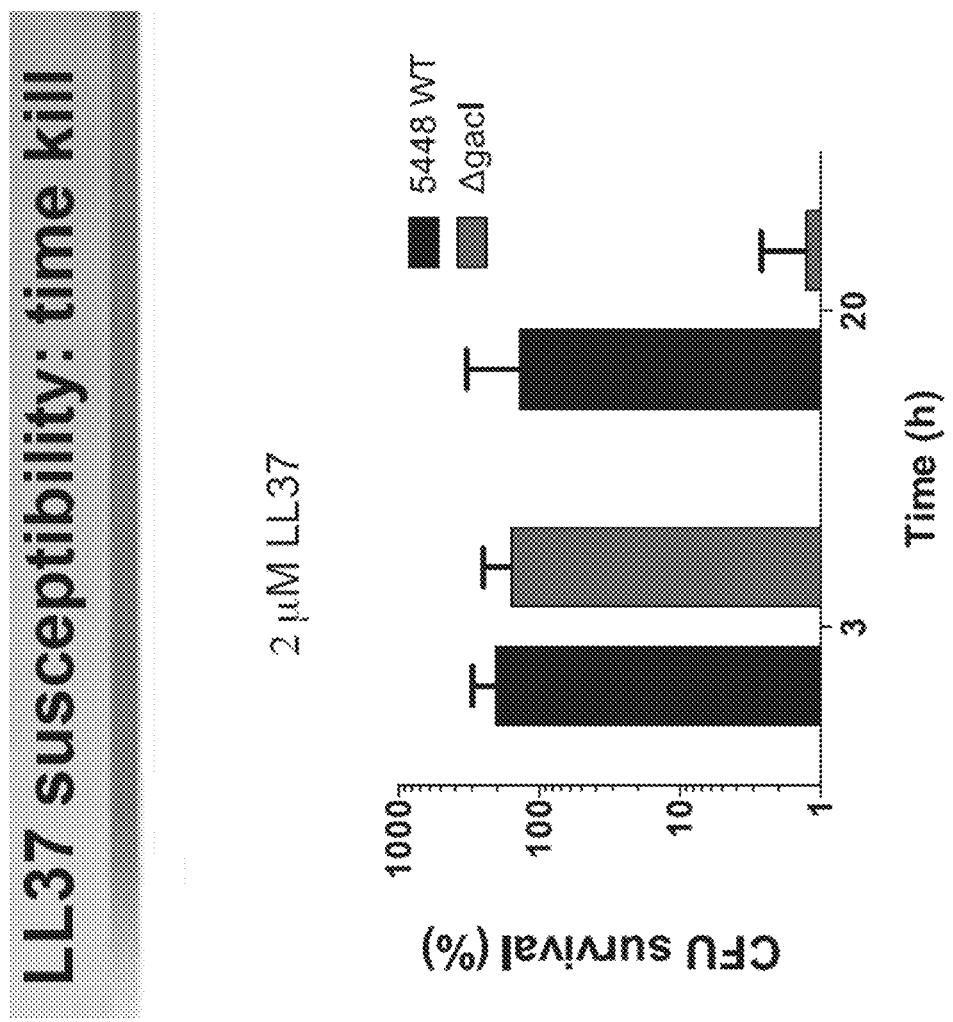
FIG. 20 graphically illustrates data from a cell killing/cell survival assay showing that the ΔgacI mutant is more sensitive to killing by the human cathelicidin antimicrobial peptide LL-37, which is produced abundantly by neutrophils and epithelial cells and known to be an important effector of bacterial killing; thus, the GlcNac side chain contributes to LL-37 resistance.

FIG. 8 schematically illustrates the twelve-gene locus encoding the biosynthetic machinery for the group A streptococcal (GAS) cell wall carbohydrate antigen. Included are proposed gene designations based on homology, designation within the sequenced GAS M1 5005 genome sequence, and length of the gene. Ultimately, we have designated the genes within the locus as gacA-gacL. Highlighted is gene designated gacI because of the role we demonstrate that it plays in adding the GlcNac side chain to the polyrhamnose backbone of the antigen.

Figure 21A:
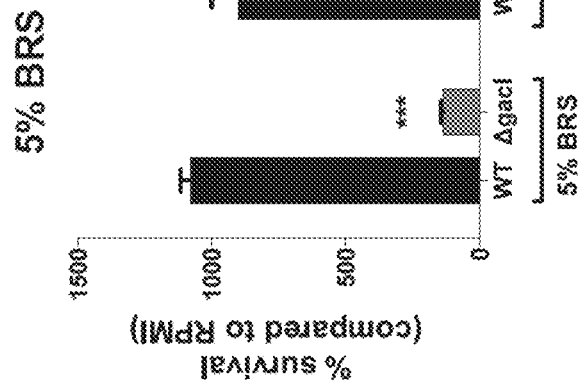
FIG. 21A-B graphically illustrates data from a serum survival assay showing that the ΔgacI mutant is more rapidly killed than the WT parent M1 GAS strain in 5% normal human serum (FIG. 21A) and 5% baby rabbit serum (FIG. 21B), indicating the GlcNac side chain promotes GAS serum resistance, as discussed in Example 1.
Figure 21B:
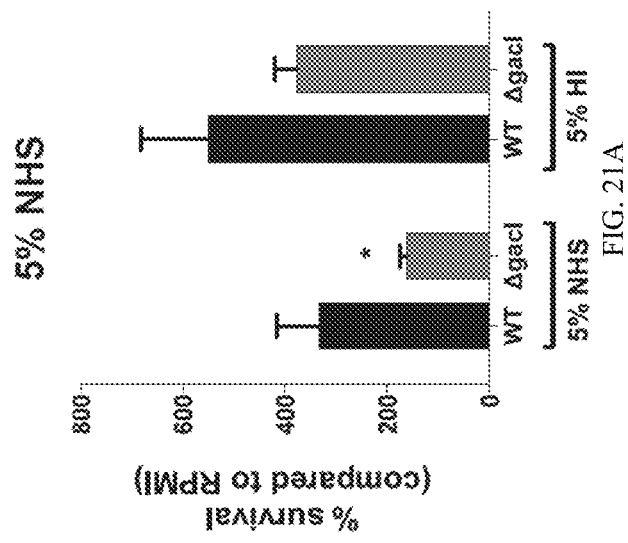
Figure 22A:
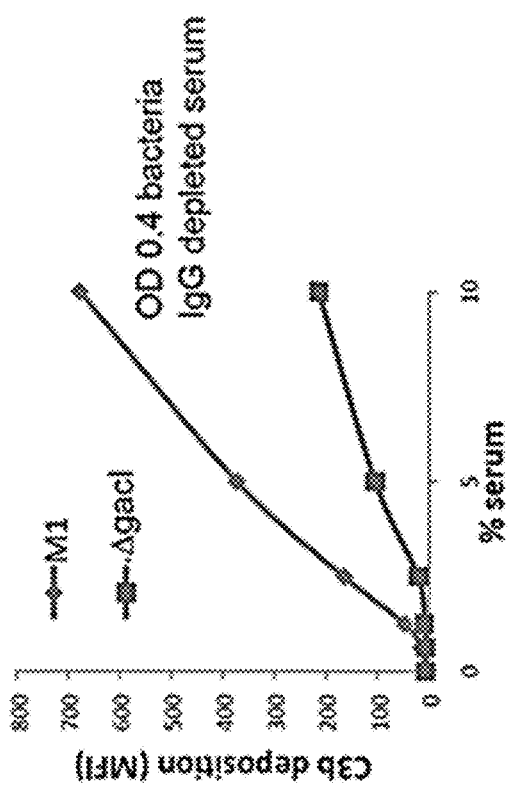
FIG. 22A-B graphically illustrates data from a C3b complement deposition assay showing that compared to the WT parent GAS M1T1 strain the ΔgacI mutant shows less complement deposition via the lectin pathway (in absence of IgG) (FIG. 22B), as compared to the classical complement pathway (FIG. 22A).
Figure 22B:
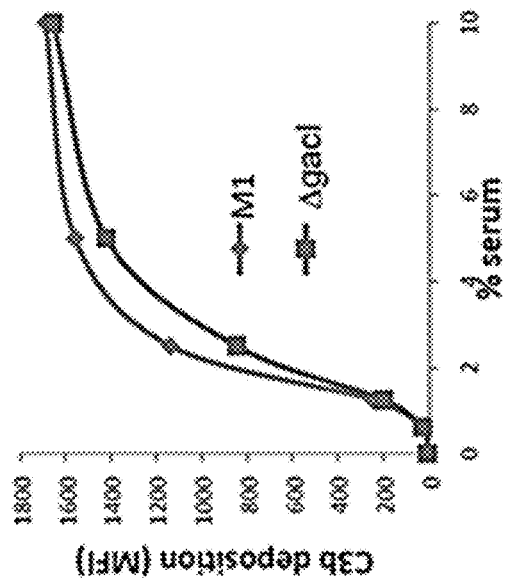
Figures 24A, 24B:
FIG. 24A-B illustrates a test showing the sensitivity of WT (FIG. 24A) and ΔgacI mutant (FIG. 24B) GAS to the antibiotic vancomycin by E-test.
Figure 27:
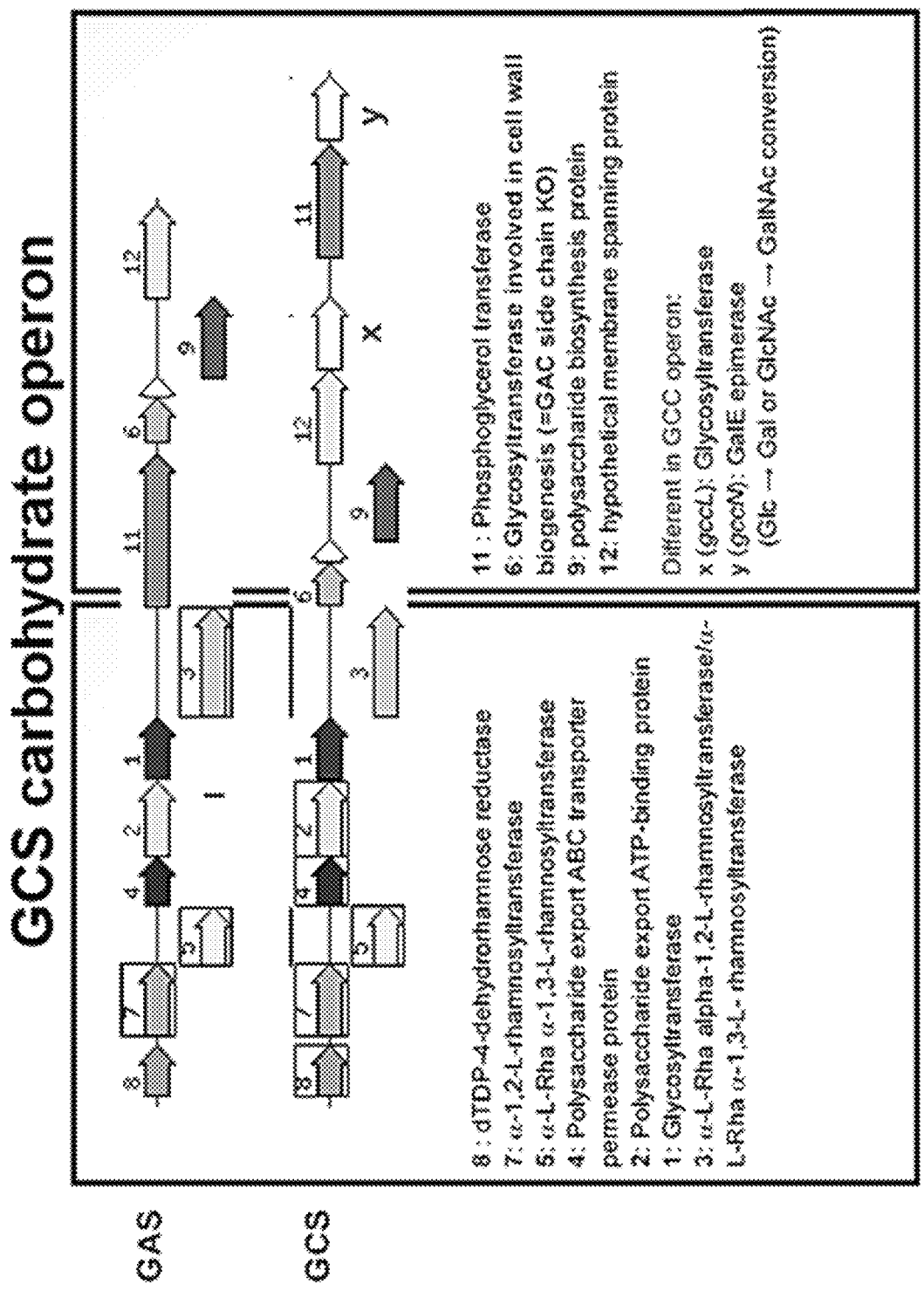
FIG. 27 schematically illustrates a comparison of the gene loci encoding the GAS and GCS cell wall carbohydrate antigens and predicted gene annotations.
Figure 28:
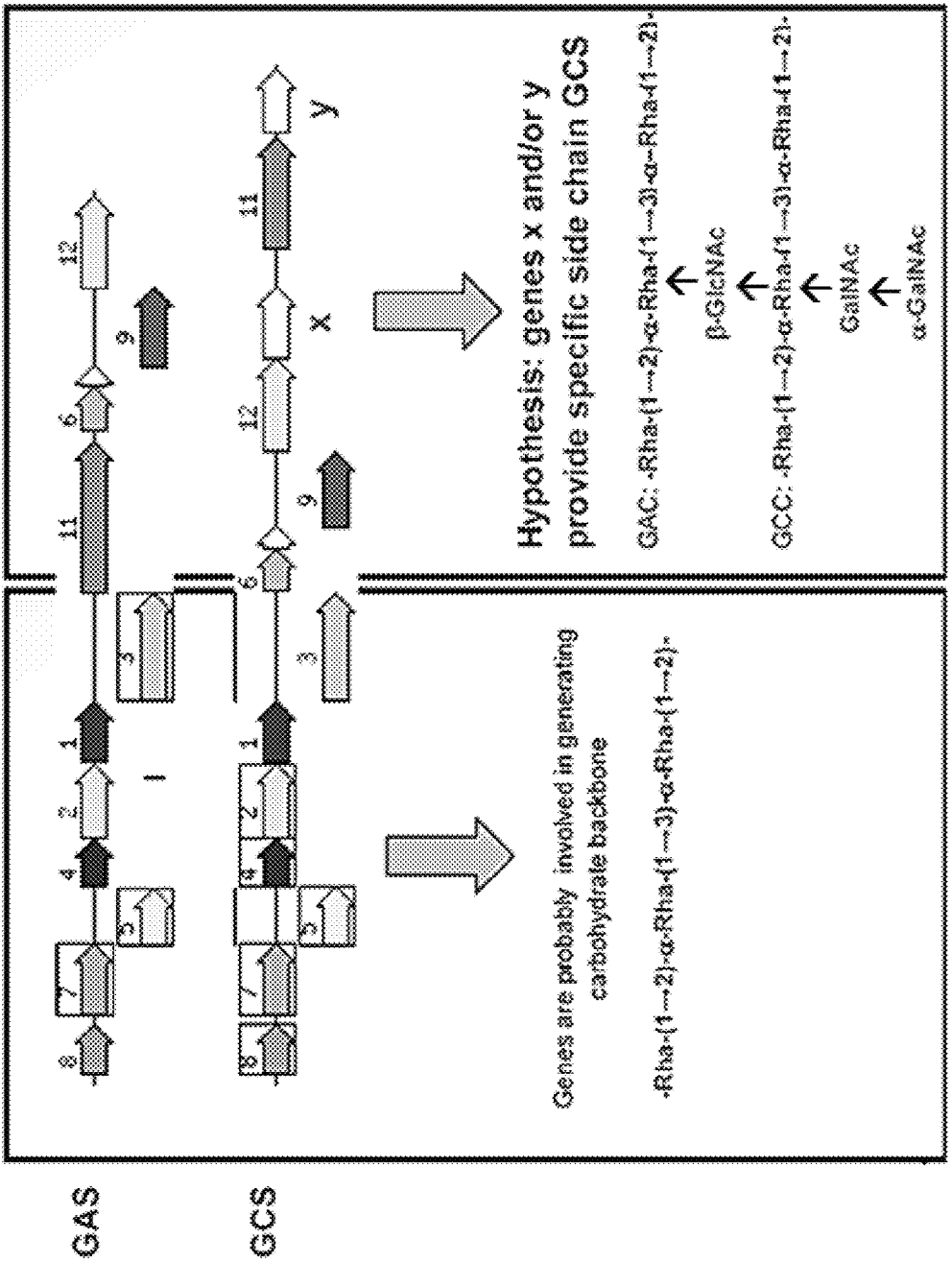
FIG. 28 schematically illustrates a comparison of the gene loci encoding the GAS and GCS cell wall carbohydrate antigens and predicted gene annotations and prediction of genes from GCS that could encode the GlcNAc-GlcNAc side chain.
Figure 29:
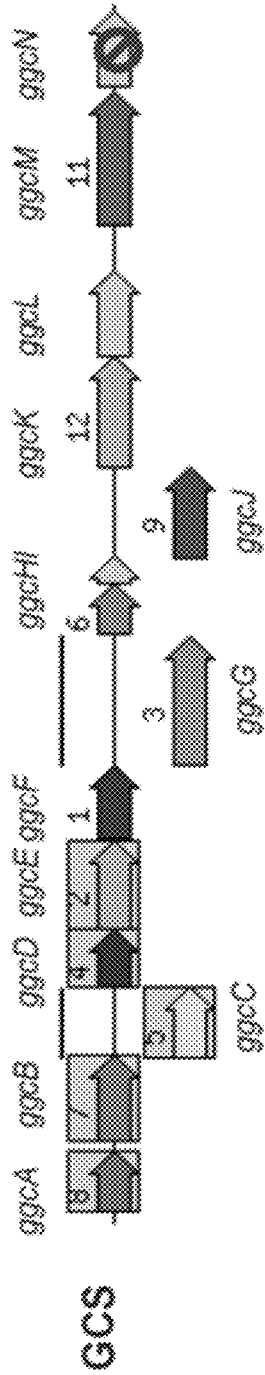
FIG. 29 schematically illustrates an exemplary scheme by which a knockout of the GCS gccN gene yields a ΔgccN mutant lacking the GalNAc-GalNAc side chain that can be studied in virulence and vaccine models analogous to what we have achieved in with the deletion of ΔgacI gene in GAS.
Figure 30:
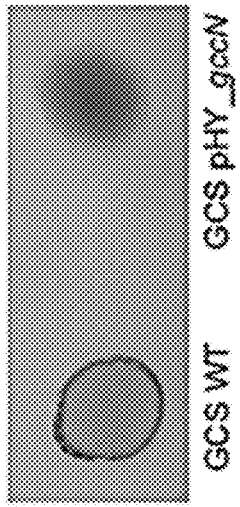
FIG. 30A illustrates the results of a latex bead test showing that knockout of the GCS gccN gene yields a ΔgccN mutant lacking the GalNAc-GalNAc side chain, as confirmed by loss of reactivity in the latex agglutination test.
FIG. 30B schematically illustrates a scheme for synthesizing GCC and GAC.
Figure 31:
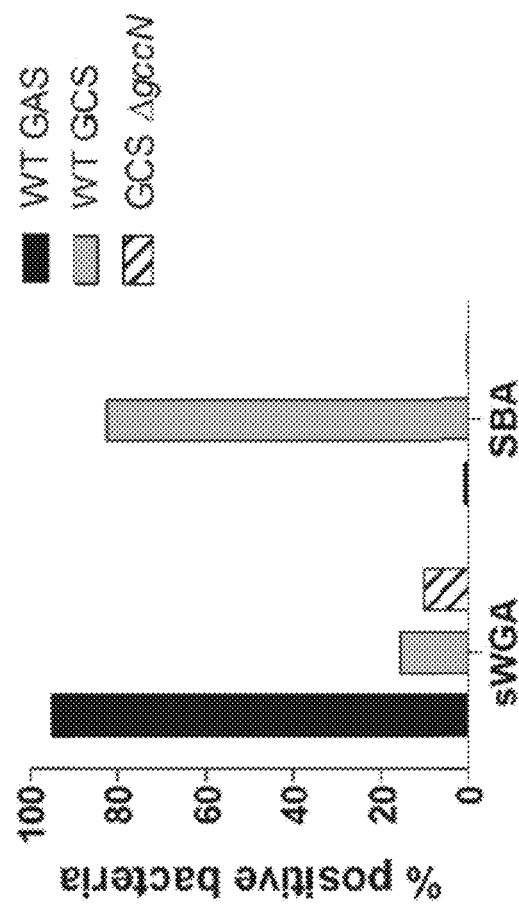
FIG. 31 illustrates the results of a latex bead test showing that knockout of the GCS gccN gene yields a ΔgccN mutant lacking the GalNAc-GalNAc side chain, as confirmed by loss of binding to SBA, a lectin recognizing GalNAc.
Figure 32:
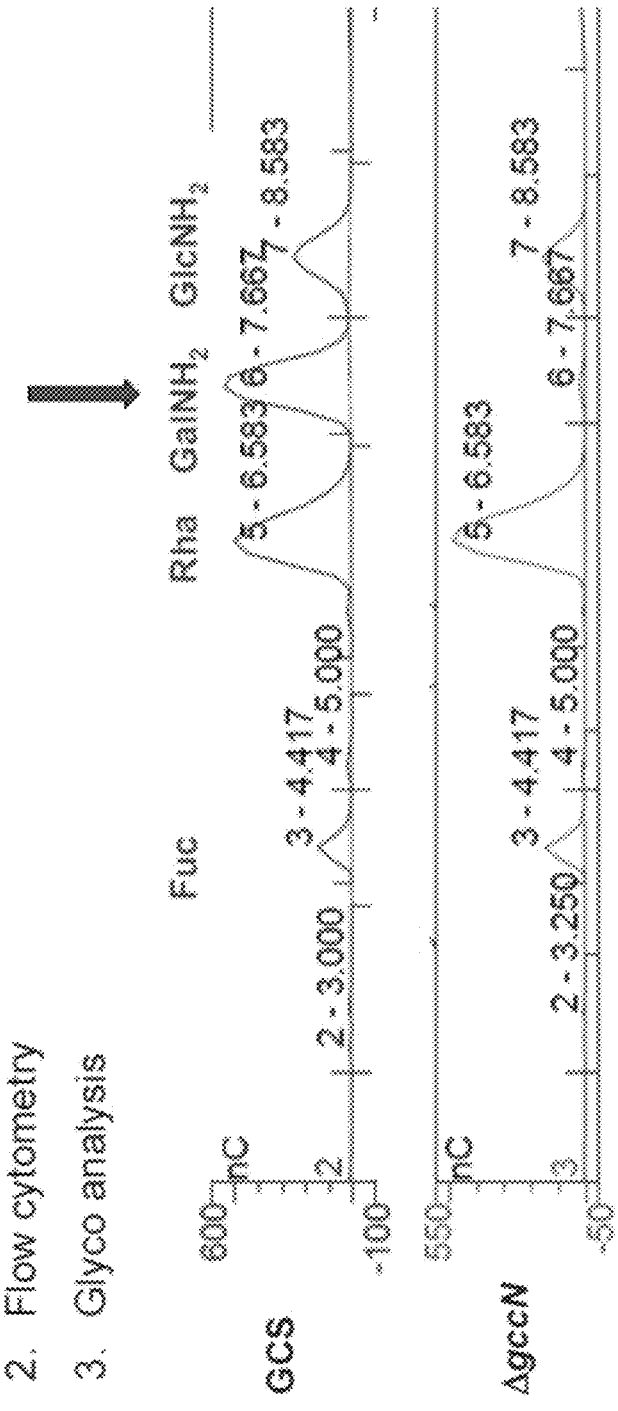
FIG. 32 illustrates the results of a formal glycolinkage analysis showing that knockout of the GCS gccN gene yields a ΔgccN mutant lacking the GalNAc-GalNAc side chain, as confirmed by the glycolinkage analysis.
Figure 33:
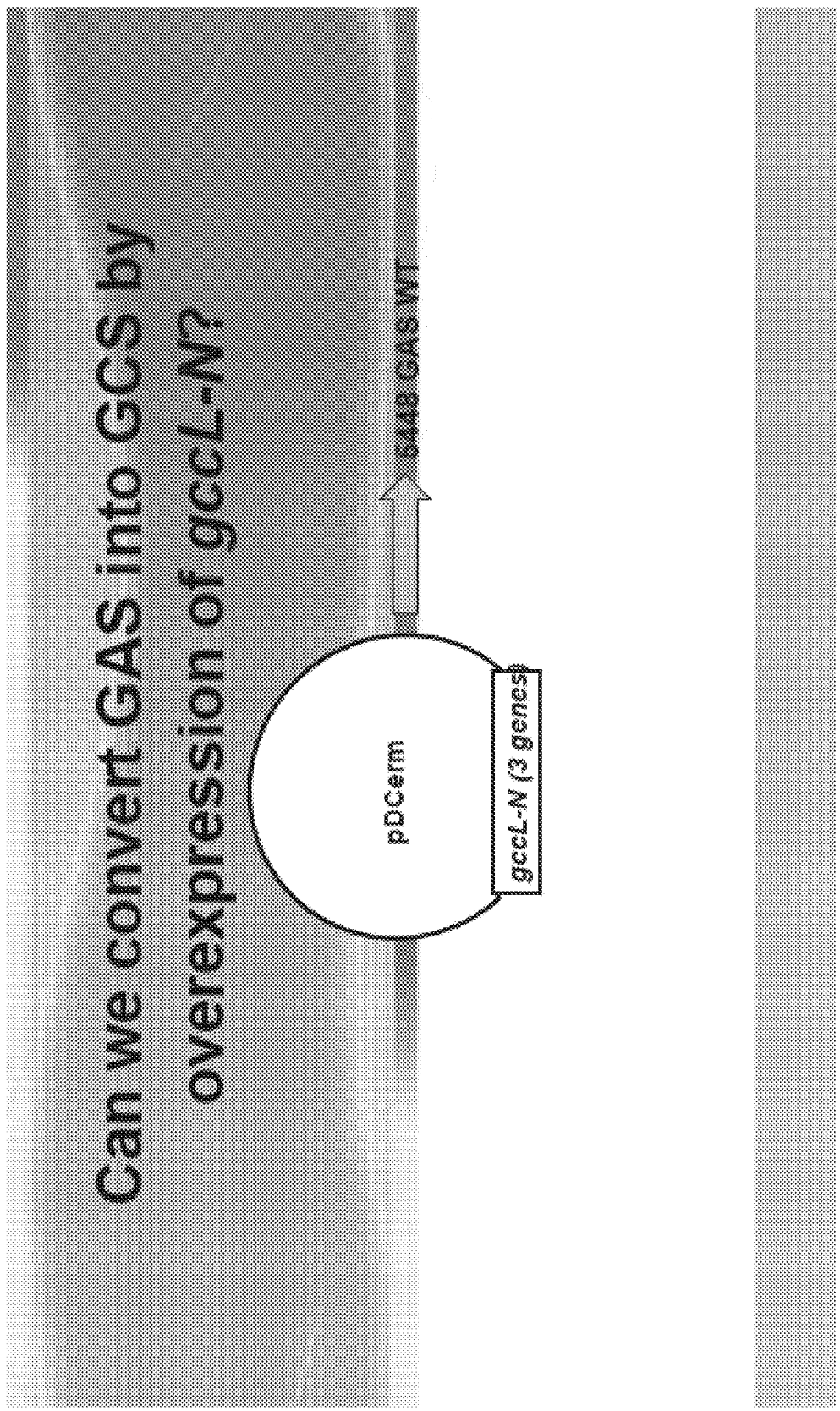
FIG. 33 schematically illustrates that cloning of gccL-N genes from GCS into GAS could encode incorporation of a GlcNAc-GlcNAc side chain.
Figure 35:
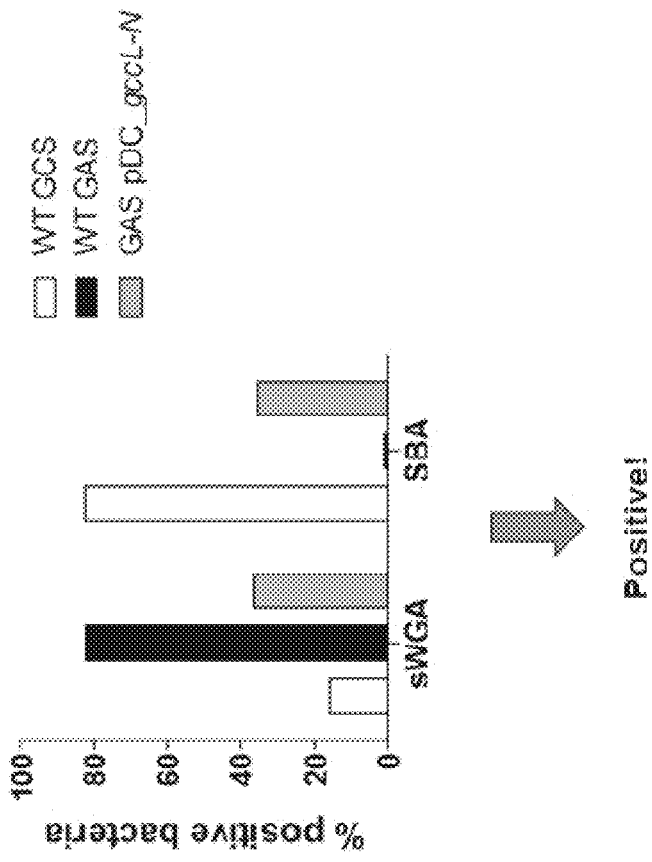
FIG. 35 graphically illustrates the results of a flow cytometry assay demonstrating incorporation of GCS side chain into GAS upon heterologous expression of the gccL-N genes, as confirmed by lectin binding assay.
Figure 36:
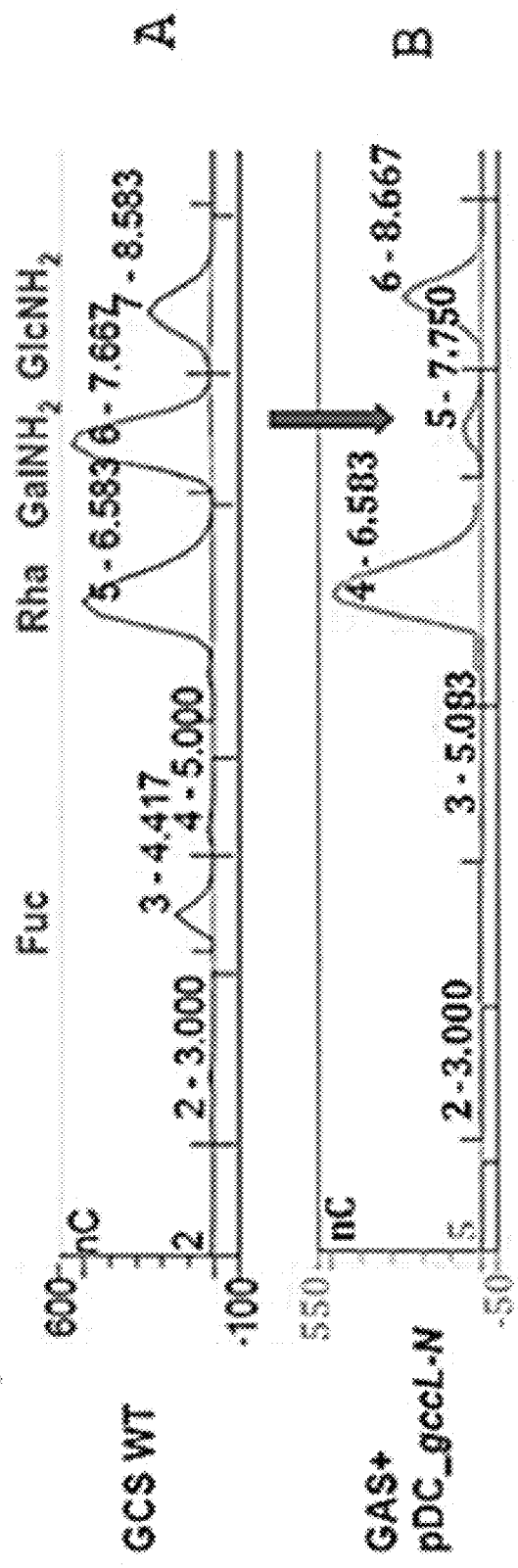
FIG. 36A-B illustrates the results of a carbohydrate composition analysis demonstrating that heterologous expression of the gccL-N genes from GCS into GAS causes incorporation of GlcNAc-GlcNAc side chain by composition analysis.
Figure 37:
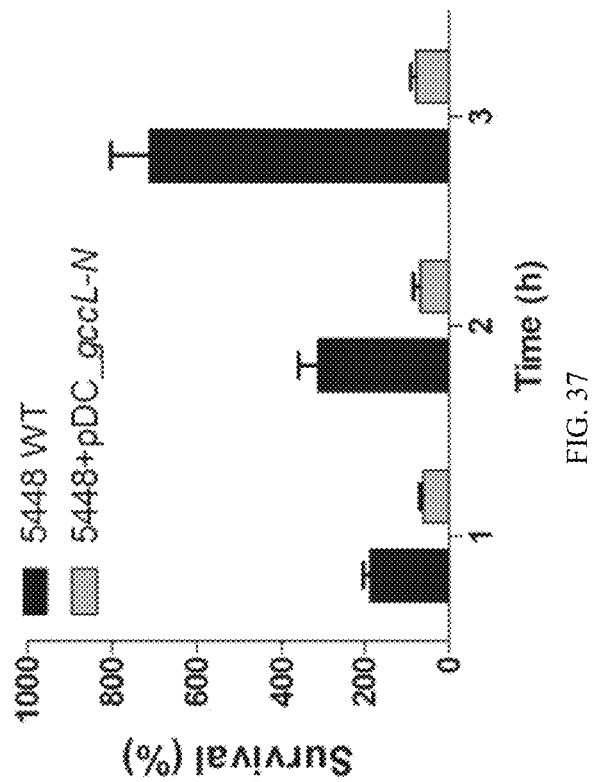
FIG. 37 graphically illustrates the results of a whole blood killing assay demonstrating that heterologous expression of the gccL-N genes from GCS into GAS causes reduced survival in whole blood killing assay.
Figure 40A:
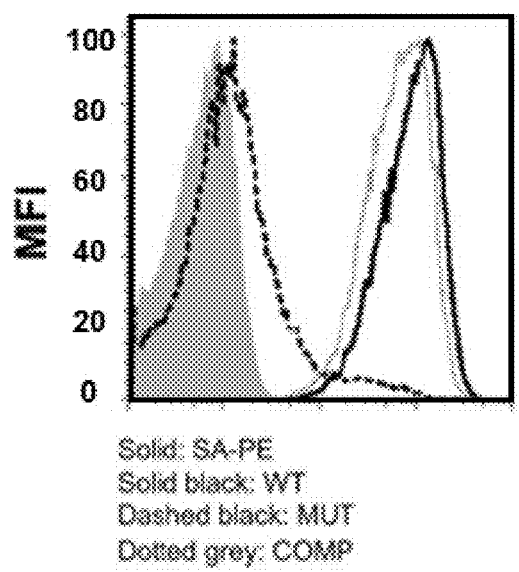
FIG. 40A illustrates a flow cytometry analysis of the wild-type GAS strain showing binding of the sWGA lectin probe, specific for terminal GlcNac sugars, to the bacterial surface.
Figure 40B:
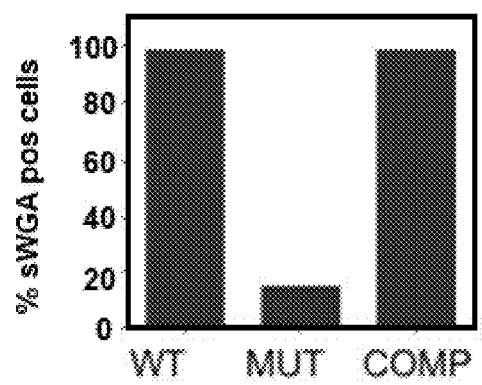
FIG. 40B graphically illustrates how this binding is lost in the ΔgacI mutant and restored in the complemented mutant; the results confirm loss of the GlcNac side chain in the mutant.
Figure 41:
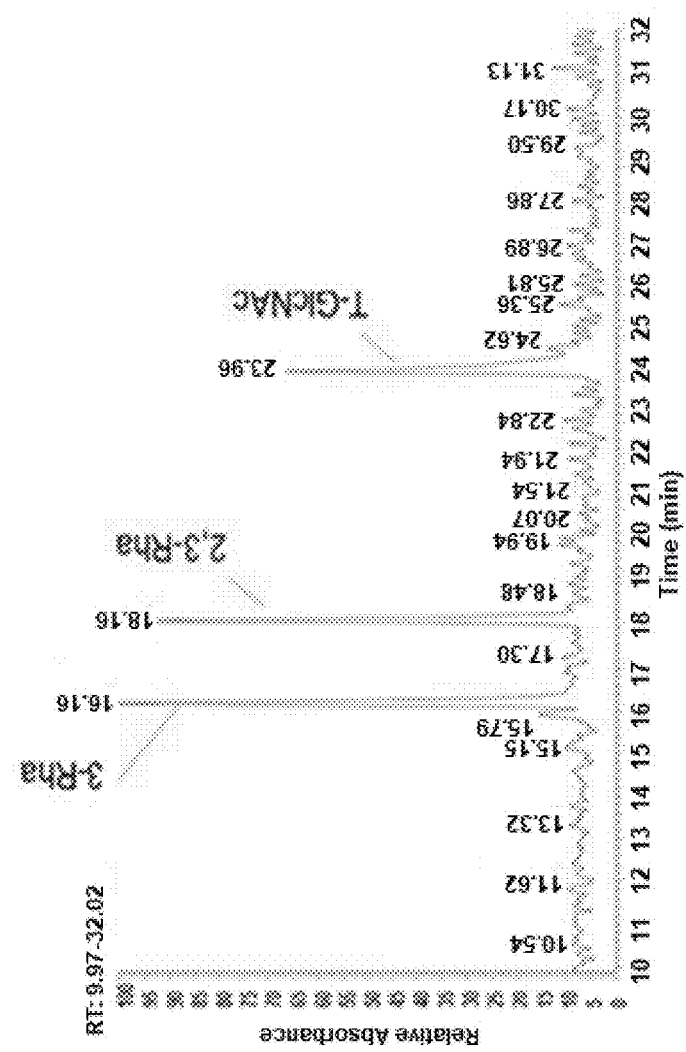
FIG. 41 illustrates a formal glycoanalysis of linkages in the WT M1 GAS carbohydrate, the linkage analysis shows rhamnose sugars and the β-1-3-linked GlcNac side chain.
Figure 42:
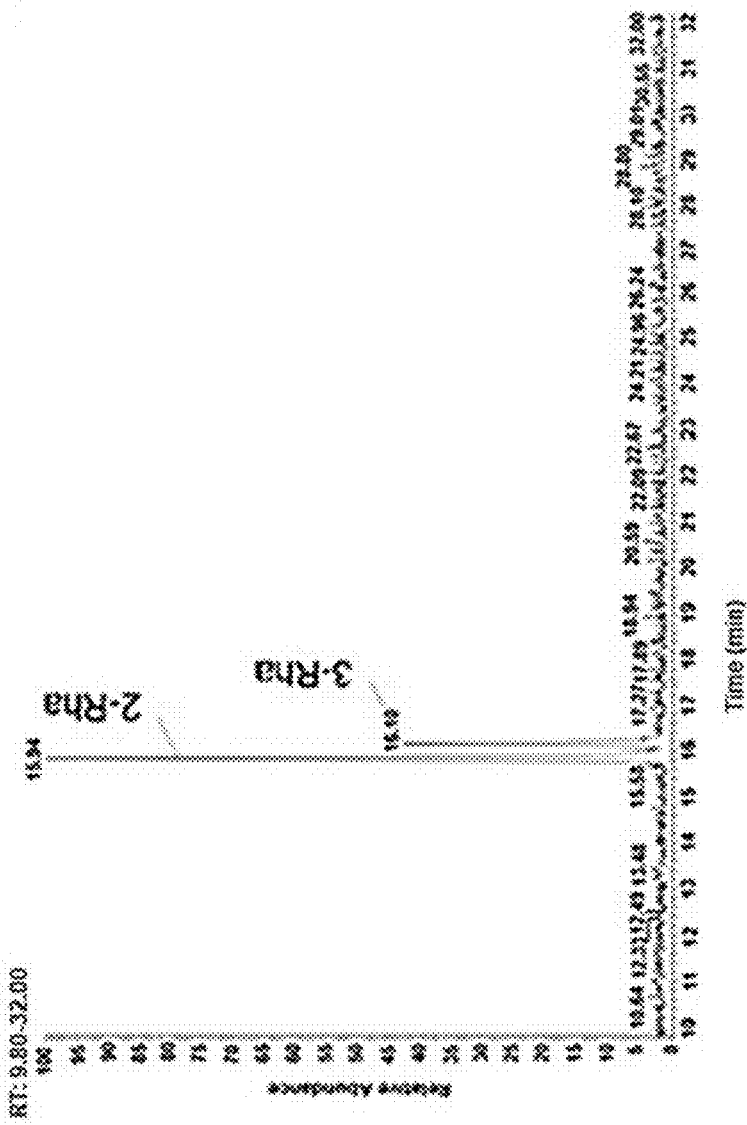
FIG. 42 illustrates a formal glycoanalysis of linkages in the M1 GAS ΔgacI mutant cell wall carbohydrate, the linkage analysis shows unambiguously the loss of the β-1-3-linked GlcNac side chain.
Figure 43:
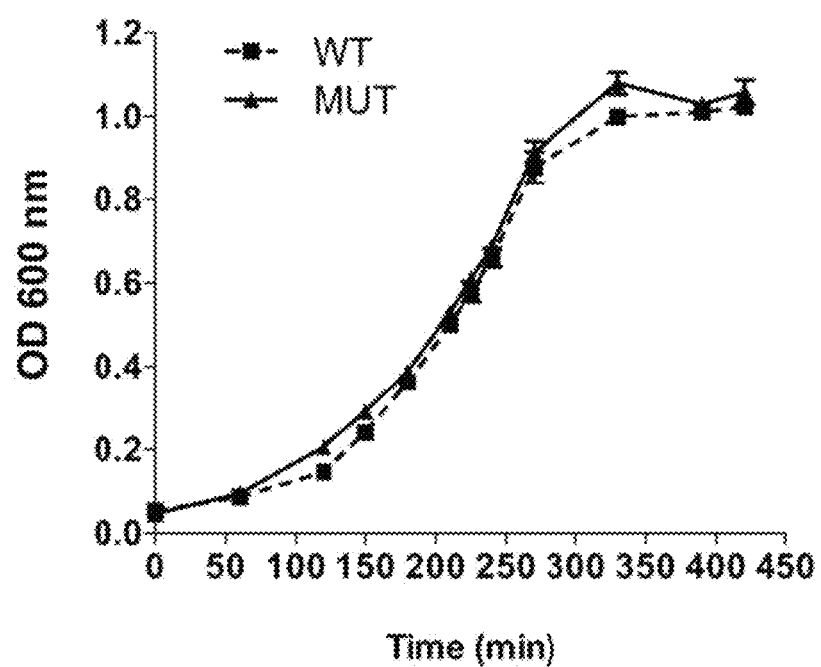
FIG. 43 graphically illustrates that the WT parent M1 GAS strain and the isogenic ΔgacI mutant show similar growth kinetics in bacteriologic growth media (Todd-Hewitt Broth).
Figure 47A:
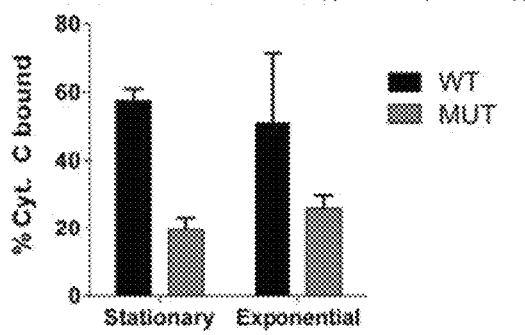
FIG. 47A graphically illustrates a cytochrome C binding assay that indicates the ΔgacI mutant expresses less negative surface charge than the WT parent M1 GAS strain in both stationary and exponential growth phases.
Figure 47B:
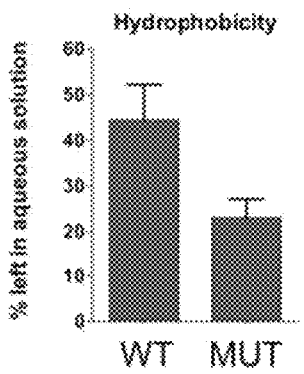
FIG. 47B graphically illustrates an N-hexadecane partition analysis that indicates the ΔgacI mutant is more hydrophobic than the WT parent M1 GAS strain.

FIG. 21 graphically illustrates data from a serum survival assay showing that the ΔgacI mutant is more rapidly killed than the WT parent M1 GAS strain in 5% normal human serum (FIG. 21A) and 5% baby rabbit serum (FIG. 21B), indicating the GlcNac side chain promotes GAS serum resistance. The observed differences remain after heat treatment of the serum to inactivate complement, indicating the differences are not likely to be related to complement. This was confirmed using complement-depleted serum and complement inhibitors.

FIG. 26 schematically illustrates the structure of the Group C streptococcal cell wall carbohydrate (GCC), and a description of its association with human and equine infectious diseases. The GCC shares the same core polyrhamnose backbone as the group A streptococcal cell call carbohydrate antigen (GAC), demonstrating that the ΔgacI mutant polysaccharide can serve as a universal vaccine target (as with the vaccines of this invention) to prevent both GAS and GCS infection.

FIG. 38 schematically illustrates the twelve-gene locus encoding the biosynthetic machinery for the group A streptococcal (GAS) cell wall carbohydrate antigen. Included are proposed gene designations based on homology, designation within the sequenced GAS M1 5005 genome sequence, and length of the gene. We have designated the genes within the locus as gacA-gacL. Highlighted is gacI because of the role we demonstrate that it plays in adding the GlcNac side chain to the polyrhamnose backbone of the antigen.

FIG. 45 graphically illustrates that the WT parent M1 GAS strain and the isogenic ΔgacI mutant express similar levels of hyaluronic acid capsule. Animal passage increases hyaluronic acid expression in M1 GAS (by selection of covS mutants); a similar increase is seen in both the WT parent strain and the isogenic ΔgacI mutant. As listed, several other virulence phenotypes of GAS are not affected by the elimination of the GlcNac side chain in the isogenic ΔgacI mutant.

Figures 49A, 49B:
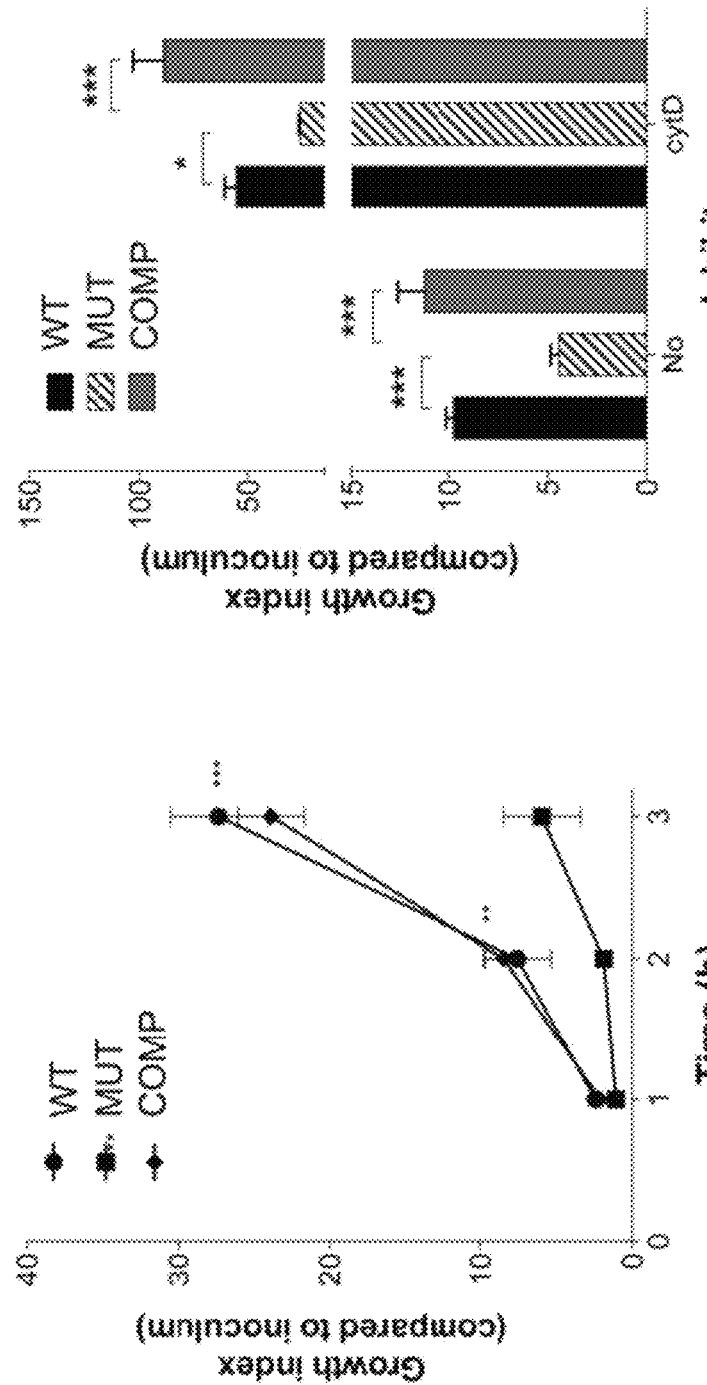
FIGS. 49A and 49B graphically illustrate that the ΔgacI mutant survives less well than the WT parent M1 GAS strain in freshly isolated human whole blood, whereas complementation of the mutation restores WT levels of survival, as discussed in Example 1, below.

FIGS. 49A and 49B graphically illustrate that the ΔgacI mutant survives less well than the WT parent M1 GAS strain in freshly isolated human whole blood, whereas complementation of the mutation restores WT levels of survival. The observed differences between the respective strains are still present when cytochalasin D, an actin microfilament inhibitor is added to block phagocytotic uptake of the bacterial by neutrophils and peripheral blood mononuclear cells. The results further confirm the GlcNAc side chain contributes to whole blood survival.

Figure 50A:
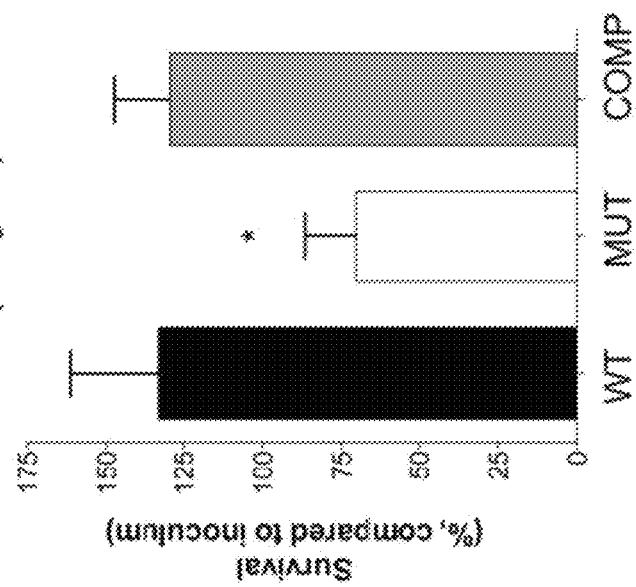
FIGS. 50A and 50B graphically illustrate that the ΔgacI mutant is more rapidly killed than the WT parent M1 GAS strain in a human neutrophil opsonophagocytic killing assay, whereas complementation of the mutation restores WT levels of survival, as discussed in Example 1, below.
Figure 50B:
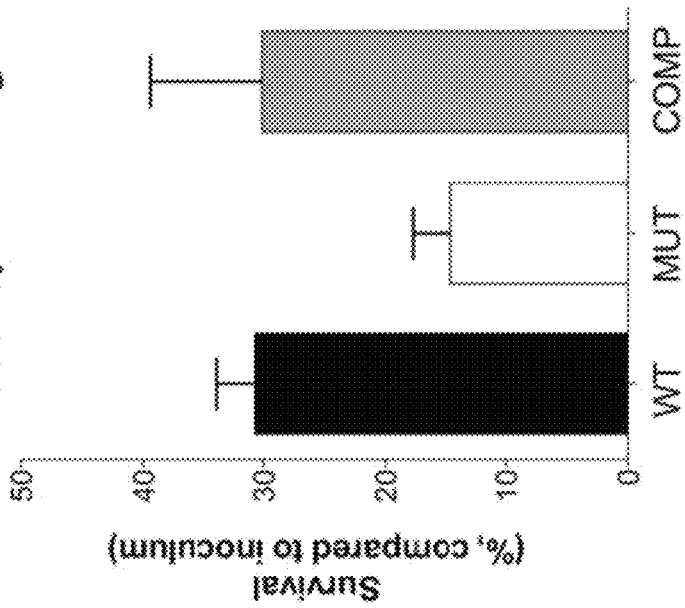
Figures 51A, 51B:
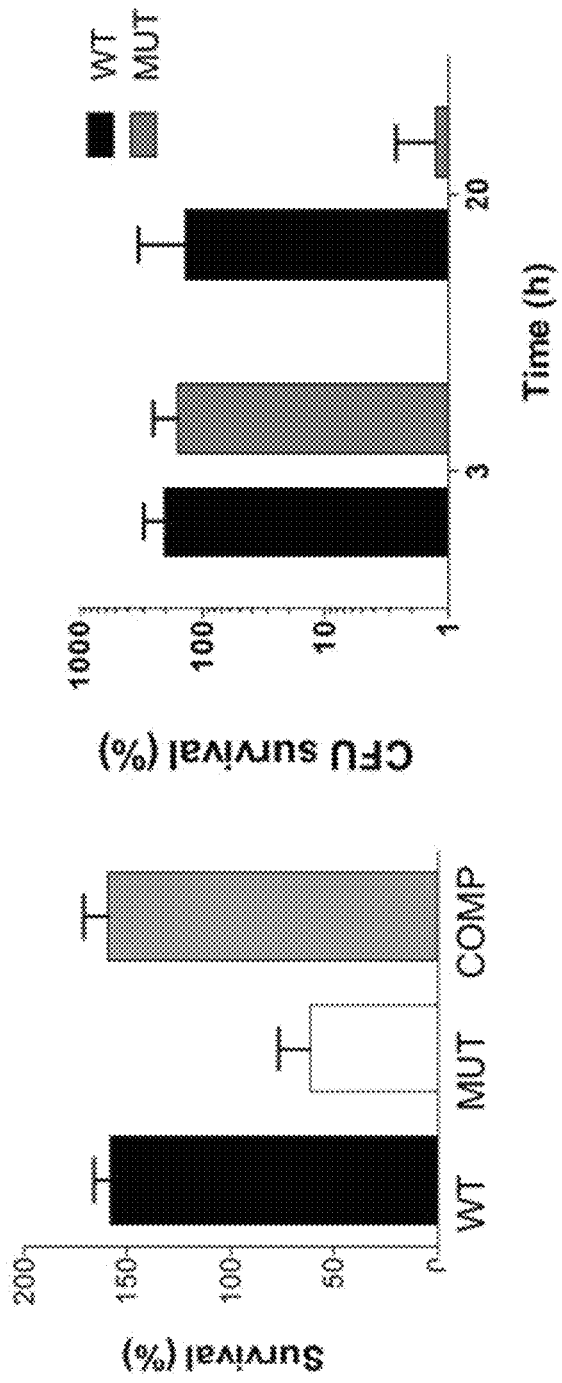
FIG. 51A graphically illustrates that the ΔgacI mutant is more rapidly killed than the WT parent M1 GAS strain in a human neutrophil extracellular trap (NET) killing assay, indicating the GlcNac side chain promotes resistance to extracellular neutrophil killing within NETs.
FIG. 51B graphically illustrates that the ΔgacI mutant is more sensitive to killing by the human cathelicidin antimicrobial peptide LL-37, which is produced abundantly by neutrophils and known to be an important effector of bacterial killing within NETs; thus the GlcNac side chain contributes to cathelidicin resistance.

FIGS. 50A and 50B graphically illustrate that the ΔgacI mutant is more rapidly killed than the WT parent M1 GAS strain in a human neutrophil opsonophagocytic killing assay, whereas complementation of the mutation restores WT levels of survival. The observed differences between the respective strains are still present when cytochalasin D, an actin microfilament inhibitor is added to block phagocytotic uptake of the bacteria by the neutrophils, indicating the GlcNac side chain promotes resistance to both total and extracellular neutrophil killing.

Figure 52A:
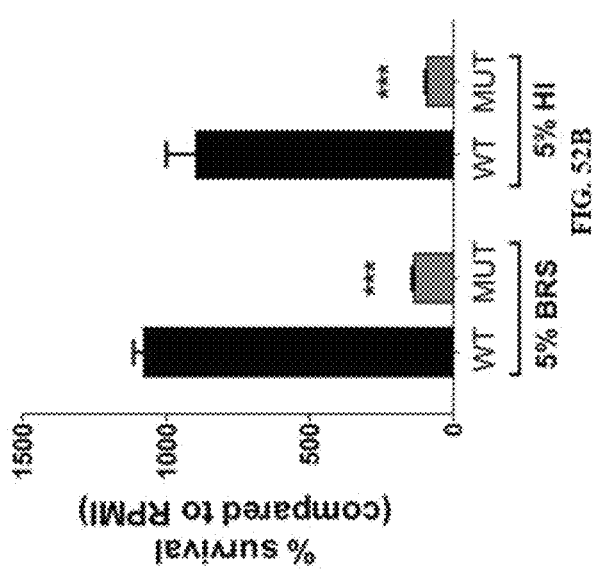
FIGS. 52A and 52B graphically illustrate that the ΔgacI mutant is more rapidly killed than the WT parent M1 GAS strain in 5% normal human serum (FIG. 52A) and 5% baby rabbit serum (FIG. 52B), indicating the GlcNac side chain promotes GAS serum resistance, as discussed in Example 1, below.
Figure 52B:
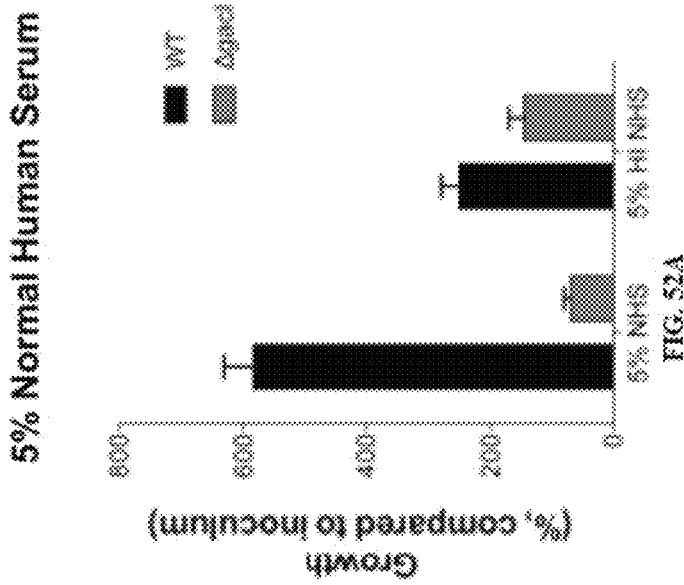
Figure 53:
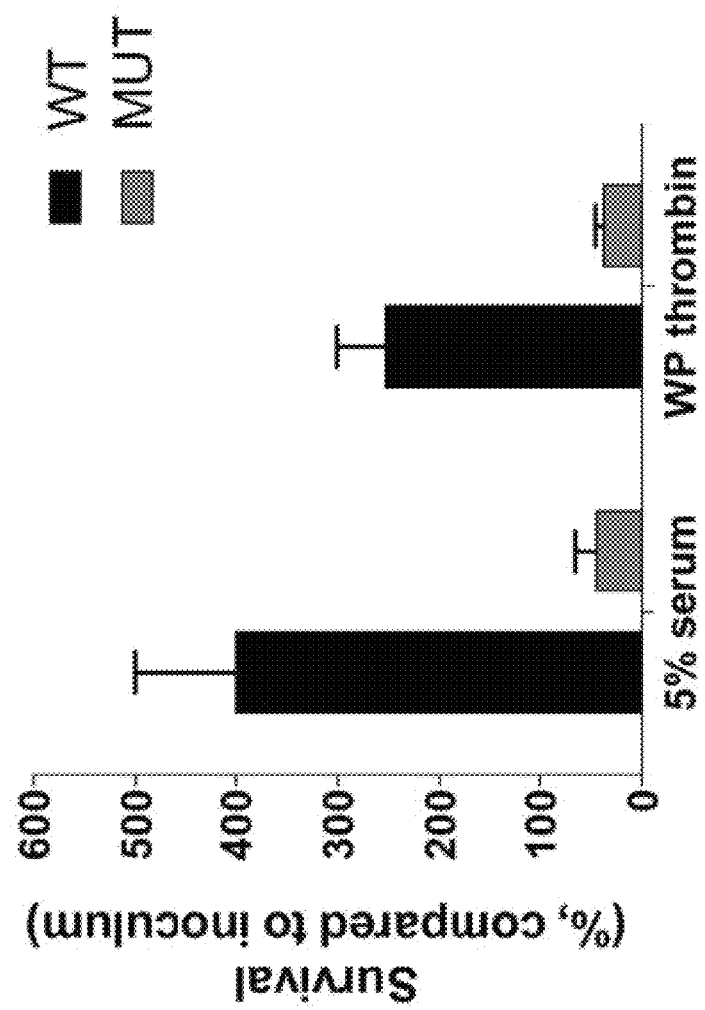
FIG. 53 graphically illustrates that the ΔgacI mutant is more rapidly killed than the WT parent M1 GAS strain by thrombin activated platelets, indicating the GlcNac side chain promotes GAS resistance to platelet-derived antimicrobial peptides.

FIGS. 52A and 52B graphically illustrate that the ΔgacI mutant is more rapidly killed than the WT parent M1 GAS strain in 5% normal human serum (FIG. 52A) and 5% baby rabbit serum (FIG. 52B), indicating the GlcNac side chain promotes GAS serum resistance. The observed differences remain after heat treatment of the serum to inactivate complement, indicating the differences are not likely to be related to complement. This was confirmed using complement-depleted serum and complement inhibitors.

Figure 54A:
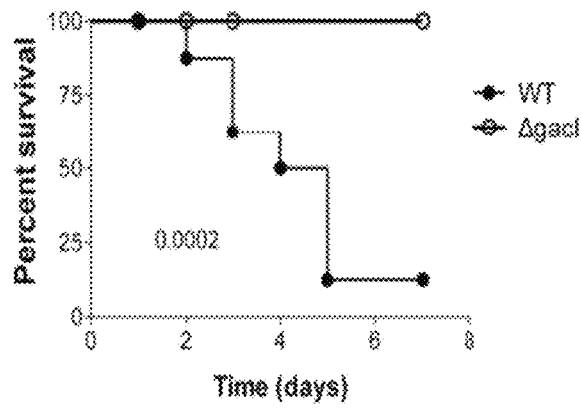
FIG. 54A graphically illustrates that the ΔgacI mutant is markedly attenuated for virulence in a rabbit model of GAS necrotizing pneumonia.
Figures 54B, 54C:
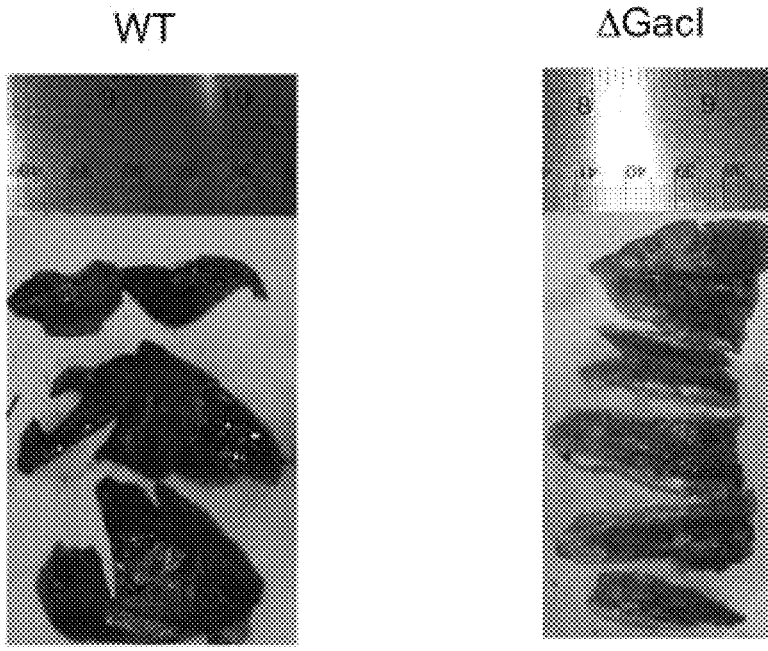
FIGS. 54B and 54C illustrate images of gross examination of the lungs in a wild type and a ΔgacI mutant, as discussed in Example 1, below.

FIG. 54A graphically illustrates that the ΔgacI mutant is markedly attenuated for virulence in a rabbit model of GAS necrotizing pneumonia; FIGS. 54B and 54C illustrate images of gross examination of the lungs in a wild type and a ΔgacI mutant. Whereas 8 of 9 rabbits infected with the WT M1 GAS strain died within 1 week of infection, all animals challenged with an equivalent dose of the ΔgacI mutant survived. Gross examination of the lungs shows massive hemorrhage upon WT GAS infection which is markedly reduced in the ΔgacI mutant-infected animals upon sacrifice at day #7. Thus, the GlcNac side chain on the group A cell wall carbohydrate antigen contributes strongly to GAS virulence.

Figure 55:
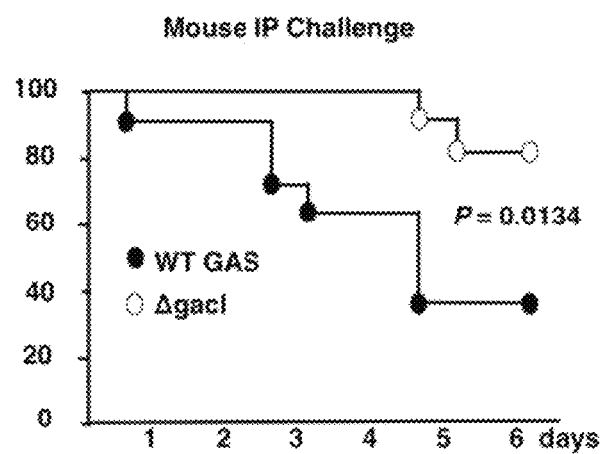
FIG. 55 graphically illustrates that the ΔgacI mutant is significantly attenuated for virulence in a mouse intraperitoneal model of systemic M1 GAS infection; this result further confirms that the GlcNac side chain on the group A cell wall carbohydrate antigen contributes strongly to GAS virulence.

FIG. 55 graphically illustrates that the ΔgacI mutant is significantly attenuated for virulence in a mouse intraperitoneal model of systemic M1 GAS infection; this result further confirms that the GlcNac side chain on the group A cell wall carbohydrate antigen contributes strongly to GAS virulence.

Figure 56:
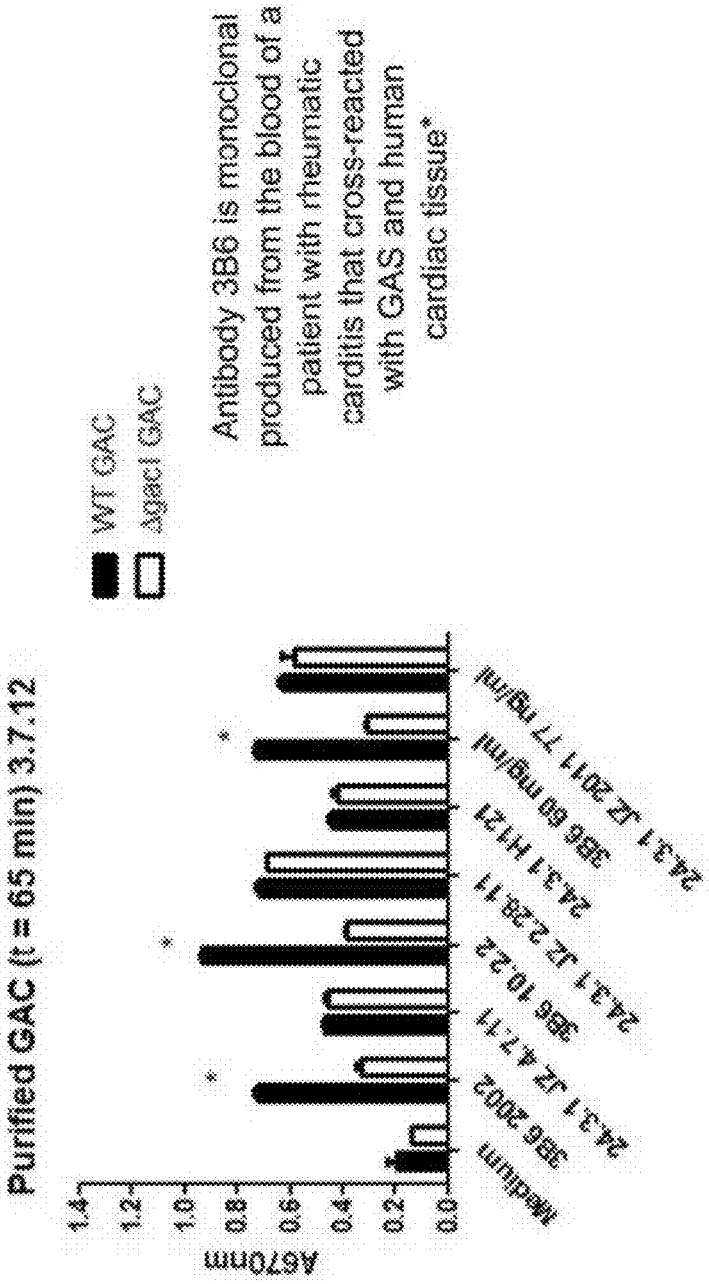
FIG. 56 graphically illustrates that a monoclonal antibody derived from a patient with rheumatic heart disease binds to the WT GAS strain better than the ΔgacI mutant, as discussed in Example 1.
Figure 59A:
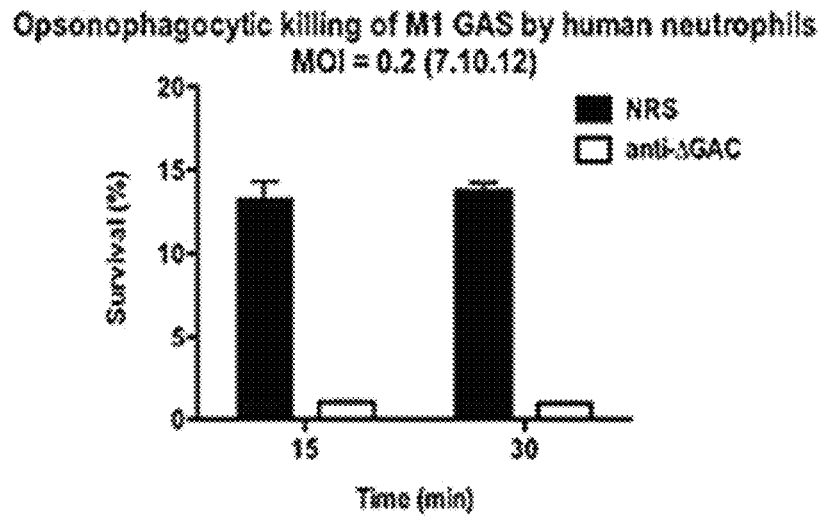
FIG. 59A and FIG. 59B graphically illustrate data from two experiments showing that polyclonal antiserum raised against cell wall carbohydrate purified from the ΔgacI mutant (lacking the GlcNAc side chain) promotes killing of M1 GAS in a human neutrophil opsonophagocytosis assay (compared to normal rabbit serum control); this demonstrates utility of vaccines of the invention as a universal vaccine antigen for GAS.
Figure 59B:
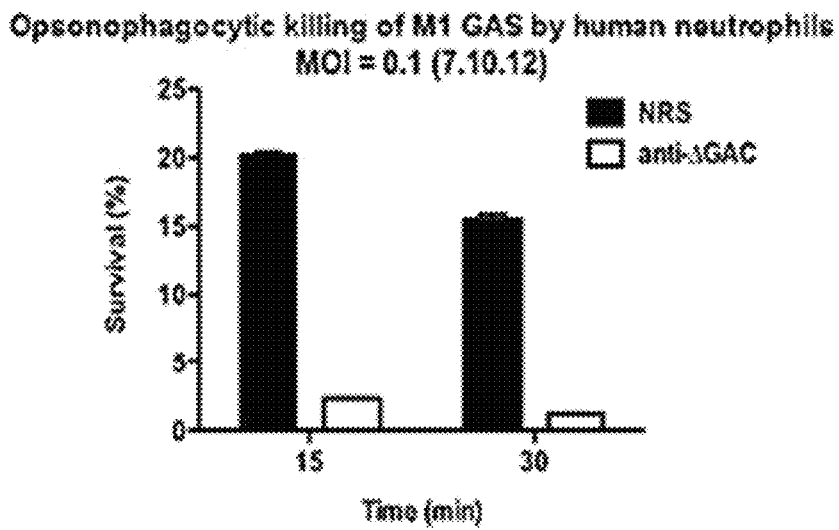
Figure 60:
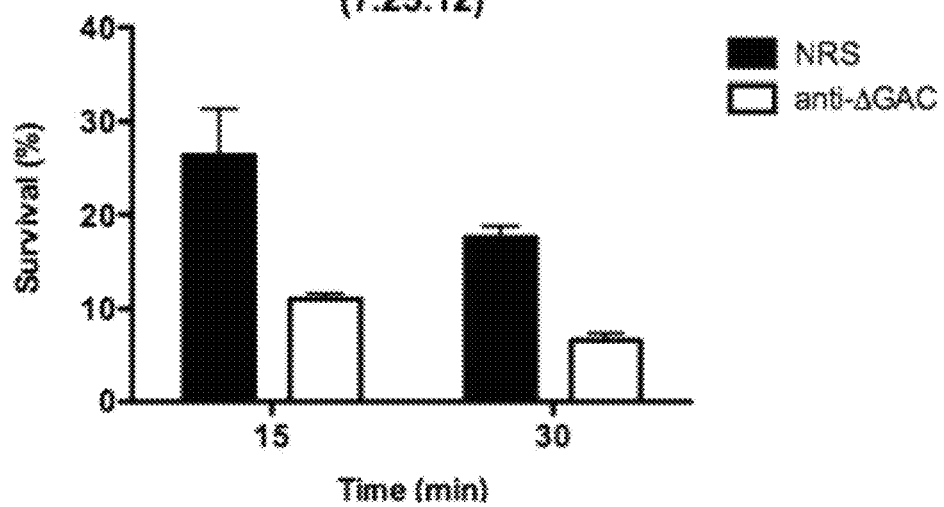
FIG. 60 graphically illustrates data from an experiment showing that polyclonal antiserum raised against the cell wall carbohydrate purified from the ΔgacI mutant (lacking the GlcNAc side chain) promotes killing of M49 GAS in a human neutrophil opsonophagocytosis assay (compared to normal rabbit serum control); this demonstrates utility of vaccines of the invention as a universal vaccine antigen for GAS.
Figure 61:
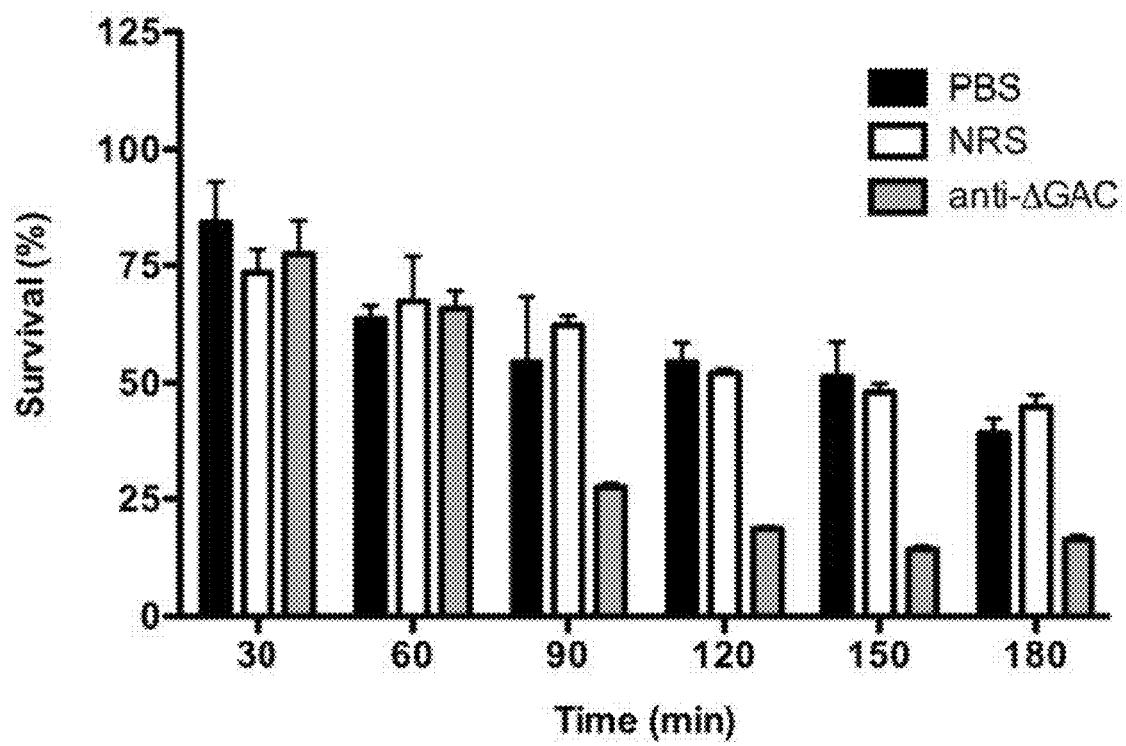
FIG. 61 graphically illustrates data from an experiment showing that polyclonal antiserum raised against the cell wall carbohydrate purified from the ΔgacI mutant (lacking the GlcNAc side chain) promotes opsonophagocytic killing of M1 GAS in human whole blood (compared to normal rabbit serum control); this demonstrates utility of vaccines of the invention as a universal vaccine antigen for GAS.
Figure 64:
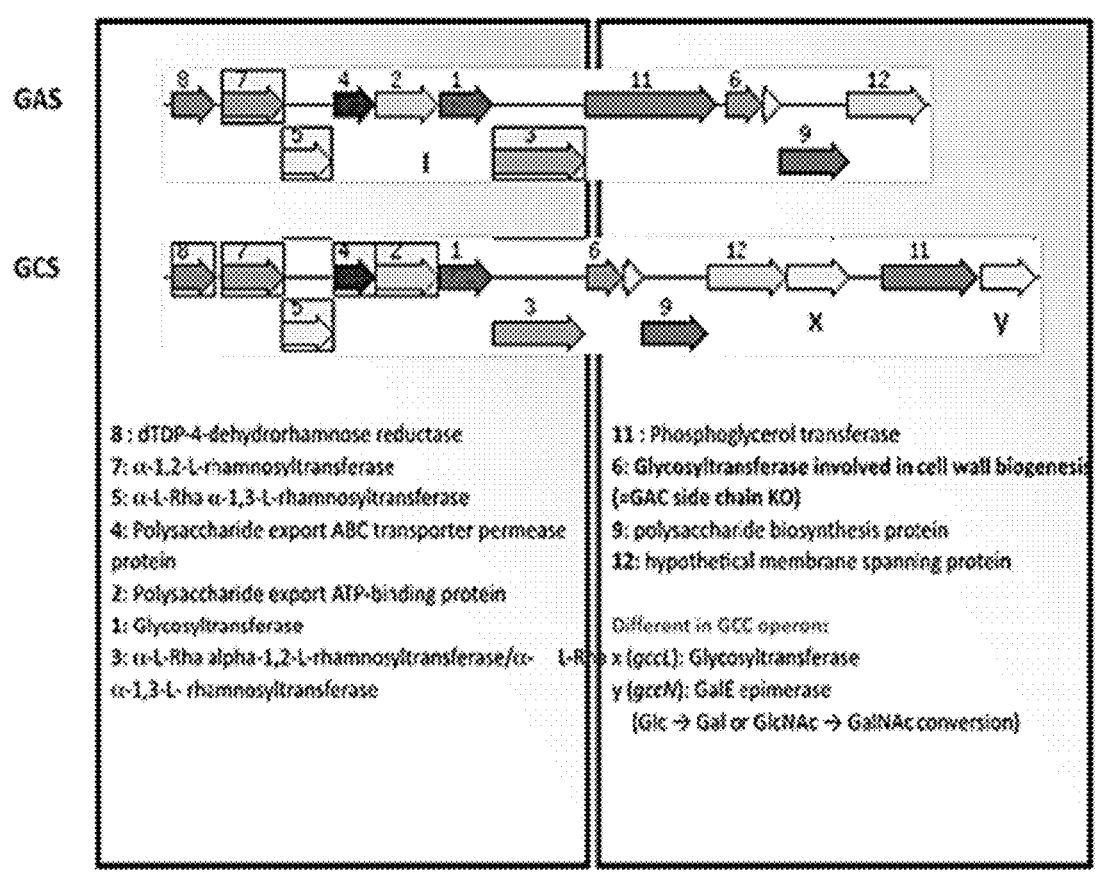
FIG. 64 illustrates a comparison of GAS and GCS cell wall carbohydrate operons, illustrating gene loci encoding the GAS and GCS cell wall carbohydrate antigens and predicted gene annotations.

FIG. 56 graphically illustrates that a monoclonal antibody derived from a patient with rheumatic heart disease, a serious immune-mediate sequelae of GAS pharyngitis that causes morbidity and mortality throughout the developing world, binds to the WT GAS strain better than the ΔgacI mutant. This result confirms that the GlcNac side chain on the GAS cell wall carbohydrate may be the source of cross-reactive antibodies that contribute to the immunopathogenesis of rheumatic fever. This raises serious concerns about using the WT GAS cell wall carbohydrate as a vaccine antigen, whereas the ΔgacI mutant cell wall carbohydrate, lacking the GlcNac side-chain and containing only the non-mammalian sugar rhamnose, should have a favorable profile, and that antibodies and vaccines of the invention having specificity for only the non-mammalian sugar rhamnose also have a favorable profile, e.g., will not be cross-reactive antibodies that contribute to the immunopathogenesis of rheumatic fever.

FIG. 58 summarizes data showing that polyclonal antisera from rabbit immunized with a protein conjugate of the GAC mutant antigen detect WT GAC and WT GAS bacteria. Polyclonal antiserum raised against the cell wall carbohydrate purified from the ΔgacI mutant (lacking the GlcNAc side chain) contains high titers of antibodies that are able to recognize both the mutant (GlcNAc-negative) and wild-type cell wall carbohydrate, as well as mutant and WT GAS bacteria, including a WT GAS bacteria of a different serotype (M49 and M1).

FIG. 62 illustrates the structure of the Group C streptococcal cell wall carbohydrate (GCC) and provides a description of its association with human and equine infectious diseases. The GCC shares the same core polyrhamnose backbone as the group A streptococcal cell call carbohydrate antigen (GAC), demonstrating that vaccines and antibodies of the invention directed to (that specifically bind to) the ΔgacI mutant polysaccharide can serve as a universal vaccine or pharmaceutical to prevent both GAS and GCS infection.

FIG. 63A illustrates a slide showing that if genes from the group C streptococcal operon encoding its group carbohydrate are cloned into group A Streptococcus, evidence of some GalNAc side chain incorporation into the GAS antigen can be demonstrated; FIG. 63B illustrates GalNAc side chain incorporation into the GAS antigen. These data confirm that we are examining and genetically manipulating the biosynthetic loci for both cell wall carbohydrate antigens.

FIG. 65A schematically illustrates how GCS epimerase gccN is required for GCC side chain formation, where GalE epimerases can convert Glc to Gal, and/or GlcNAc to GalNAc, and that no GalE epimerase gccN is present in GAS; and FIG. 65B and FIG. 65C illustrate data showing that GCS epimerase gccN is required for GCC side chain formation. Knockout of the GCS gccN gene yield a ΔgccN mutant lacking the GalNAc-GalNAc side chain that can be studies in virulence and vaccine models analogous to what we have achieved in with the deletion of ΔgacI gene in GAS.

A number of embodiments of the invention have been described. Nevertheless, it will be understood that various modifications may be made without departing from the spirit and scope of the invention. Accordingly, other embodiments are within the scope of the following claims.

What is claimed is:

1. A method of generating a humoral immune response in a mammalian subject to a wild-type Group A *Streptococcus* (GAS), the method comprising administering an effective dose or dosages of an immunogenic composition comprising a purified cell wall carbohydrate antigen of GAS conjugated to a protein, wherein the carbohydrate antigen has a polyrhamnose backbone and completely lacks an N-acetyl-D-glucosamine (GlcNac) side chain, wherein the method induces antibodies that bind specifically to the cell wall carbohydrate antigen of a GAS and promotes opsonophagocytic killing of the wild-type GAS in the subject.

2. A method of generating a humoral immune response in a mammalian subject to a wild-type Group A *Streptococcus* (GAS), the method comprising administering an effective dose or dosages of an immunogenic composition comprising an antigen consisting of a purified cell wall carbohydrate antigen of GAS conjugated to a protein, wherein the carbohydrate antigen has a polyrhamnose backbone and completely lacks an N-acetyl-D-glucosamine (GlcNac) side chain, wherein the method induces antibodies that bind specifically to the cell wall carbohydrate antigen of a wild type GAS and promotes opsonophagocytic killing of the GAS in the subject.

3. The method of claim 1, wherein the mammalian subject has strep throat, impetigo, cellulitis, necrotizing fasciitis, toxic shock syndrome, or post-streptococcal glomerulonephritis.

4. The method of claim 2, wherein the mammalian subject has strep throat, impetigo, cellulitis, necrotizing fasciitis, toxic shock syndrome, or post-streptococcal glomerulonephritis.

5. The method of claim 1, wherein the mammalian subject has rheumatic fever.

6. The method of claim 2, wherein the mammalian subject has rheumatic fever.

7. The method of claim 1, wherein the immunogenic composition further comprises an adjuvant.

8. The method of claim 7, wherein the adjuvant is selected from the group consisting of Freund's adjuvant, alum, aluminum phosphate, aluminum hydroxide, squalene, complete Freund's adjuvant, and levamisole.

9. The method of claim 1, wherein the immunogenic composition further comprises a pharmaceutical carrier.

10. The method of claim 9, wherein the pharmaceutical carrier is a liposome.

11. The method of claim 1, wherein the protein is a GAS protein.

12. The method of claim 1, wherein the protein is not a GAS protein.

13. The method of claim 2, wherein the immunogenic composition further comprises an adjuvant.

14. The method of claim 13, wherein the adjuvant is selected from the group consisting of Freund's adjuvant, alum, aluminum phosphate, aluminum hydroxide, squalene, complete Freund's adjuvant, and levamisole.

15. The method of claim 2, wherein the immunogenic composition further comprises a pharmaceutical carrier.

16. The method of claim 15, wherein the pharmaceutical carrier is a liposome.

17. The method of claim 2, wherein the protein is a GAS protein.

18. The method of claim 2, wherein the protein is not a GAS protein.

* * * * *